(12) United States Patent
Castanedo et al.

(10) Patent No.: US 7,893,059 B2
(45) Date of Patent: Feb. 22, 2011

(54) THIAZOLOPYRIMIDINE PI3K INHIBITOR COMPOUNDS AND METHODS OF USE

(75) Inventors: Georgette M. Castanedo, Redwood City, CA (US); Janet L. Gunzner, Berkeley, CA (US); Kimberly Malesky, San Francisco, CA (US); Simon Mathieu, Burlingame, CA (US); Alan G. Olivero, Half Moon Bay, CA (US); Daniel P. Sutherlin, South San Francisco, CA (US); Shumei Wang, Foster City, CA (US); Bing-Yan Zhu, Palo Alto, CA (US); Irina Chuckowree, Slough (GB); Adrian Folkes, Slough (GB); Sally Oxenford, Slough (GB); Nan Chi Wan, Slough (GB)

(73) Assignees: Genentech, Inc., South San Francisco, CA (US); F. Hoffmann-La Roche AG, Basel (CH)

( * ) Notice: Subject to any disclaimer, the term of this patent is extended or adjusted under 35 U.S.C. 154(b) by 200 days.

(21) Appl. No.: 12/236,317

(22) Filed: Sep. 23, 2008

(65) Prior Publication Data
US 2009/0118275 A1  May 7, 2009

Related U.S. Application Data

(60) Provisional application No. 60/974,708, filed on Sep. 24, 2007.

(51) Int. Cl.
*A61K 31/5377* (2006.01)
*C07D 413/14* (2006.01)
(52) U.S. Cl. .................... 514/234.2; 544/117
(58) Field of Classification Search .............. 514/234.2; 544/117
See application file for complete search history.

(56) References Cited

U.S. PATENT DOCUMENTS

| | | | |
|---|---|---|---|
| 3,661,908 A * | 5/1972 | Woitun et al. ............. 544/278 |
| 3,850,917 A | 11/1974 | Muller et al. |
| 6,492,383 B1 | 12/2002 | Munchhof et al. |
| 6,608,053 B2 | 8/2003 | Hayakawa et al. |
| 2007/0185139 A1 | 8/2007 | Binnun et al. |
| 2008/0039459 A1 | 2/2008 | Folkes et al. |
| 2008/0076758 A1 | 3/2008 | Folkes et al. |
| 2008/0076768 A1 | 3/2008 | Chuckowree et al. |
| 2008/0207609 A1 | 8/2008 | Shuttleworth et al. |
| 2008/0207611 A1 | 8/2008 | Shuttleworth et al. |
| 2008/0242665 A1 | 10/2008 | Bayliss et al. |
| 2008/0269210 A1 | 10/2008 | Castanedo et al. |

FOREIGN PATENT DOCUMENTS

| | | |
|---|---|---|
| WO | WO 2006/046035 | 5/2006 |
| WO | WO 2006/114606 | 11/2006 |
| WO | WO 2007/122410 | 11/2007 |
| WO | WO 2007/127175 | 11/2007 |
| WO | WO 2008/152387 | 12/2008 |
| WO | WO 2008/152390 | 12/2008 |
| WO | WO 2008/152394 | 12/2008 |

OTHER PUBLICATIONS

International Search Report and Written Opinion of the International Searching Authority, PCT/US2008/077394, Dec. 10, 2008.

* cited by examiner

*Primary Examiner*—Rebecca L Anderson
(74) *Attorney, Agent, or Firm*—Viksnins Harris & Padys PLLP

(57) ABSTRACT

Compounds of Formulas Ia and Ib, and including stereoisomers, geometric isomers, tautomers, solvates, metabolites and pharmaceutically acceptable salts thereof, are useful for inhibiting lipid kinases including PI3K, and for treating disorders such as cancer mediated by lipid kinases. Methods of using compounds of Formula Ia and Ib for in vitro, in situ, and in vivo diagnosis, prevention or treatment of such disorders in mammalian cells, or associated pathological conditions, are disclosed.

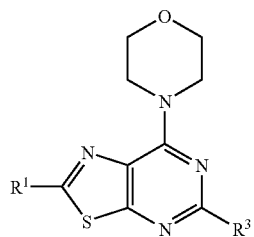

Ia

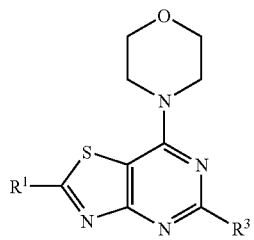

Ib

38 Claims, No Drawings

THIAZOLOPYRIMIDINE PI3K INHIBITOR COMPOUNDS AND METHODS OF USE

CROSS REFERENCE TO RELATED APPLICATIONS

This non-provisional application filed under 37 CFR §1.53(b), claims the benefit under 35 USC §119(e) of U.S. Provisional Application Ser. No. 60/974,708 filed on 24 Sep. 2007, which is incorporated by reference in entirety.

FIELD OF THE INVENTION

The invention relates generally to compounds with anti-cancer activity and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60). Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The PI3 kinase family comprises at least 15 different enzymes sub-classified by structural homology and are divided into 3 classes based on sequence homology and the product formed by enzyme catalysis. The class I PI3 kinases are composed of 2 subunits: a 110 kd catalytic subunit and an 85 kd regulatory subunit. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Class I PI3 kinases are involved in important signal transduction events downstream of cytokines, integrins, growth factors and immunoreceptors, which suggests that control of this pathway may lead to important therapeutic effects such as modulating cell proliferation and carcinogenesis. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate. Class III PI3Ks can only phosphorylate PI.

The initial purification and molecular cloning of PI3 kinase revealed that it was a heterodimer consisting of p85 and p110 subunits (Otsu et al (1991) Cell 65:91-104; Hiles et al (1992) Cell 70:419-29). Since then, four distinct Class I PI3Ks have been identified, designated PI3K α (alpha), β (beta), δ (delta), and ω (gamma), each consisting of a distinct 110 kDa catalytic subunit and a regulatory subunit. More specifically, three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are also distinct.

The main PI3-kinase isoform in cancer is the Class I PI3-kinase, p110a (alpha) (U.S. Pat. Nos. 5,824,492; 5,846,824; 6,274,327). Other isoforms are implicated in cardiovascular and immune-inflammatory disease (Workman P (2004) "Inhibiting the phosphoinositide 3-kinase pathway for cancer treatment" Biochem Soc Trans 32:393-396; Patel et al (2004) "Identification of potent selective inhibitors of PI3K as candidate anticancer drugs" Proceedings of the American Association of Cancer Research (Abstract LB-247) 95th Annual Meeting, Mar. 27-31, Orlando, Fla., USA; Ahmadi K and Waterfield M D (2004) "Phosphoinositide 3-Kinase: Function and Mechanisms" Encyclopedia of Biological Chemistry (Lennarz W J. Lane M D eds) Elsevier/Academic Press).

The PI3 kinase/Akt/PTEN pathway is an attractive target for cancer drug development since such agents would be expected to inhibit proliferation, reverse the repression of apoptosis and surmount resistance to cytotoxic agents in cancer cells. PI3 kinase inhibitors have been reported (Yaguchi et al (2006) Jour. of the Nat. Cancer Inst. 98(8):545-556; U.S. Pat. Nos. 7,173,029; 7,037,915; 6,608,056; 6,608,053; 6,838, 457; 6,770,641; 6,653,320; 6,403,588; WO 2004/017950; U.S. Pat. No 2004/092561; WO 2004/007491; WO 2004/ 006916; WO 2003/037886; U.S. Pat. No 2003/149074; WO 2003/035618; WO 2003/034997; US 2003/158212; EP 1417976; U.S. Pat. No 2004/053946; JP 2001247477; JP 08175990; JP 08176070).

SUMMARY OF THE INVENTION

The invention relates generally to thiazolopyrimidine compounds with anti-cancer activity, and more specifically with PI3 kinase inhibitory activity. Certain hyperproliferative disorders are characterized by the modulation of PI3 kinase function, for example by mutations or overexpression of the proteins. Accordingly, the compounds of the invention may be useful in the treatment of hyperproliferative disorders such as cancer. The compounds may inhibit tumor growth in mammals and may be useful for treating human cancer patients.

The invention also relates to methods of using the compounds for in vitro, in situ, and in vivo diagnosis or treatment of mammalian cells, organisms, or associated pathological conditions.

More specifically, one aspect of the invention provides 4-morpholino 4-(thiazolo[5,4-d]pyrimidin-7-yl)morpholine compounds of Formula Ia and 4-(thiazolo[4,5-d]pyrimidin-7-yl)morpholine compounds of Formula Ib:

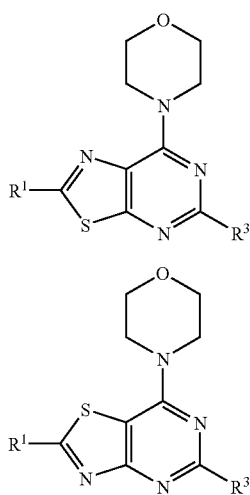

and stereoisomers, geometric isomers, tautomers, or pharmaceutically acceptable salts thereof, wherein $R^1$ and $R^3$ are as defined herein.

Another aspect of the invention provides a pharmaceutical composition comprising a compound of Formulas Ia or Ib and a pharmaceutically acceptable carrier, glidant, diluent, or excipient. The pharmaceutical composition may further comprise one or more additional therapeutic agents selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

Another aspect of the invention provides methods of inhibiting PI3 kinase activity, comprising contacting a PI3 kinase with an effective inhibitory amount of a compound of Formula Ia or Ib, or a stereoisomer, geometric isomer, tautomer, solvate, metabolite, or pharmaceutically acceptable salt or prodrug thereof.

Another aspect of the invention provides methods of preventing or treating a hyperproliferative disorder, comprising administering to a mammal in need of such treatment an effective amount of a compound of Formula Ia or Ib, or a stereoisomer, geometric isomer, tautomer, solvate, metabolite, or pharmaceutically acceptable salt or prodrug thereof, alone or in combination with one or more additional compounds having anti-hyperproliferative properties.

Another aspect the invention provides a method of using a compound of this invention to treat a disease or condition modulated by PI3 kinase in a mammal.

Another aspect of the invention is the use of a compound of this invention in the preparation of a medicament for the treatment or prevention of a disease or condition modulated by PI3 kinase in a mammal.

Another aspect of the invention includes kits comprising: (i) a compound of Formula Ia or Ib, or a stereoisomer, geometric isomer, tautomer, solvate, metabolite, or pharmaceutically acceptable salt or prodrug thereof, (ii) a container, and (iii) optionally a package insert or label indicating a treatment.

Another aspect of the invention includes methods of preparing, methods of separating, and methods of purifying compounds of Formula Ia and Ib.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, sp² double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, biphenyl, indenyl, indanyl, 1,2-dihydronapthalene, 1,2,3,4-tetrahydronapthyl, and the like. Aryl groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 20 or more ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. The term "heterocycle" includes heterocycloalkoxy. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco [3.1.0]hexanyl, 3-azabicyclo[4.1.0]heptanyl, azabicyclo [2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (═O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), nitrogen (nitrogen-linked) or oxygen (oxygen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "monocyclic heteroaryl" refers to a five- or six-membered, unsubstituted or substituted, monocyclic heteroaryl radical which contains 1, 2, 3 or 4 ring heteroatoms independently selected from N, O and S. The monocyclic heteroaryl is attached to the C-2 position of the pyrimidine ring according to Formulas Ia and Ib at any carbon (carbon-linked) atom of the monocyclic heteroaryl $R^3$ group. Monocyclic heteroaryl radicals include, but are not limited to: 2-pyridyl, 3-pyridyl, 4-pyridyl, 3-isoxazolyl, 4-isoxazolyl, 5-isoxazolyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl. Monocyclic heteroaryls are optionally substituted independently with one or more substituents described herein.

"Fused bicyclic $C_3$-$C_{20}$ heterocyclyl" and "Fused bicyclic $C_1$-$C_{20}$ heteroaryl" containing one or more heteroatoms independently selected from nitrogen, oxygen, and sulfur, differ only by their aromatic character, and have two rings fused together, i.e. share a common bond. Fused bicyclic heterocyclyl and heteroaryl radicals are attached to the C-2 position of the pyrimidine ring according to Formulas Ia and Ib at any carbon (carbon-linked) atom of the fused bicyclic $C_3$-$C_{20}$ heterocyclyl or fused bicyclic $C_1$-$C_{20}$ heteroaryl group $R^3$ group. Fused bicyclic heterocyclyl and heteroaryl radicals include, but are not limited to: 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 1H-pyrrolo[2,3-b]pyridine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, and pyrido[3,2-b]pyrazine. Fused bicyclic heterocycles and fused bicyclic heteroaryls are optionally substituted independently with one or more substituents described herein.

The substituent groups that alkyl, alkenyl, alkynyl, carbocyclyl, heterocyclyl, aryl, heteroaryl, fused bicyclic $C_3$-$C_{20}$ heterocyclyl, and fused bicyclic $C_1$-$C_{20}$ heteroaryl are optionally substituted with include F, Cl, Br, I, CN, $CF_3$, —$NO_2$, oxo, $R^{10}$, —C(=Y)$R^{10}$, —C(=Y)$OR^{10}$, —C(=Y)$NR^{10}R^{11}$, —$(CR^{14}R^{15})_n NR^{10}R^{11}$, —$(CR^{14}R^{15})_n OR^{10}$, $NR^{10}R^{11}$, —$NR^{12}C(=Y)R^{10}$, —$NR^{12}C(=Y)OR^{11}$, —$NR^{12}C(=Y)NR^{10}R^{11}$, —$NR^{12}SO_2R^{10}$, =$NR^{12}$, $OR^{10}$, —OC(=Y)$R^{10}$, —OC(=Y)$OR^{10}$, —OC(=Y)$NR^{10}R^{11}$, —$OS(O)_2(OR^{10})$, —OP(=Y)$(OR^{10})(OR^{11})$, —OP$(OR^{10})(OR^{11})$, $SR^{10}$, —S(O)$R^{10}$, —S(O)$_2R^{10}$, —S(O)$_2NR^{10}R^{11}$, —S(O)($OR^{10}$), —S(O)$_2(OR^{10})$, —SC(=Y)$R^{10}$, —SC(=Y)$OR^{10}$, —SC(=Y)$NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —$(CR^{14}R^{15})_t$—$NR^{12}C(=O)(CR^{14}R^{15})NR^{10}R^{11}$, and $(CR^4R^5)_t$—$NR^{10}R^{11}$ The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a Formula Ia or Ib compound that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular hyperproliferative disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sutent (SUNITINIB®, SU11248, Pfizer), letrozole (FEMARA®, Novartis), imatinib mesylate (GLEEVEC®, Novartis), PTK787/ZK 222584 (Novartis), oxaliplatin (ELOXATIN®, Sanofi), 5-FU (5-fluorouracil), Leucovorin, Rapamycin (sirolimus, RAPAMUNE®, Wyeth), lapatinib (TYKERB®, GSK572016, Glaxo Smith Kline), Lonafamib (SCH 66336), sorafenib (NEXAVAR®, BAY43-9006, Bayer Labs), and gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, calicheamicin gammaI1, calicheamicin omegaI1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL®, Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and doxetaxel (TAXOTERE®, Rhône-Poulenc Rorer, Antony, France); chloranmbucil; gemcitabine (GEMZAR®); 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the Formula Ia or Ib compound, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1′-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

The terms "compound of this invention," and "compounds of the present invention" and "compounds of Formula Ia and Ib" include compounds of Formulas Ia and Ib and stereoisomers, geometric isomers, tautomers, solvates, metabolites, and pharmaceutically acceptable salts and prodrugs thereof.

The term "mammal" includes, but is not limited to, humans, mice, rats, guinea pigs, monkeys, dogs, cats, horses, cows, pigs, and sheep, and poultry.

Thiazolopyrimidine PI3 Kinase Inhibitor Compounds

The present invention provides thiazolopyrimidine compounds, and pharmaceutical formulations thereof, that are potentially useful in the treatment of diseases, conditions and/or disorders modulated by PI3 kinases. The compounds may inhibit p110 isoforms including alpha, beta, gamma, and delta as pan inhibitors. The compounds may be p110 isoform selective inhibitors by selective inhibition of one of the p110 isoforms.

More specifically, the present invention provides 4-morpholino 4-(thiazolo[5,4-d]pyrimidin-7-yl)morpholine compounds of Formula Ia and 4-(thiazolo[4,5-d]pyrimidin-7-yl)morpholine compounds of Formula Ib:

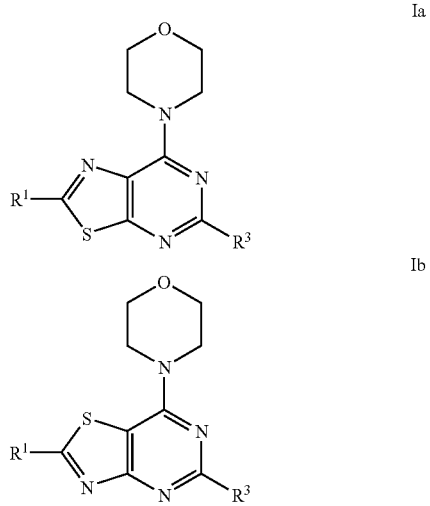

and stereoisomers, geometric isomers, tautomers, or pharmaceutically acceptable salts thereof, wherein:

$R^1$ is selected from H, F, Cl, Br, I, CN, —$(CR^{14}R^{15})_m$ $NR^{10}R^{11}$, —$C(R^{14}R^{15})_n NR^{12}C(=Y)R^{10}$, —$(CR^{14}R^{15})_n$ $NR^{12}S(O)_2R^{10}$, —$(CR^{14}R^{15})_m OR^{10}$, —$(CR^{14}R^{15})_n S(O)_2$ $R^{10}$, —$(CR^{14}R^{15})_n S(O)_2 NR^{10}R^{11}$, —$C(OR^{10})R^{11}R^{14}$, —C(=Y)R$^{10}$, —C(=Y)OR$^{10}$, —C(=Y)NR$^{10}$R$^{11}$, —C(=Y)NR$^{12}$OR$^{10}$, —C(=O)NR$^{12}$S(O)$_2$R$^{10}$, —C(=O)NR$^{12}$(CR$^{14}$R$^{15}$)$_m$NR$^{10}$R$^{11}$, —NO$_2$, —NR$^{12}$C(=Y)R$^{11}$, —NR$^{12}$C(=Y)OR$^{11}$, —NR$^{12}$C(=Y)NR$^{10}$R$^{11}$, —NR$^{12}$S(O)$_2$R$^{10}$, —NR$^{12}$SO$_2$NR$^{10}$R$^{11}$, —SR$^{10}$, —S(O)$_2$R$^{10}$, —S(O)$_2$NR$^{10}$R$^{11}$, —SC(=Y)R$^{10}$, —SC(=Y)OR$^{10}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

R$^3$ is a carbon linked monocyclic heteroaryl, a carbon linked fused bicyclic C$_3$-C$_{20}$ heterocyclyl, or a carbon linked fused bicyclic C$_1$-C$_{20}$ heteroaryl, where the monocyclic heteroaryl, fused bicyclic C$_3$-C$_{20}$ heterocyclyl, and fused bicyclic C$_1$-C$_{20}$ heteroaryl are optionally substituted with one or more groups selected from F, Cl, Br, I, —CN, —NR$^{10}$R$^{11}$, —OR$^{10}$, —C(O)R$^{10}$, —NR$^{10}$C(O)R$^{11}$, —N(C(O)R$^{11}$)$_2$, —NR$^{10}$C(O)NR$^{10}$R$^{11}$, —NR$^{12}$S(O)$_2$R$^{10}$, C(=O)OR$^{10}$, —C(=O)NR$^{10}$R$^{11}$, C$_1$-C$_{12}$ alkyl and (C$_1$-C$_{12}$ alkyl)-OR$^{10}$;

R$^{10}$, R$^{11}$ and R$^{12}$ are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R$^{10}$ and R$^{11}$ together with the nitrogen to which they are attached form a C$_2$-C$_{20}$ heterocyclic ring optionally substituted with one or more groups independently selected from oxo, (CH$_2$)$_m$OR$^{12}$, NR$^{12}$R$^{12}$, CF$_3$, F, Cl, Br, I, SO$_2$R$^{12}$, C(=O)R$^{12}$, NR$^{12}$C(=Y)R$^{12}$, NR$^{12}$S(O)$_2$R$^{12}$, C(=Y)NR$^{12}$R$^{12}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R$^{14}$ and R$^{15}$ are independently selected from H, C$_1$-C$_{12}$ alkyl, or —(CH$_2$)$_n$-aryl, or R$^{14}$ and R$^{15}$ together with the atoms to which they are attached form a saturated or partially unsaturated C$_3$-C$_{12}$ carbocyclic ring;

where said alkyl, alkenyl, alkynyl, carbocyclyl, heterocyclyl, aryl, and heteroaryl, are optionally substituted with one or more groups independently selected from F, Cl, Br, I, CN, CF$_3$, —NO$_2$, oxo, R$^{10}$, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$OR$^{10}$, —NR$^{10}$R$^{11}$, —NR$^{12}$C(=Y)R$^{10}$, —NR$^{12}$C(=Y)OR$^{11}$, —NR$^{12}$C(=Y)NR$^{10}$R$^{11}$, —(CR$^{14}$R$^{15}$)$_m$NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), —SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

Y is O, S, or NR$^{12}$;

m is 0, 1, 2, 3, 4, 5 or 6; and n is 1, 2, 3, 4, 5 or 6;

with the proviso that, when R$^1$ is —(CR$^{14}$R$^{15}$)$_m$NR$^{10}$R$^{11}$ in which R$^{14}$ and R$^{15}$ are independently selected from H or C$_1$-C$_6$ alkyl, m is 0, 1 or 2, and R$^{10}$ and R$^{11}$ together with the nitrogen to which they are attached form a nitrogen-containing heterocyclic ring having 3 to 20 ring atoms, the ring being optionally substituted as defined above, then R$^3$ is not an indole group which is unsubstituted or substituted.

Formula Ia and Ib compounds are regioisomers, i.e. differ by the placement of sulfur and nitrogen in the thiazole ring system. Parent molecules of Formula Ia and Ib compounds are:

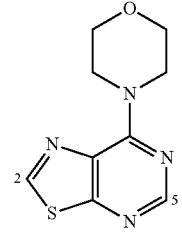

4-(thiazolo[5,4-d]pyrimidin-7-yl)morpholine

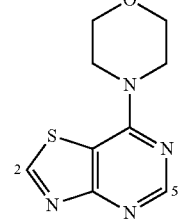

4-(thiazolo[4,5-d]pyrimidin-7-yl)morpholine

The compound of claim 1 wherein R$^1$ is —(CR$^{14}$R$^{15}$)$_m$NR$^{10}$R$^{11}$ where m is 1, and R$^{10}$ and R$^{11}$ together with the nitrogen to which they are attached form a C$_2$-C$_{20}$ heterocyclic ring selected from morpholinyl, piperidinyl, piperazinyl, and pyrrolidinyl. The C$_2$-C$_{20}$ heterocyclic ring may be substituted with one or more groups selected from NR$^{12}$R$^{12}$, CF$_3$, F, Cl, Br, I, SO$_2$R$^{12}$, C(=O)R$^{12}$, NR$^{12}$C(=Y)R$^{12}$, NR$^{12}$S(O)$_2$R$^{12}$, C(=Y)NR$^{12}$R$^{12}$, and C$_1$-C$_{12}$ alkyl In certain embodiments, R$^1$ is —(CR$^{14}$R$^{15}$)$_n$NR$^{12}$S(O)$_2$R$^{10}$ where n is 1 or 2; R$^{12}$, R$^{14}$, and R$^{15}$ are independently selected from H and C$_1$-C$_{12}$ alkyl; and R$^{10}$ is C$_1$-C$_{12}$ alkyl or C$_6$-C$_{20}$ aryl.

In certain embodiments, R$^1$ is —(CR$^{14}$R$^{15}$) OR$^{10}$ where n is 1 or 2, and R$^{10}$, R$^{14}$, and R$^{15}$ are independently selected from H and C$_1$-C$_{12}$ alkyl.

In certain embodiments, R$^1$ is —(CR$^{14}$R$^{15}$)$_n$S(O)$_2$R$^{10}$ where n is 1 or 2, and R$^{14}$ and R$^{15}$ are each H. R$^{10}$ may be C$_1$-C$_{12}$ alkyl or C$_6$-C$_{20}$ aryl.

In certain embodiments, R$^1$ is —(CR$^{14}$R$^{15}$)$_n$S(O)$_2$NR$^{10}$R$^{11}$ where n is 1 or 2, and R$^{14}$ and R$^{15}$ are H.

In certain embodiments, R$^1$ is —C(=Y)NR$^{10}$R$^{11}$ where Y is O, and R$^{10}$ and R$^{11}$ together with the nitrogen to which they are attached form the C$_2$-C$_{20}$ heterocyclic ring. R$^{10}$ and R$^{11}$ together with the nitrogen to which they are attached may form a C$_2$-C$_{20}$ heterocyclic ring selected from morpholinyl, piperidinyl, piperazinyl, and pyrrolidinyl.

In certain embodiments, R$^1$ is —C(=Y)NR$^{10}$R$^{11}$ where Y is O, and R$^{10}$ and R$^{11}$ are independently selected from H and C$_1$-C$_{12}$ alkyl.

In certain embodiments, R$^1$ is —C(=Y)NR$^{10}$R$^{11}$ where Y is O, and R$^{10}$ and R$^{11}$ are independently selected from H, C$_3$-C$_{12}$ carbocyclyl, C$_2$-C$_{20}$ heterocyclyl, C$_6$-C$_{20}$ aryl, and C$_1$-C$_{20}$ heteroaryl.

In certain embodiments, R$^1$ is —NHR$^{12}$ where R$^{12}$ is C$_3$-C$_{12}$ carbocyclyl, C$_2$-C$_{20}$ heterocyclyl, C$_6$-C$_{20}$ aryl, or C$_1$-C$_{20}$ heteroaryl. R$^{12}$ may be phenyl or 4-pyridyl.

In certain embodiments, R$^1$ is —NR$^{12}$C(=Y)R$^{11}$ where Y is O, R$^{12}$ is H or C$_1$-C$_{12}$ alkyl, and R$^{11}$ is C$_1$-C$_{12}$ alkyl, C$_3$-C$_{12}$ carbocyclyl, C$_2$-C$_{20}$ heterocyclyl, C$_6$-C$_{20}$ aryl, or C$_1$-C$_{20}$ heteroaryl. R$^{11}$ includes, but is not limited to, methyl, ethyl, propyl, isopropyl, isobutyl, 2,2-dimethylpropyl, and tert-butyl. R$^{11}$ also includes, but is not limited to, cyclopropyl, cyclobutyl, cyclopentyl, and cyclohexyl.

In certain embodiments, $R^1$ is —$NR^{12}S(O)_2R^{10}$ where $R^{12}$ is H or $C_1$-$C_{12}$ alkyl, and $R^{10}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl.

In certain embodiments, $R^1$ is $S(O)_2NR^{10}R^{11}$ where $R^{10}$ and $R^{11}$ together with the nitrogen to which they are attached form a $C_2$-$C_{20}$ heterocyclic ring selected from morpholinyl, piperidinyl, piperazinyl, and pyrrolidinyl.

In certain embodiments, $R^1$ is $S(O)_2NR^{10}R^{11}$ where $R^{10}$ and $R^{11}$ are independently selected from H and $C_1$-$C_{12}$ alkyl. $R^{10}$ and $R^{11}$ may be independently selected from H, substituted ethyl, and substituted propyl.

In certain embodiments, $R^1$ is $C_2$-$C_{12}$ alkyl.

In certain embodiments, $R^1$ is $C_2$-$C_8$ alkenyl.

In certain embodiments, $R^1$ is $C_2$-$C_8$ alkynyl. The $C_2$-$C_8$ alkynyl may be substituted with $C_2$-$C_{20}$ heterocyclyl, which includes, but is not limited to, morpholinyl, piperidinyl, piperazinyl, and pyrrolidinyl.

In certain embodiments, $R^1$ is selected from the groups:

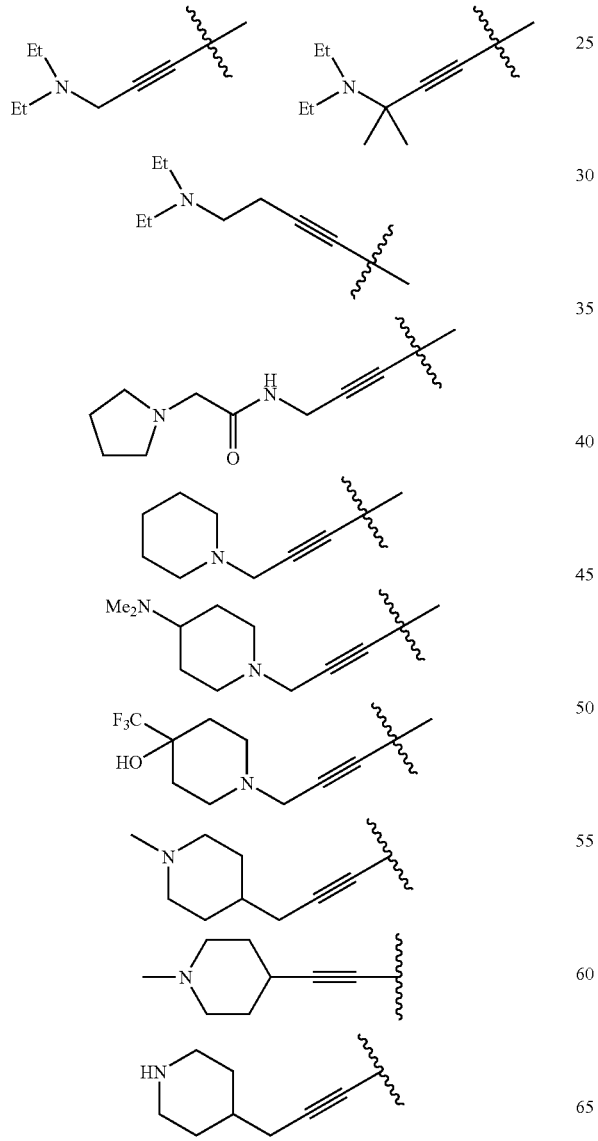
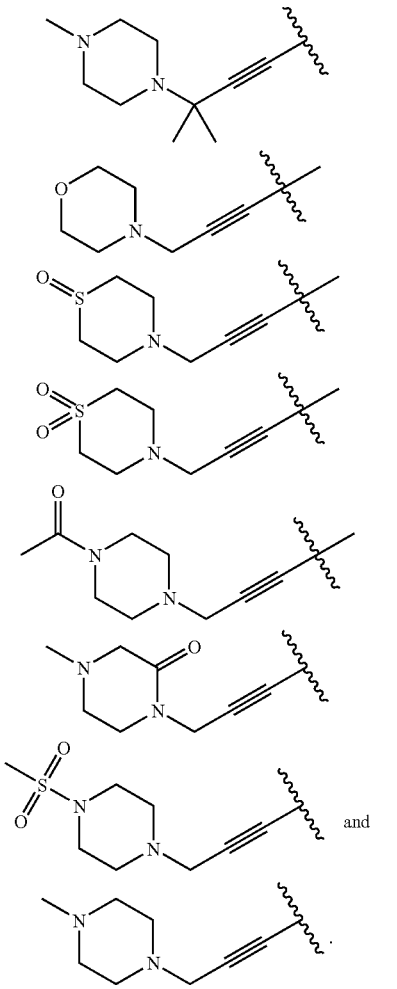

In certain embodiments, $R^1$ is $C_6$-$C_{20}$ aryl, such as phenyl.

In certain embodiments, $R^1$ is $C_3$-$C_{12}$ carbocyclyl.

In certain embodiments, $R^1$ is $C_2$-$C_{20}$ heterocyclyl.

In certain embodiments, $R^1$ is $C_1$-$C_{20}$ heteroaryl, such as 2-pyridyl, 3-pyridyl, 4-pyridyl, or 5-pyrimidinyl.

In certain embodiments, $R^3$ is a carbon linked monocyclic heteroaryl selected from the structures:

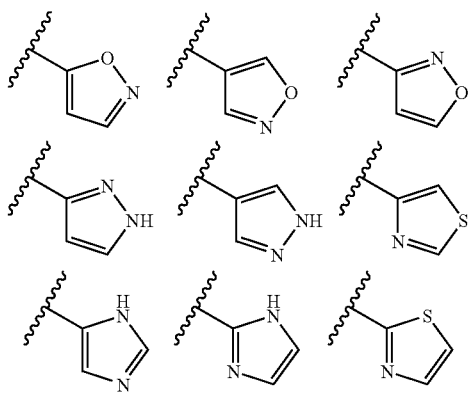

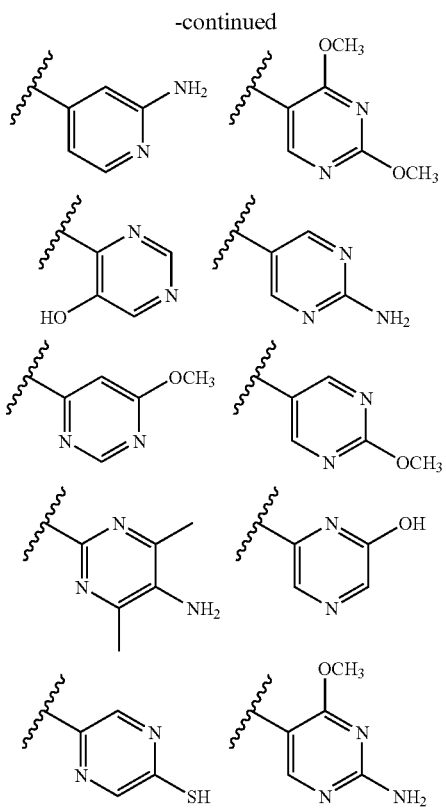

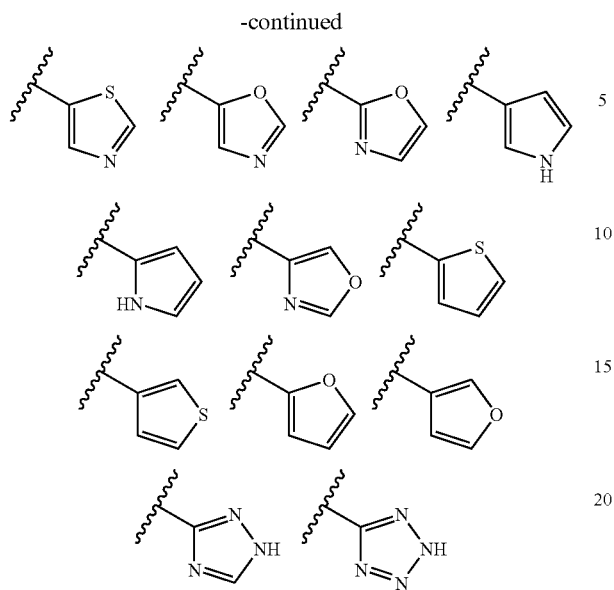

where the monocyclic heteroaryl group is optionally substituted with one or more groups selected from F, Cl, Br, I, —NR$^{10}$R$^{11}$, —OR$^{10}$, —C(O)R$^{10}$, —NR$^{10}$C(O)R$^{11}$, —N(C(O)R$^{11}$)$_2$, —NR$^{10}$C(O)NR$^{10}$R$^{11}$, —C(=O)OR$^{10}$, —C(=O)NR$^{10}$R$^{11}$, and C$_1$-C$_{12}$ alkyl.

In certain embodiments, R$^3$ is a carbon linked monocyclic heteroaryl selected from the structures:

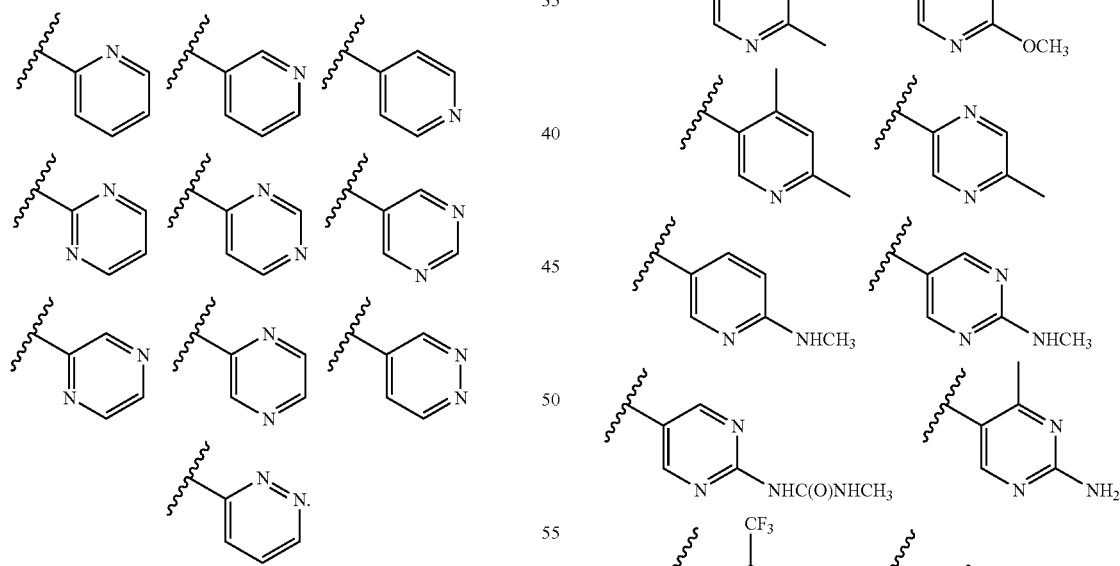

In certain embodiments, R$^3$ is selected from the structures:

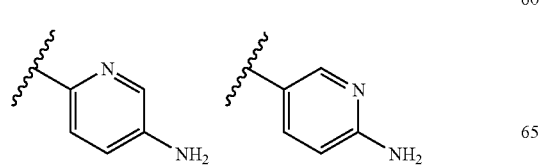

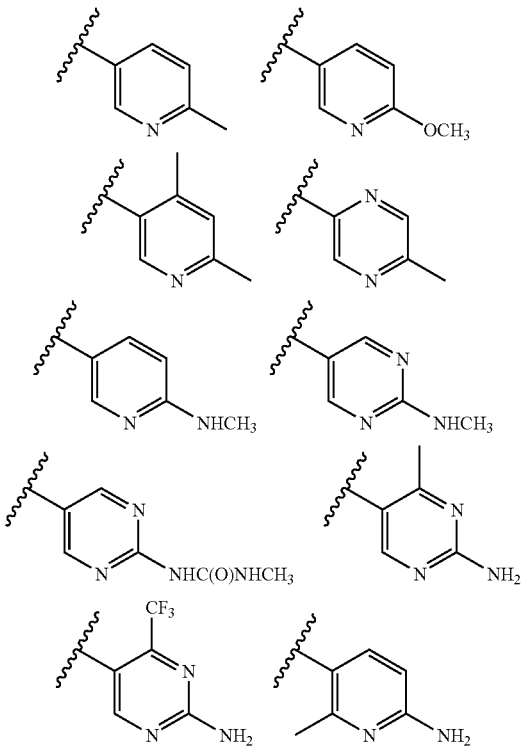

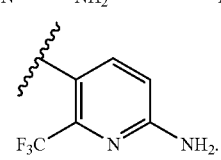

In certain embodiments, the monocyclic heteroaryl group is substituted with one or more groups selected from F, —CF$_3$, —NH$_2$, —NHCH$_3$, —N(CH$_3$)$_2$, —OH, —OCH$_3$, —C(O)CH$_3$, —NHC(O)CH$_3$, —N(C(O)CH$_3$)$_2$, —NHC(O)NH$_2$, —CO$_2$H, —CHO, —CH$_2$OH, —C(=O)NHCH$_3$, —C(=O)NH$_2$, and —CH$_3$.

Exemplary embodiments of R$^3$ include, but are not limited to: 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, and pyrido[3,2-b]pyrazine.

The attachment site of the R$^3$ group to the C-2 position of the pyrimidine ring according to Formulas Ia and Ib may be at any carbon (carbon-linked) atom of the fused bicyclic C$_3$-C$_{20}$ heterocyclyl or fused bicyclic C$_1$-C$_{20}$ heteroaryl group R$^3$ group.

Exemplary embodiments of R$^3$ include the following groups, where the wavy line indicates the site of attachment to the pyrimidine ring:

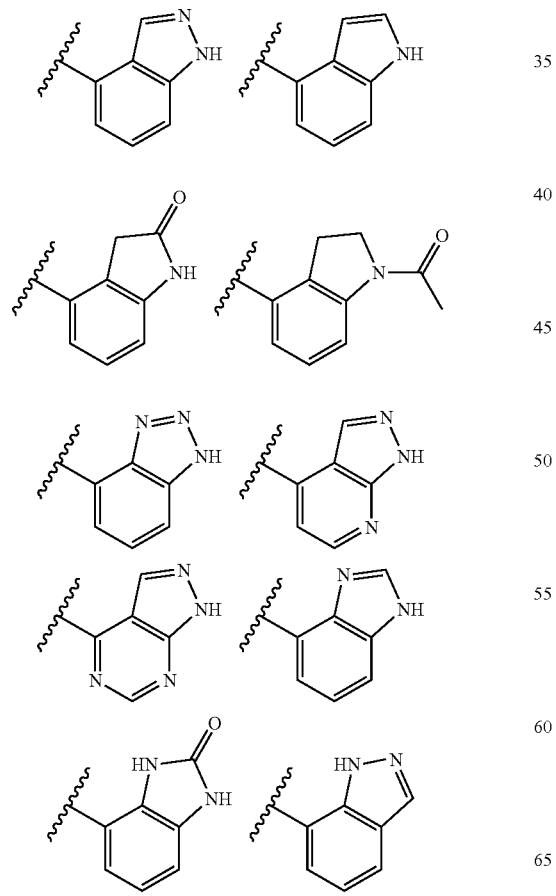

-continued

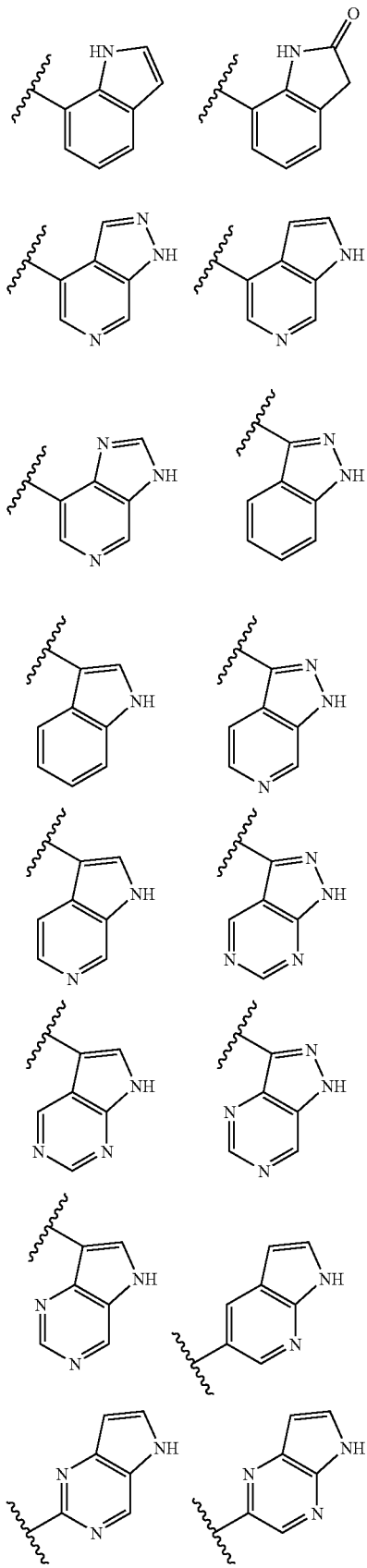

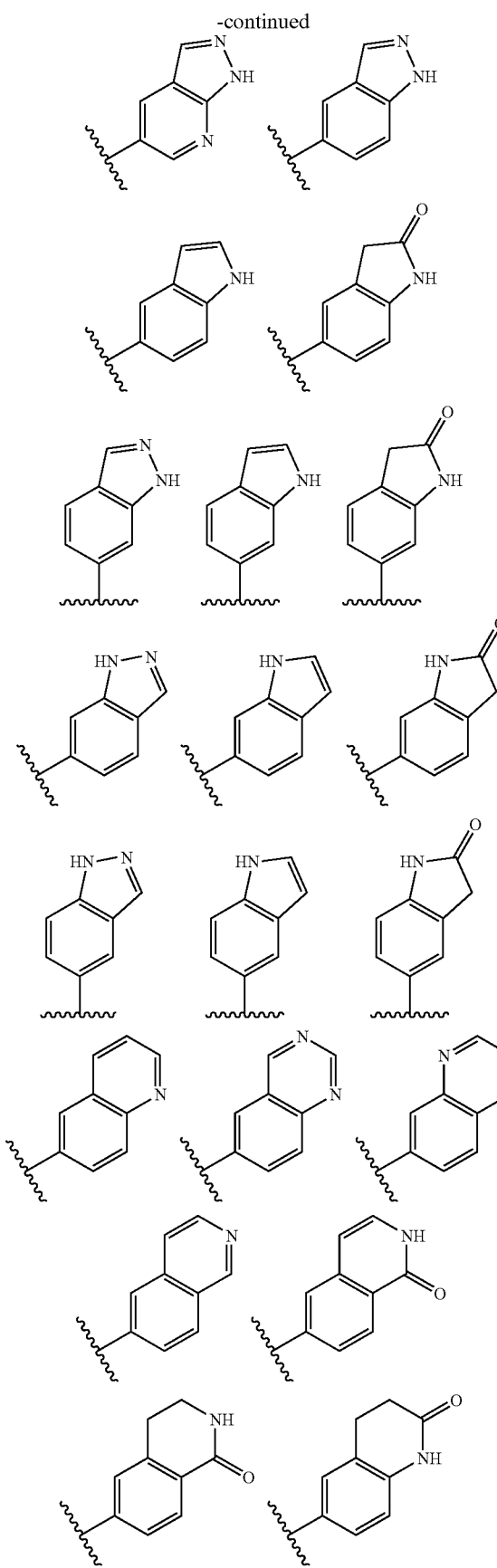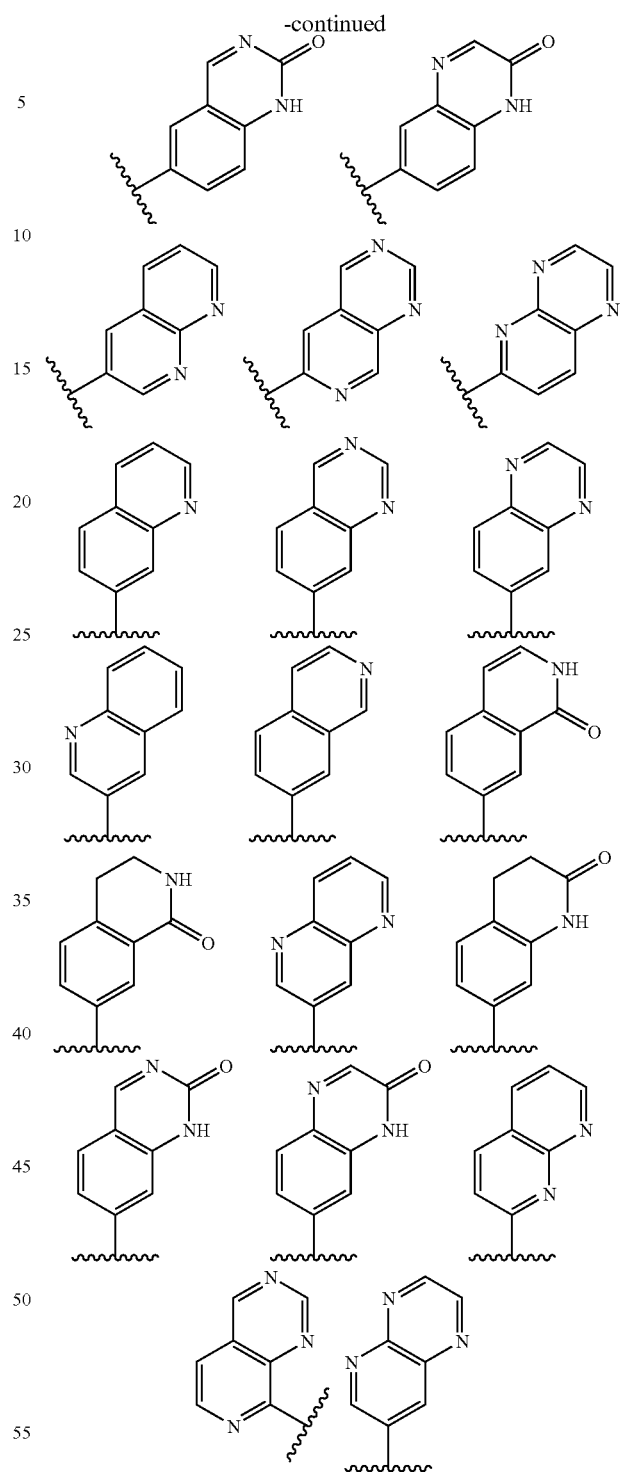

where the wavy line indicates the site of attachment.

Exemplary embodiments of $R^3$ include fused bicyclic $C_3$-$C_{20}$ heterocyclyl and fused bicyclic $C_1$-$C_{20}$ heteroaryl, including those exemplified above, substituted with one or more groups independently selected from F, Cl, Br, I, CN, $CF_3$, $-NO_2$, oxo, $-C(=Y)R^{10}$, $-C(=Y)OR^{10}$, $-C(=Y)NR^{10}R^{11}$, $-(CR^{14}R^{15})_nNR^{10}R^{11}$, $-(CR^{14}R^{15})_nOR^{10}$, $-NR^{10}R^{11}$, $-NR^{12}C(=Y)R^{10}$, $-NR^{12}C(=Y)OR^{11}$, $-NR^{12}C(=Y)NR^{10}R^{11}$, $-NR^{12}SO_2R^{10}$, $=NR^{12}$, $OR^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, C$_1$-C$_{20}$ heteroaryl, —(CR$^{14}$R$^{15}$)$_r$—NR$^{12}$C(=O)(CR$^{14}$R$^{15}$)NR$^{10}$R$^{11}$, and (CR$^4$R$^5$)$_r$—NR$^{10}$R$^{11}$.

In certain embodiments, R$^3$ is not an indole group which is unsubstituted or substituted.

Formula Ia and Ib compounds may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, Formula Ia and Ib compounds embrace all geometric and positional isomers. For example, if a Formula Ia and Ib compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

Formula Ia and Ib compounds may exist in unsolvated as well as solvated forms with pharmaceutically acceptable solvents such as water, ethanol, and the like, and it is intended that the invention embrace both solvated and unsolvated forms.

Formula Ia and Ib compounds may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled Formula Ia and Ib compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled Formula Ia or Ib compounds (e.g., those labeled with $^3$H and $^{14}$C) are useful in compound and/or substrate tissue distribution assays. Tritiated (3H) and carbon-14 ($^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled Formula Ia or Ib compounds can generally be prepared by following procedures analogous to those disclosed in the Schemes and/or in the Examples herein below, by substituting an isotopically labeled reagent for a non-isotopically labeled reagent.

Preparation of Formula Ia and Ib Compounds

Formula Ia and Ib compounds may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

In certain embodiments, compounds of Formula Ia or Ib may be readily prepared using procedures well-known to prepare thiazoles, pyrimidines, and thiazolopyrimidines (U.S. Pat. Nos. 6,608,053; 6,492,383; 6,232,320; 6,187,777; 3,763,156; 3,661,908; 3,475,429; 5,075,305; 2003/220365; GB 1390658; GB 1393161; WO 93/13664;); and other heterocycles, which are described in: Comprehensive Heterocyclic Chemistry, Editors Katritzky and Rees, Pergamon Press, 1984.

Compounds of Formula Ia and Ib may be prepared singly or as compound libraries comprising at least 2, for example 5 to 1,000 compounds, or 10 to 100 compounds. Libraries of compounds of Formula Ia or Ib may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, Schemes 1-7 show general methods for preparing Formula Ia and Ib compounds as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing Formula Ia and Ib compounds, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

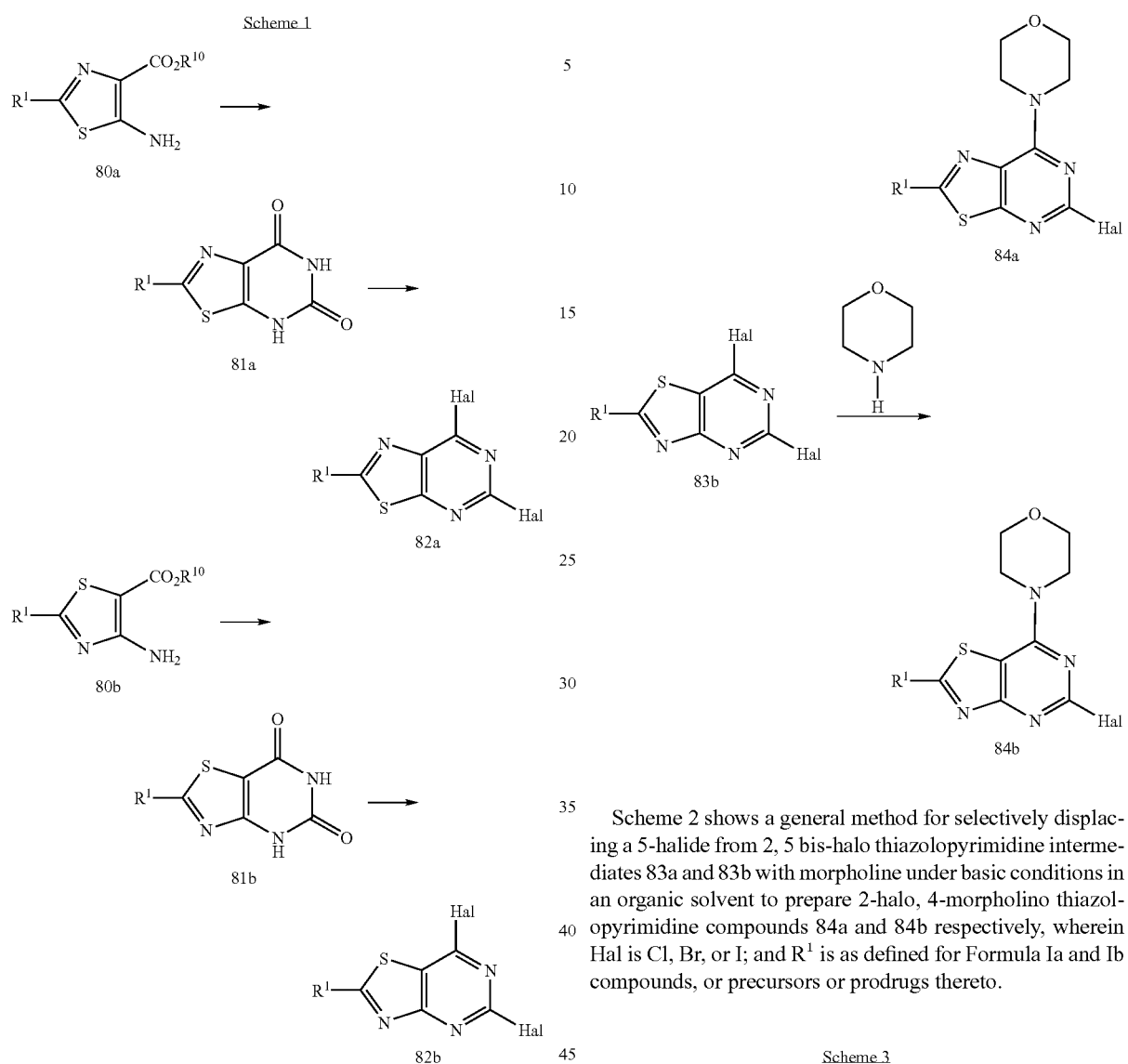

Scheme 1 shows a general method for preparation of the thiazolo[5,4-d]pyrimidine 82a and thiazolo[4,5-d]pyrimidine intermediates 82b from 3-carboxyester, 2-aminothiazoles 80a, and 3-amino, 2-carboxy ester thiazoles 80b, wherein Hal is Cl, Br, or I; and $R^1$ and $R^{10}$ are as defined for Formula Ia and Ib compounds, or precursors or prodrugs thereto.

Scheme 2 shows a general method for selectively displacing a 5-halide from 2, 5 bis-halo thiazolopyrimidine intermediates 83a and 83b with morpholine under basic conditions in an organic solvent to prepare 2-halo, 4-morpholino thiazolopyrimidine compounds 84a and 84b respectively, wherein Hal is Cl, Br, or I; and $R^1$ is as defined for Formula Ia and Ib compounds, or precursors or prodrugs thereto.

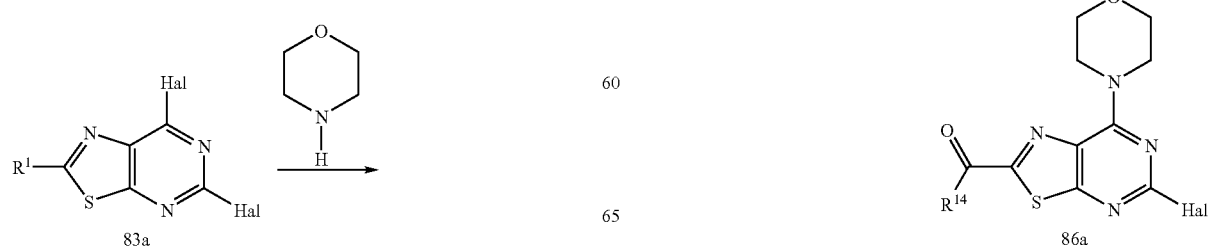

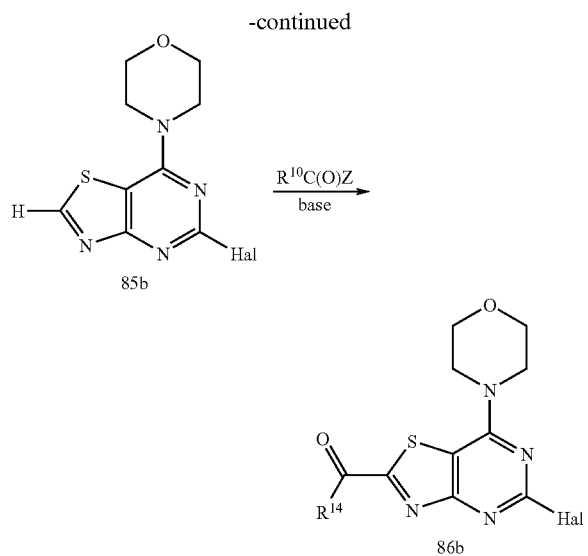

Scheme 3 shows a general method for derivatizing the 2-position of 5-halo, 7-morpholino, where 2-hydrogen thiazolopyrimidine compounds 85a and 85b ($R^1$ is H). Treating 85a or 85b with a lithiating reagent to remove the 2 position proton, followed by adding an acylating reagent $R^{10}C(O)Z$ where Z is a leaving group, such as halide, NHS ester, carboxylate, or dialkylamino, gives 5-halo, 7-morpholino, 2-acyl thiazolopyrimidine compounds 86a and 86b, wherein Hal is Cl, Br, or I; and $R^{10}$ is as defined for Formula Ia and Ib compounds, or precursors or prodrugs thereto. An example of $R^{10}C(O)Z$ to prepare 2-formyl compounds ($R^{10}$=H) is N,N'-dimethylformamide (DMF).

Scheme 4

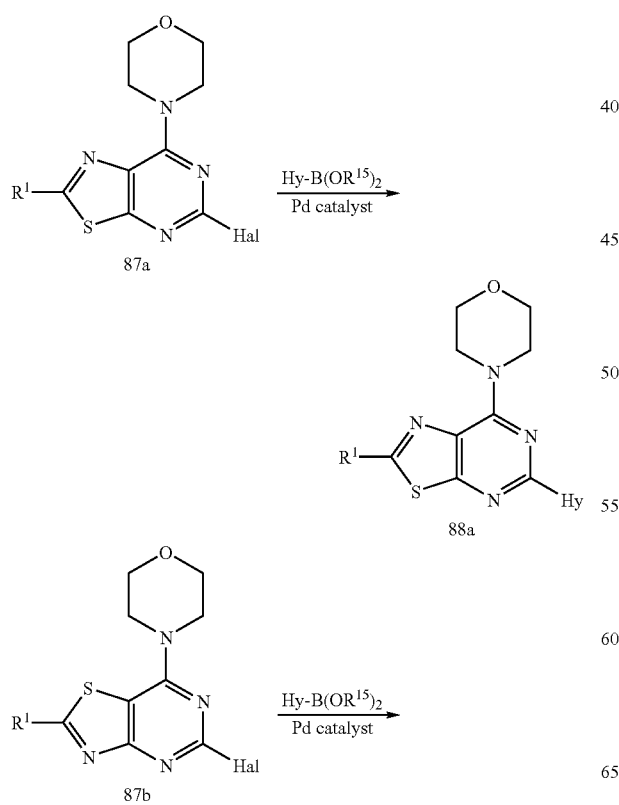

Scheme 4 shows a general method for Suzuki-type coupling of a 5-halo thiazolopyrimidine intermediates (87a and 87b) with a monocyclic heteroaryl, fused bicyclic heterocycle or fused bicyclic heteroaryl boronate acid ($R^{15}$=H) or ester ($R^{15}$=alkyl) reagent (Hy-B(OR$^{15}$)$_2$) to prepare the 5-monocyclic heteroaryl, 5-fused bicyclic heterocycle or 5-fused bicyclic heteroaryl (Hy), 7-morpholino thiazolopyrimidine compounds (88a and 88b) of Formulas Ia and Ib wherein Hal is Cl, Br, or I; and $R^1$ is as defined for Formula Ia and Ib compounds, or precursors or prodrugs thereto. For reviews of the Suzuki reaction, see: Miyaura et al. (1995) Chem. Rev. 95:2457-2483; Suzuki, A. (1999) J. Organomet. Chem. 576: 147-168; Suzuki, A. in Metal-Catalyzed Cross-Coupling Reactions, Diederich, F., Stang, P. J., Eds., VCH, Weinheim, D E (1998), pp 49-97. The palladium catalyst may be any that is typically used for Suzuki-type cross-couplings, such as PdCl$_2$(PPh$_3$)$_2$, Pd(PPh$_3$)$_4$, Pd(OAc)$_2$, PdCl$_2$(dppf)-DCM, Pd$_2$(dba)$_3$/Pt-Bu)$_3$ (Owens et al (2003) Bioorganic & Med. Chem. Letters 13:4143-4145; Molander et al (2002) Organic Letters 4(11):1867-1870; U.S. Pat. No. 6,448,433).

Generally, a Formula Ia or Formula Ib compound may be prepared by a method comprising reacting a Formula IIa or Formula IIb compound:

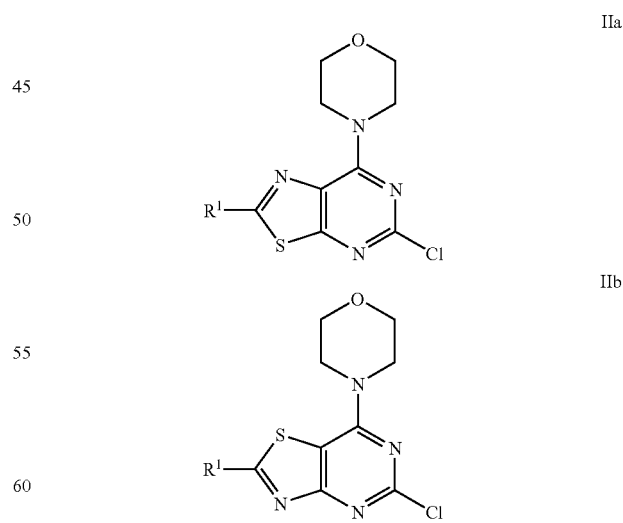

with a boronate compound comprising a monocyclic heteroaryl, a fused bicyclic heterocycle, or a fused bicyclic heteroaryl, whereby a Formula Ia and Formula Ib compound is formed.

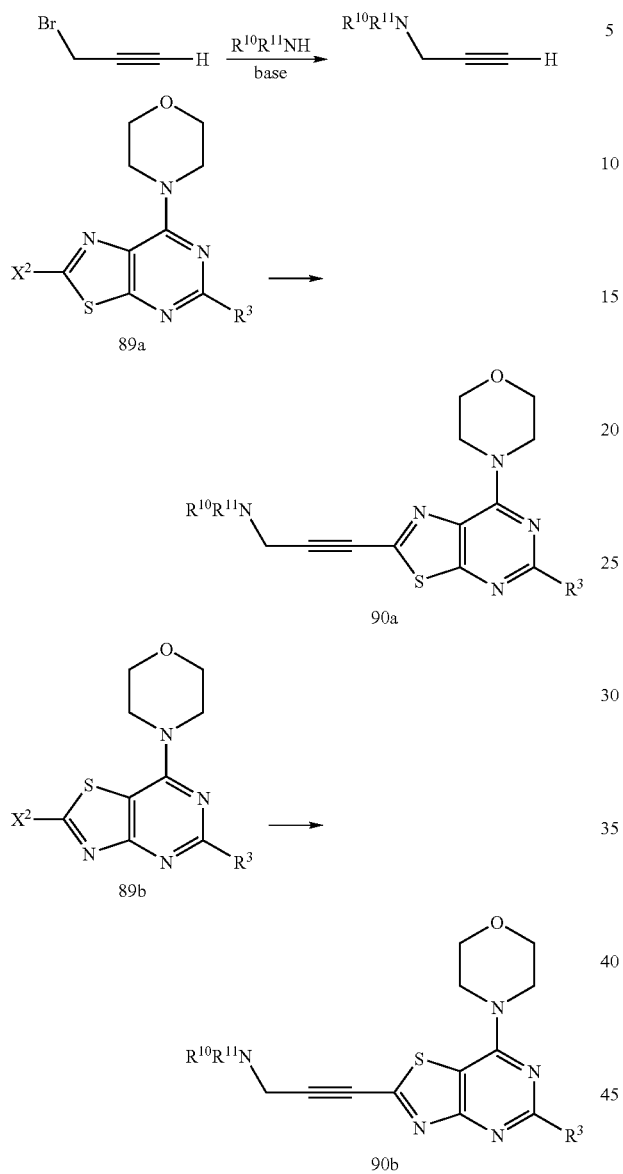

Scheme 5 shows a general method to prepare alkynylated compounds 90a and 90b. Propargylic amines may be prepared by reaction of propargyl bromide with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of an appropriate base ($Cs_2CO_3$ or the like). For reviews of alkynyl amines and related syntheses see Booker-Milburn, K. I., *Comprehensive Organic Functional Group Transformations* (1995), 2:1039-1074; and Viehe, H. G., (1967) Angew. Chem., Int. Ed. Eng., 6(9):767-778. Alkynes may subsequently be reacted with intermediates 89a or 89b ($X^2$=bromo or iodo) via Sonogashira coupling, to provide alkynylated compounds 90a and 90b, respectively, wherein $R^3$ is as defined for Formula Ia and Ib compounds, or precursors or prodrugs thereto.

Scheme 6 shows a general method for the synthesis of alkynylated compounds 92a and 92b. Gem-dialkyl propargylic amines may be prepared using methods described in Zaragoza et al. (2004) J. Med. Chem. 47:2833. Gem-dialkyl chlorides ($R^{14}$ and $R^{15}$ are independently methyl, ethyl or other alkyl group) can be reacted with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of CuCl and an appropriate base (e.g. TEA or the like) to provide the propargylic alkyne. The propargylic alkyne can be reacted with intermediates 91a or 91b via Sonogashira coupling to provide compounds 92a and 92b, respectively, wherein $R^3$ is as defined for Formula Ia and Ib compounds, or precursors or prodrugs thereto.

Scheme 7

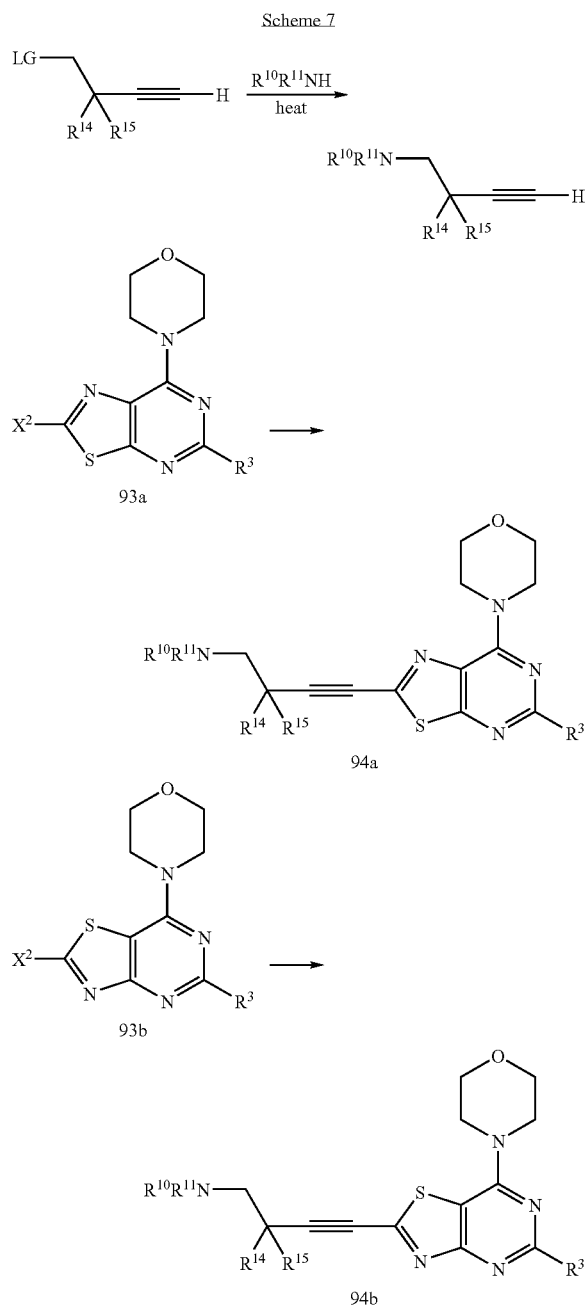

Scheme 7 shows a general scheme to prepare butynylated compounds 94a and 94b. But-3-yn-1-amines (wherein $R^{14}$ and $R^{15}$ are independently H, alkyl, aryl, heteroaryl, or $R^{14}$ and $R^{15}$ together with the carbon atom to which they are attached form a carbocyclic or heterocyclic ring) can be prepared from reaction of alkynes (LG=tosylate or other leaving group) with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) using the protocol described by Olomucki M. et al (1960) Ann. Chim. 5:845. But-3-yn-1-amines can subsequently be reacted with intermediates 93a or 93b via Sonogashira coupling, according to the descriptions provided for Schemes 5 and 6 to provide compounds 94a and 94b, respectively, wherein $R^3$ is as defined for Formula Ia and Ib compounds, or precursors or prodrugs thereto.

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the Formula Ia and Ib compounds may be atropisomers and are considered part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III (1982) J. Org. Chem. 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Biological Evaluation

Determination of the activity of PI3 kinase activity of a compound of Formula Ia or Ib is possible by a number of direct and indirect detection methods. Certain exemplary compounds described herein were prepared, characterized, and assayed for their PI3K binding activity (Examples 73 and 74) and in vitro activity against tumor cells (Example 75). The range of PI3K binding activities was less than 1 mM (nanomolar) to about 10 μM (micromolar). Certain exemplary compounds of the invention had PI3K binding activity $IC_{50}$ values less than 10 nM. Certain compounds of the invention had tumor cell-based activity $IC_{50}$ values less than 100 nM.

The Formula Ia and Ib compounds may inhibit p110 catalytic subunit isoforms including alpha, beta, gamma, and delta as pan inhibitors. Certain Formula Ia and Ib compounds may be p110 isoform selective inhibitors by selectively inhibiting one of one of the p110 isoforms; alpha, beta, gamma, or delta. One embodiment of the invention is a Formula Ia or Ib compound which is a p110 alpha selective inhibitor. A p110 selective inhibitor may mitigate the risk of toxicity due to potential toxicities associated with inhibiting the other p110 isoforms. Certain Formula Ia and Ib compounds may be p110 isoform pan inhibitors by possessing significant binding to two or more of the p110 isoforms. One embodiment of the invention is a Formula Ia or Ib compound which is a pan inhibitor of PI3K.

Binding of Formula Ia and Ib compounds from Table 1 to purified preparations of p110 isoforms alpha, beta, delta, and gamma was measured by a Scintillation Proximity Assay (SPA) to determine binding activity ($IC_{50}$ μMol) and selectivity of binding of beta, delta, and gamma isoforms relative to alpha (Example 74).

The cytotoxic or cytostatic activity of Formula Ia and Ib exemplary compounds was measured by: establishing a proliferating mammalian tumor cell line in a cell culture medium, adding a Formula Ia or Ib compound, culturing the cells for a period from about 6 hours to about 5 days; and measuring cell viability (Example 75). Cell-based in vitro assays were used to measure viability, i.e. proliferation ($IC_{50}$), cytotoxicity ($EC_{50}$), and induction of apoptosis (caspase activation).

The in vitro potency of Formula Ia and Ib exemplary compounds was measured by the cell proliferation assay, CellTiter-Glo® Luminescent Cell Viability Assay, commercially available from Promega Corp., Madison, Wis. (Example 75) against several tumor cell lines, including PC3, Detroit 562, and MDAMB361.1. $EC_{50}$ values were established for the tested compounds. The range of in vitro cell potency activities was about 100 nM to about 10 μM. This homogeneous assay method is based on the recombinant expression of *Coleoptera luciferase* (U.S. Pat. Nos. 5,583,024; 5,674,713; 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Gloo Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system can detect as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

Certain ADME properties were measured for certain exemplary compounds by assays including: Caco-2 Permeability (Example 76), Hepatocyte Clearance (Example 77), Cytochrome P450 Inhibition (Example 78), Cytochrome P450 Induction (Example 79), Plasma Protein Binding (Example 80), and HERG channel blockage (Example 81).

Exemplary Formula Ia and Ib compounds No. 101-147 which were made according to the methods of this invention include the following structures and their corresponding names (ChemDraw Ultra, CambridgeSoft Corp., Cambridge Mass.) in Table 1.

TABLE 1

| No. | Structure | Name |
|---|---|---|
| 101. | 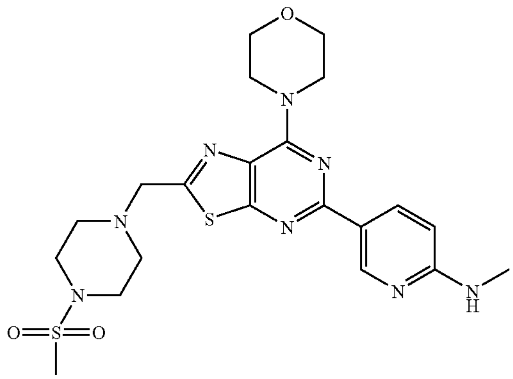 | N-methyl-5-(2-((4-(methylsulfonyl)piperazin-1-yl)methyl)-7-morpholinothiazolo[5,4-d]pyrimidin-5-yl)pyridin-2-amine |
| 102. | 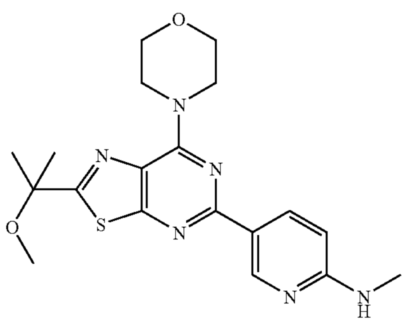 | 5-(2-(2-methoxypropan-2-yl)-7-morpholinothiazolo[5,4-d]pyrimidin-5-yl)-N-methylpyridin-2-amine |
| 103. | 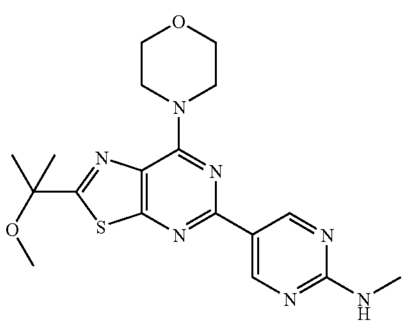 | 5-(2-(2-methoxypropan-2-yl)-7-morpholinothiazolo[5,4-d]pyrimidin-5-yl)-N-methylpyrimidin-2-amine |
| 104. | 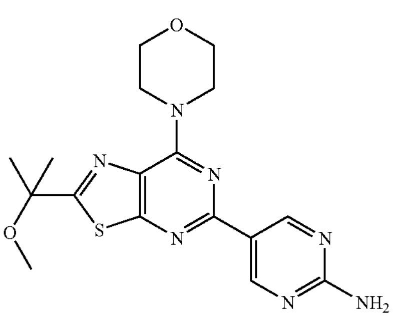 | 5-(2-(2-methoxypropan-2-yl)-7-morpholinothiazolo[5,4-d]pyrimidin-5-yl)pyrimidin-2-amine |

TABLE 1-continued

| No. | Structure | Name |
|---|---|---|
| 105. | 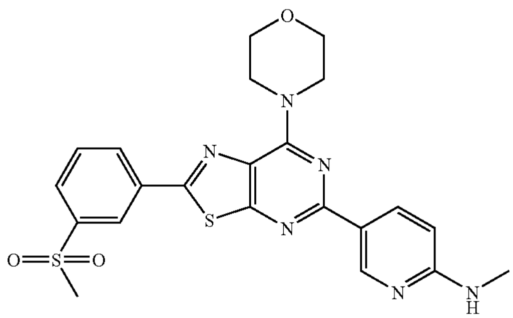 | N-methyl-5-(2-(3-(methylsulfonyl)phenyl)-7-morpholinothiazolo[5,4-d]pyrimidin-5-yl)pyridin-2-amine |
| 106. | 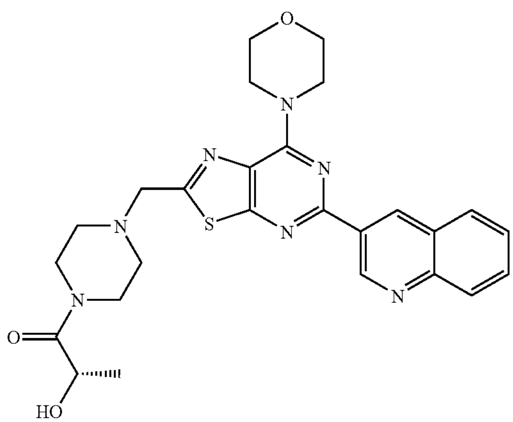 | (S)-2-hydroxy-1-(4-((7-morpholino-5-(quinolin-3-yl)thiazolo[5,4-d]pyrimidin-2-yl)methyl)piperazin-1-yl)propan-1-one |
| 107. | 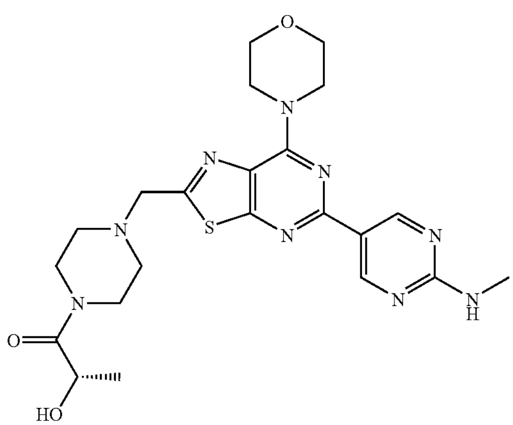 | (S)-2-hydroxy-1-(4-((5-(2-(methylamino)pyrimidin-5-yl)-7-morpholinothiazolo[5,4-d]pyrimidin-2-yl)methyl)piperazin-1-yl)propan-1-one |
| 108. | 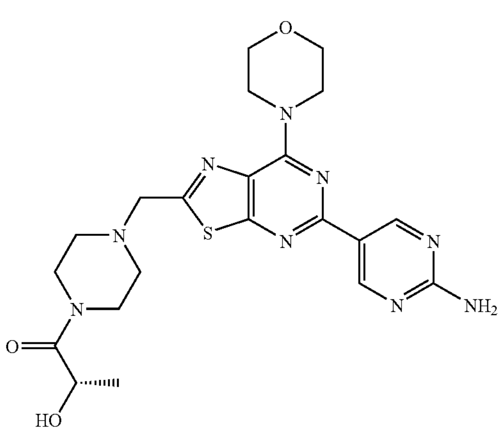 | (S)-1-(4-((5-(2-aminopyrimidin-5-yl)-7-morpholinothiazolo[5,4-d]pyrimidin-2-yl)methyl)piperazin-1-yl)-2-hydroxypropan-1-one |

TABLE 1-continued

| No. | Structure | Name |
|---|---|---|
| 109. | 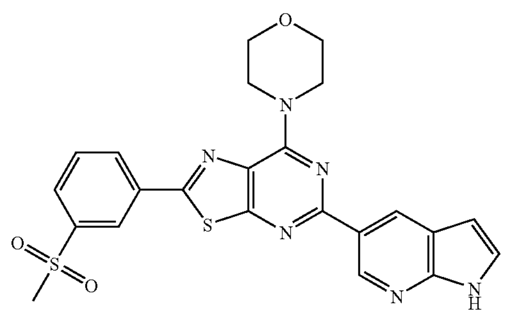 | 4-(2-(3-(methylsulfonyl)phenyl)-5-(1H-pyrrolo[2,3-b]pyridin-5-yl)thiazolo[5,4-d]pyrimidin-7-yl)morpholine |
| 110. | 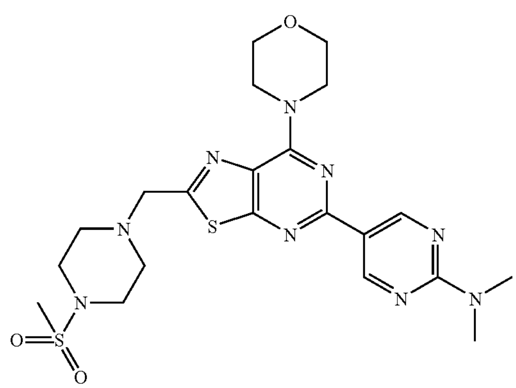 | N,N-dimethyl-5-(2-((4-(methylsulfonyl)piperazin-1-yl)methyl)-7-morpholinothiazolo[5,4-d]pyrimidin-5-yl)pyrimidin-2-amine |
| 111. | 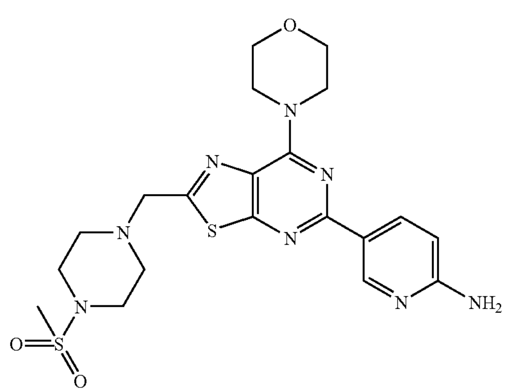 | 5-(2-((4-(methylsulfonyl)piperazin-1-yl)methyl)-7-morpholinothiazolo[5,4-d]pyrimidin-5-yl)pyridin-2-amine |
| 112. | 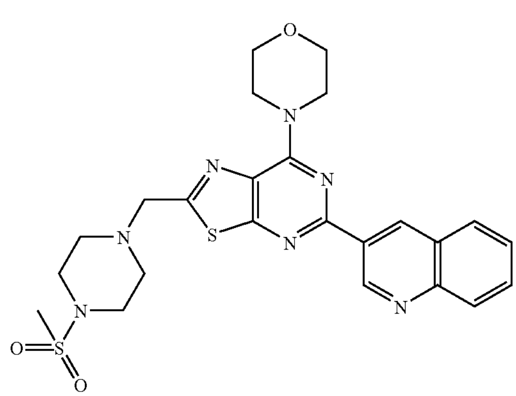 | 4-(2-((4-(methylsulfonyl)piperazin-1-yl)methyl)-5-(quinolin-3-yl)thiazolo[5,4-d]pyrimidin-7-yl)morpholine |

TABLE 1-continued

| No. | Structure | Name |
|---|---|---|
| 113. | 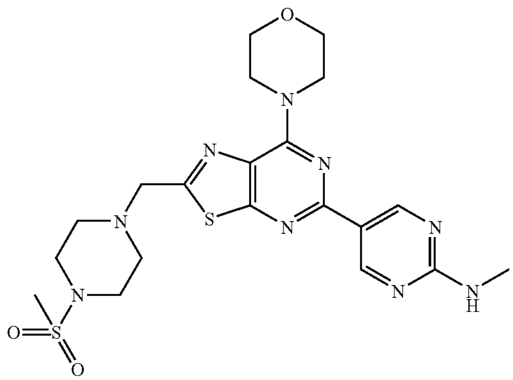 | N-methyl-5-(2-((4-(methylsulfonyl)piperazin-1-yl)methyl)-7-morpholinothiazolo[5,4-d]pyrimidin-5-yl)pyrimidin-2-amine |
| 114. | 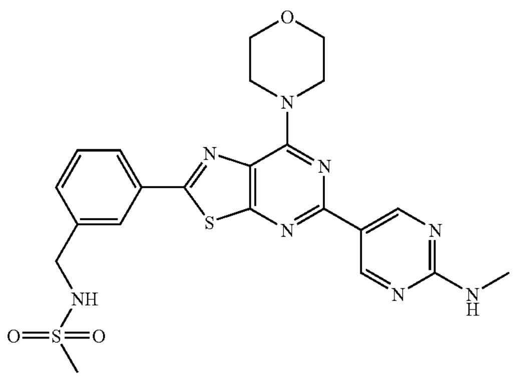 | N-(3-(5-(2-(methylamino)pyrimidin-5-yl)-7-morpholinothiazolo[5,4-d]pyrimidin-2-yl)benzyl)methanesulfonamide |
| 115. | 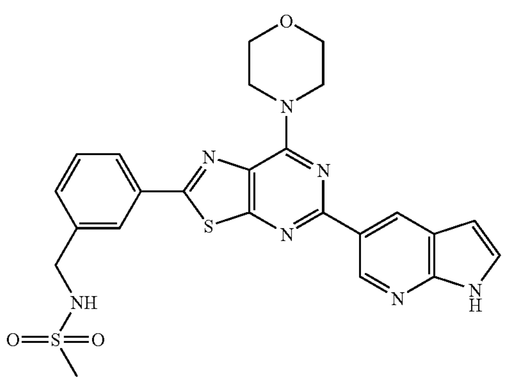 | N-(3-(7-morpholino-5-(1H-pyrrolo[2,3-b]pyridin-5-yl)thiazolo[5,4-d]pyrimidin-2-yl)benzyl)methanesulfonamide |
| 116. | 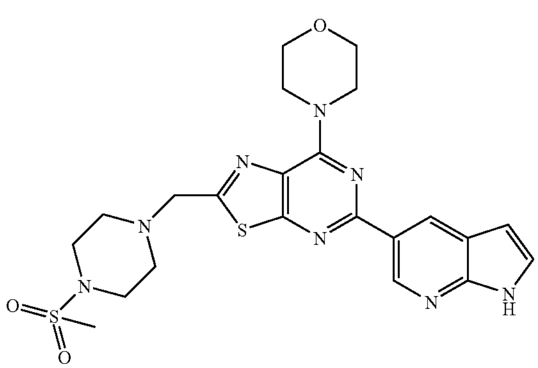 | 4-(2-((4-(methylsulfonyl)piperazin-1-yl)methyl)-5-(1H-pyrrolo[2,3-b]pyridin-5-yl)thiazolo[5,4-d]pyrimidin-7-yl)morpholine |

TABLE 1-continued

| No. | Structure | Name |
|---|---|---|
| 117. | 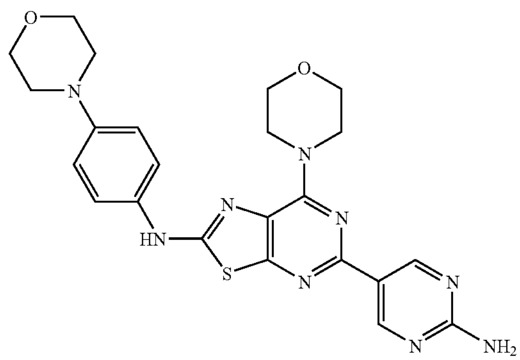 | 5-(2-aminopyrimidin-5-yl)-7-morpholino-N-(4-morpholinophenyl)thiazolo[5,4-d]pyrimidin-2-amine |
| 118. | 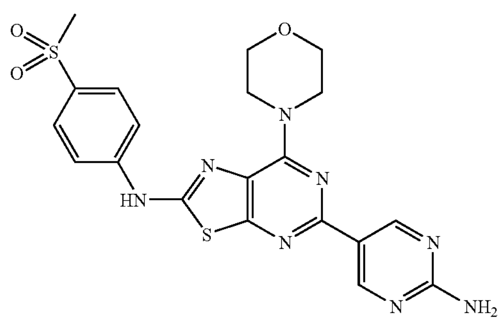 | 5-(2-aminopyrimidin-5-yl)-N-(4-(methylsulfonyl)phenyl)-7-morpholinothiazolo[5,4-d]pyrimidin-2-amine |
| 119. | 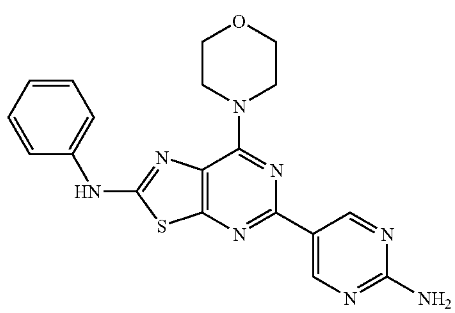 | 5-(2-aminopyrimidin-5-yl)-7-morpholino-N-phenylthiazolo[5,4-d]pyrimidin-2-amine |
| 120. | 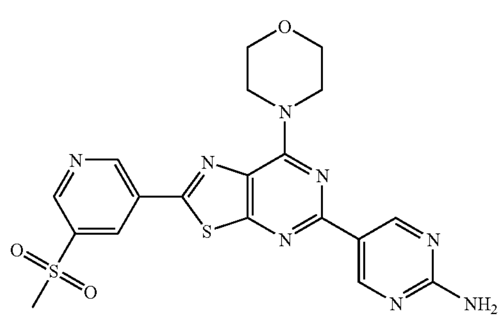 | 5-(2-(5-(methylsulfonyl)pyridin-3-yl)-7-morpholinothiazolo[5,4-d]pyrimidin-5-yl)pyrimidin-2-amine |

TABLE 1-continued

| No. | Structure | Name |
|---|---|---|
| 121. | 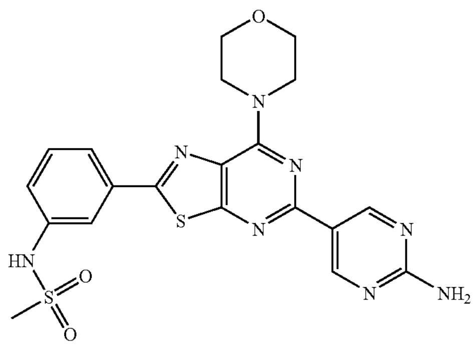 | N-(3-(5-(2-aminopyrimidin-5-yl)-7-morpholinothiazolo[5,4-d]pyrimidin-2-yl)phenyl)methanesulfonamide |
| 122. | 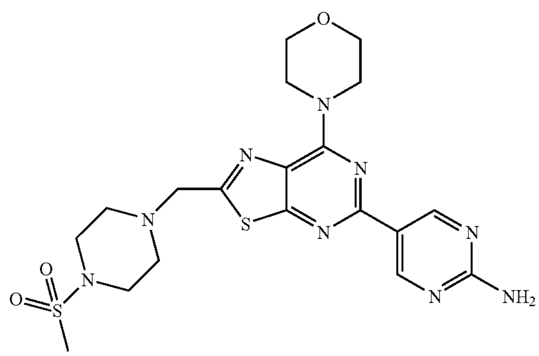 | 5-(2-((4-(methylsulfonyl)piperazin-1-yl)methyl)-7-morpholinothiazolo[5,4-d]pyrimidin-5-yl)pyrimidin-2-amine |
| 123. | 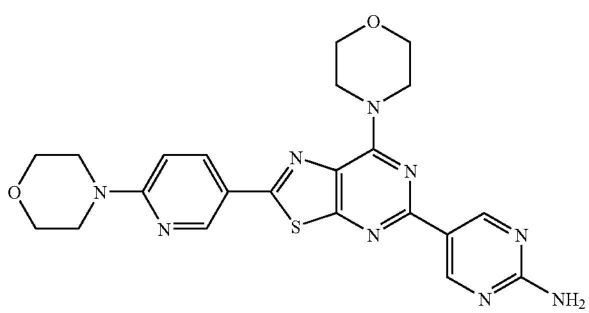 | 5-(7-morpholino-2-(6-morpholinopyridin-3-yl)thiazolo[5,4-d]pyrimidin-5-yl)pyrimidin-2-amine |
| 124. | 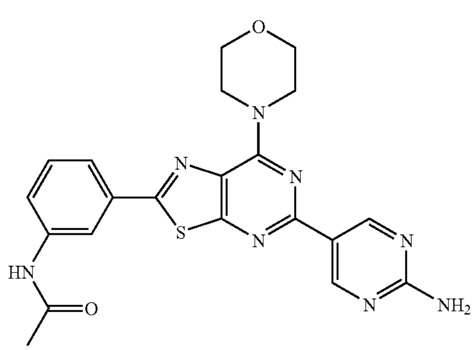 | N-(3-(5-(2-aminopyrimidin-5-yl)-7-morpholinothiazolo[5,4-d]pyrimidin-2-yl)phenyl)acetamide |

TABLE 1-continued

| No. | Structure | Name |
|---|---|---|
| 125. | 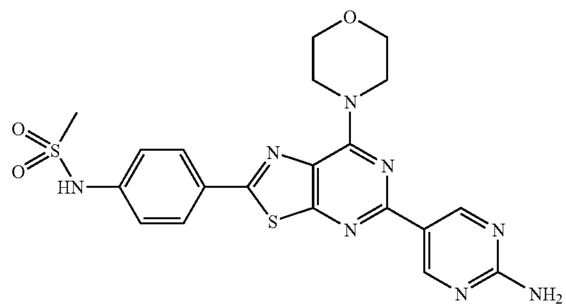 | N-(4-(5-(2-aminopyrimidin-5-yl)-7-morpholinothiazolo[5,4-d]pyrimidin-2-yl)phenyl)methanesulfonamide |
| 126. | 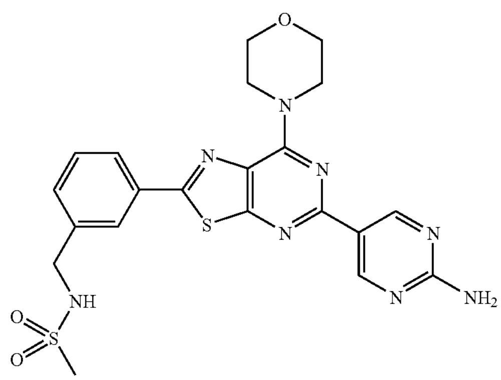 | N-(3-(5-(2-aminopyrimidin-5-yl)-7-morpholinothiazolo[5,4-d]pyrimidin-2-yl)benzyl)methanesulfonamide |
| 127. | 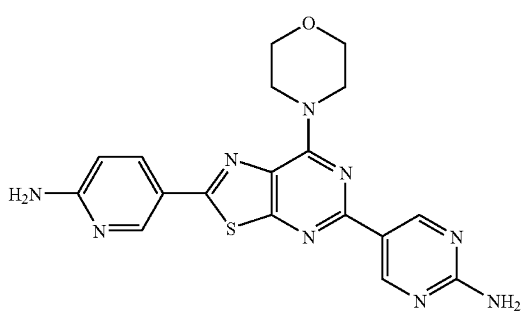 | 5-(2-(6-aminopyridin-3-yl)-7-morpholinothiazolo[5,4-d]pyrimidin-5-yl)pyrimidin-2-amine |
| 128. | 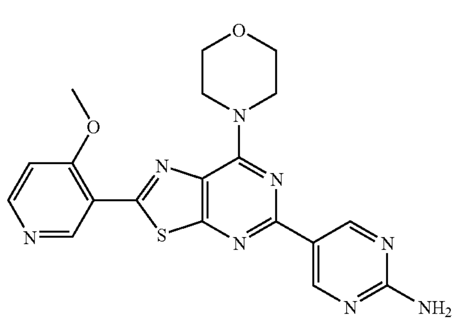 | 5-(2-(4-methoxypyridin-3-yl)-7-morpholinothiazolo[5,4-d]pyrimidin-5-yl)pyrimidin-2-amine |

TABLE 1-continued

| No. | Structure | Name |
|---|---|---|
| 129. | 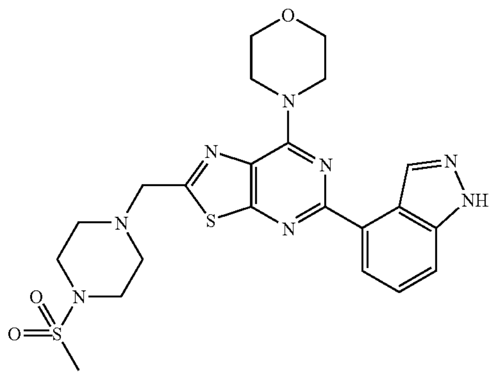 | 4-(5-(1H-indazol-4-yl)-2-((4-(methylsulfonyl)piperazin-1-yl)methyl)thiazolo[5,4-d]pyrimidin-7-yl)morpholine |
| 130. | 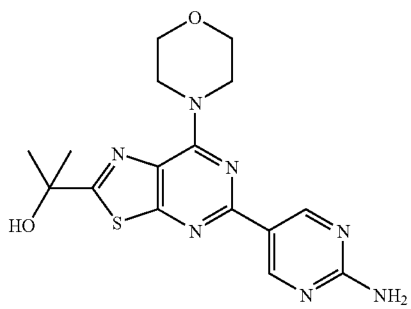 | 2-(5-(2-aminopyrimidin-5-yl)-7-morpholinothiazolo[5,4-d]pyrimidin-2-yl)propan-2-ol |
| 131. | 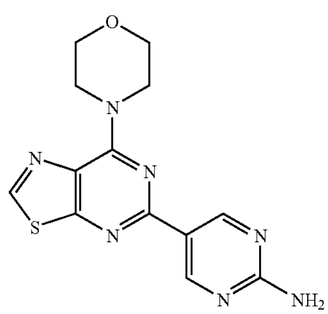 | 5-(7-morpholinothiazolo[5,4-d]pyrimidin-5-yl)pyrimidin-2-amine |
| 132. | 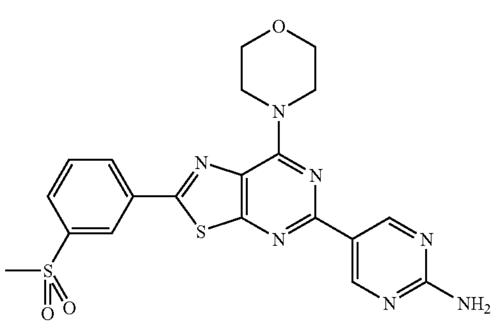 | 5-(2-(3-(methylsulfonyl)phenyl)-7-morpholinothiazolo[5,4-d]pyrimidin-5-yl)pyrimidin-2-amine |

TABLE 1-continued

| No. | Structure | Name |
|---|---|---|
| 133. | 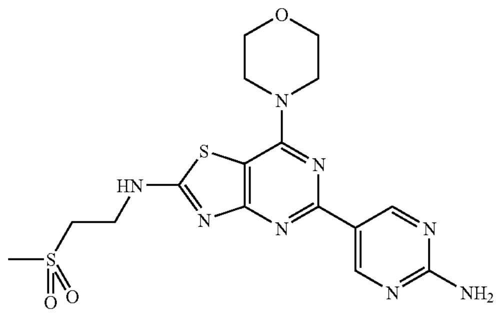 | 5-(2-aminopyrimidin-5-yl)-N-(2-(methylsulfonyl)ethyl)-7-morpholinothiazolo[4,5-d]pyrimidin-2-amine |
| 134. | 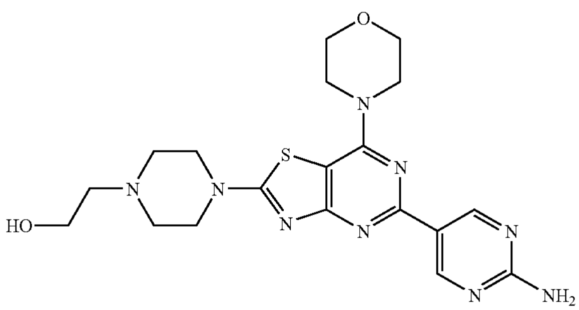 | 2-(4-(5-(2-aminopyrimidin-5-yl)-7-morpholinothiazolo[4,5-d]pyrimidin-2-yl)piperazin-1-yl)ethanol |
| 135. | 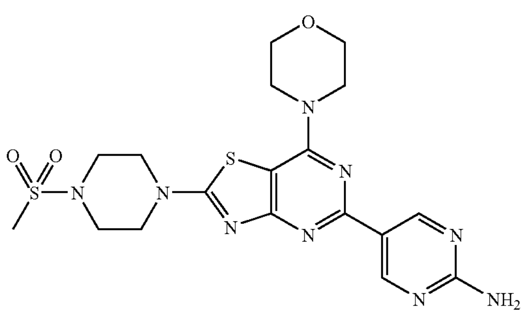 | 5-(2-(4-(methylsulfonyl)piperazin-1-yl)-7-morpholinothiazolo[4,5-d]pyrimidin-5-yl)pyrimidin-2-amine |
| 136. | 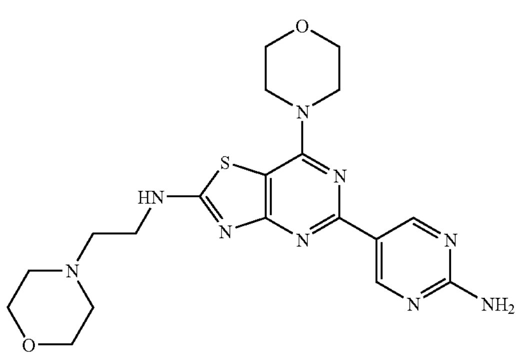 | 5-(2-aminopyrimidin-5-yl)-7-morpholino-N-(2-morpholinoethyl)thiazolo[4,5-d]pyrimidin-2-amine |

TABLE 1-continued

| No. | Structure | Name |
| --- | --- | --- |
| 137. | 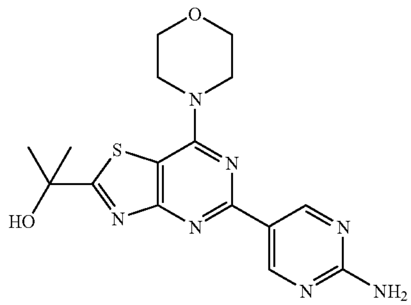 | 2-(5-(2-aminopyrimidin-5-yl)-7-morpholinothiazolo[4,5-d]pyrimidin-2-yl)propan-2-ol |
| 138. | 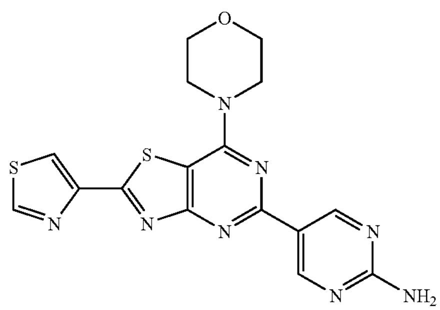 | 5-(7-morpholino-2-(thiazol-4-yl)thiazolo[4,5-d]pyrimidin-5-yl)pyrimidin-2-amine |
| 139. | 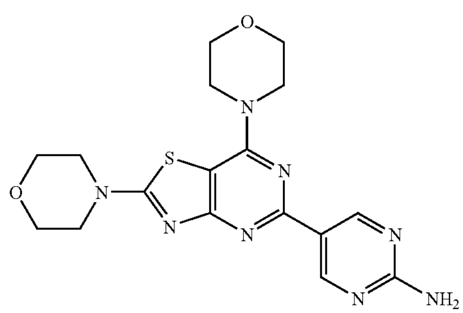 | 5-(2,7-dimorpholinothiazolo[4,5-d]pyrimidin-5-yl)pyrimidin-2-amine |
| 140. | 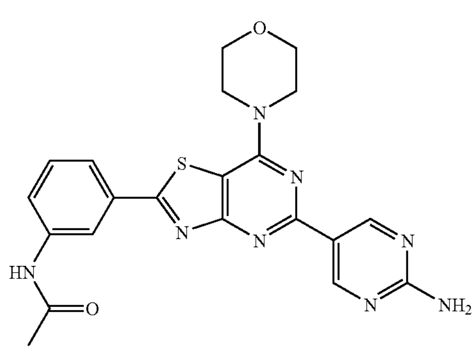 | N-(3-(5-(2-aminopyrimidin-5-yl)-7-morpholinothiazolo[4,5-d]pyrimidin-2-yl)phenyl)acetamide |

TABLE 1-continued

| No. | Structure | Name |
|---|---|---|
| 141. | 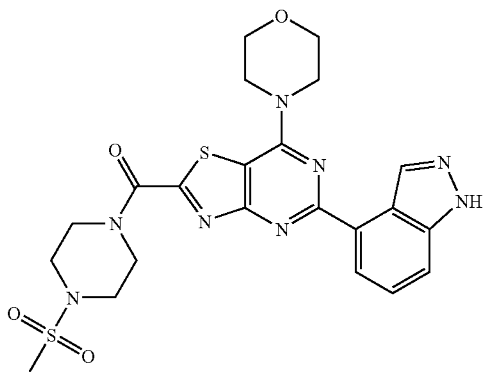 | (5-(1H-indazol-4-yl)-7-morpholinothiazolo[4,5-d]pyrimidin-2-yl)(4-(methylsulfonyl)piperazin-1-yl)methanone |
| 142. | 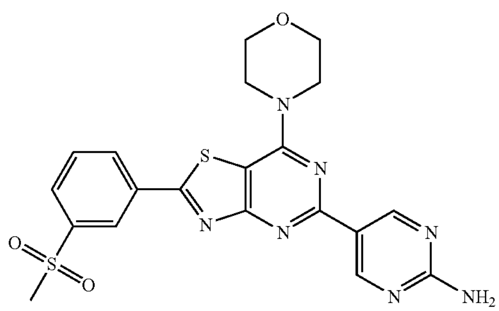 | 5-(2-(3-(methylsulfonyl)phenyl)-7-morpholinothiazolo[4,5-d]pyrimidin-5-yl)pyrimidin-2-amine |
| 143. | 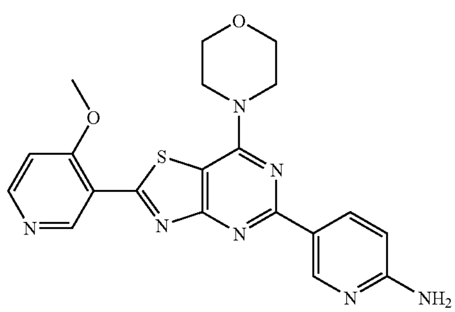 | 5-(2-(4-methoxypyridin-3-yl)-7-morpholinothiazolo[4,5-d]pyrimidin-5-yl)pyridin-2-amine |
| 144. | 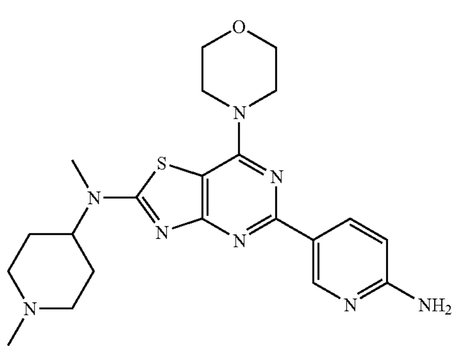 | 5-(6-aminopyridin-3-yl)-N-methyl-N-(1-methylpiperidin-4-yl)-7-morpholinothiazolo[4,5-d]pyrimidin-2-amine |

TABLE 1-continued

| No. | Structure | Name |
|---|---|---|
| 145. | 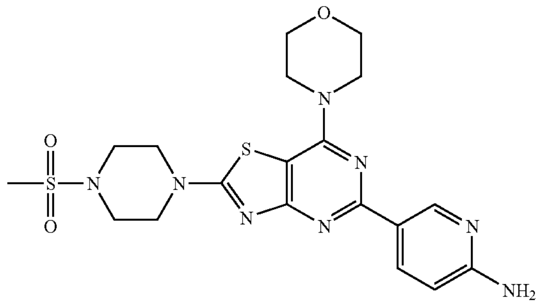 | 5-(2-(4-(methylsulfonyl)piperazin-1-yl)-7-morpholinothiazolo[4,5-d]pyrimidin-5-yl)pyridin-2-amine |
| 146. | 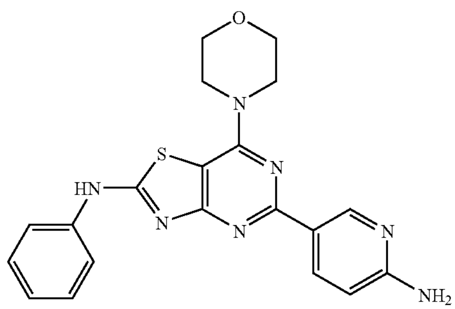 | 5-(6-aminopyridin-3-yl)-7-morpholino-N-phenylthiazolo[4,5-d]pyrimidin-2-amine |
| 147. | 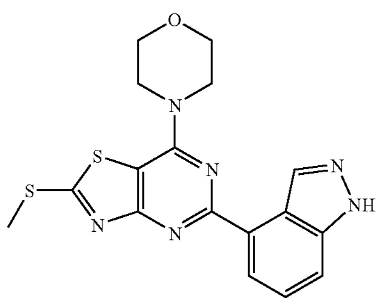 | 4-(5-(1H-indazol-4-yl)-2-(methylthio)thiazolo[4,5-d]pyrimidin-7-yl)morpholine |

Administration of Formula Ia and Ib Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula Ia or Ib compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula Ia and Ib Compounds

Formula Ia and Ib compounds are useful for treating diseases, conditions and/or disorders including, but not limited to, those characterized by over expression of lipid kinases, e.g. PI3 kinase. Accordingly, another aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of Formula Ia or Ib, or a stereoisomer, geometric isomer, tautomer, solvate, metabolite, or pharmaceutically acceptable salt thereof. Formula Ia and Ib compounds may be employed for the treatment of a hyperproliferative disease or disorder, including tumors, cancers, and neoplastic tissue, along with pre-malignant and non-neoplastic or non-malignant hyperproliferative disorders. In one embodiment, a human patient is treated with a compound of Formula Ia or Ib and a pharmaceutically acceptable carrier, adjuvant, or vehicle, wherein said compound of Formula Ia or Ib is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition or formulation comprising a compound of this invention in association with a pharmaceutically acceptable diluent or carrier. Pharmaceutical formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

A typical formulation is prepared by mixing a Formula Ia or Ib compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the Formula Ia or Ib compound is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a Formula Ia or Ib compound, or pharmaceutical composition thereof) or aid in the manufacturing of the pharmaceutical product (i.e., medicament).

The formulations may be prepared using conventional dissolution and mixing procedures. For example, the bulk drug substance (i.e., Formula Ia or Ib compound, or stabilized form of the compound (e.g., complex with a cyclodextrin derivative or other known complexation agent) is dissolved in a suitable solvent in the presence of one or more of the excipients described above. The Formula Ia or Ib compound is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the Formula Ia or Ib compound may be prepared for various routes and types of administration. For example, a compound having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. Formulations to be used for in vivo administration must be sterile. Such sterilization is readily accomplished by filtration through sterile filtration membranes. Formulations ordinarily can be stored as a solid composition, a lyophilized formulation or as an aqueous solution.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula Ia and Ib may be prepared. Suitable examples of sustained-release preparations include semipermeable matrices of solid hydrophobic polymers containing a compound of Formula Ia or Ib, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

Formulations of a Formula Ia or Ib compound suitable for oral administration may be prepared as discrete units such as pills, capsules, cachets or tablets each containing a predetermined amount of a compound of Formula Ia or Ib. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula Ia or Ib intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. The aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula Ia or Ib compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of Formula Ia or Ib compounds may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may be conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formulas Ia and Ib may be employed alone or in combination with other therapeutic agents for the treatment of a disease or disorder described herein, such as a hyperproliferative disorder (e.g., cancer). In certain embodiments, a compound of Formula Ia or Ib is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula Ia or Ib such that they do not adversely affect each other. Such compounds are suitably present in combination in amounts that are effective for the purpose intended. In one embodiment, a composition of this invention comprises a compound of Formula Ia or Ib, or a stereoisomer, geometric isomer, tautomer, solvate, metabolite, or pharmaceutically acceptable salt or prodrug thereof, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula Ia or Ib, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one Formula Ia or Ib compound, or a stereoisomer, geometric isomer, tautomer, solvate, metabolite, or pharmaceutically acceptable salt or prodrug thereof, and the use of at least one other cancer treatment method. The amounts of the compound(s) of Formula Ia or Ib and the other pharmaceutically active chemotherapeutic agent(s) and the relative timings of administration will be selected in order to achieve the desired combined therapeutic effect.

Metabolites of Formulas Ia and Ib Compounds

Also falling within the scope of this invention are the in vivo metabolic products of Formulas Ia and Ib compounds described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formulas Ia and Ib, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula Ia or Ib, or a stereoisomer, geometric isomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula Ia or Ib or a formulation thereof which is effective for treating the condition and may have a sterile access port (for example, the container may be an intravenous solution bag or a vial having a stopper pierceable by a hypodermic injection needle). At least one active agent in the composition is a compound of Formula Ia or Ib.

The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula Ia or Ib can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula Ia or Ib and, if present, the second pharmaceutical formulation. For example, if the kit comprises a first composition comprising a compound of Formula Ia or Ib and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula Ia or Ib, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula Ia or Ib contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula Ia or Ib and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

General Preparative Procedures
General Procedure A Suzuki Coupling:

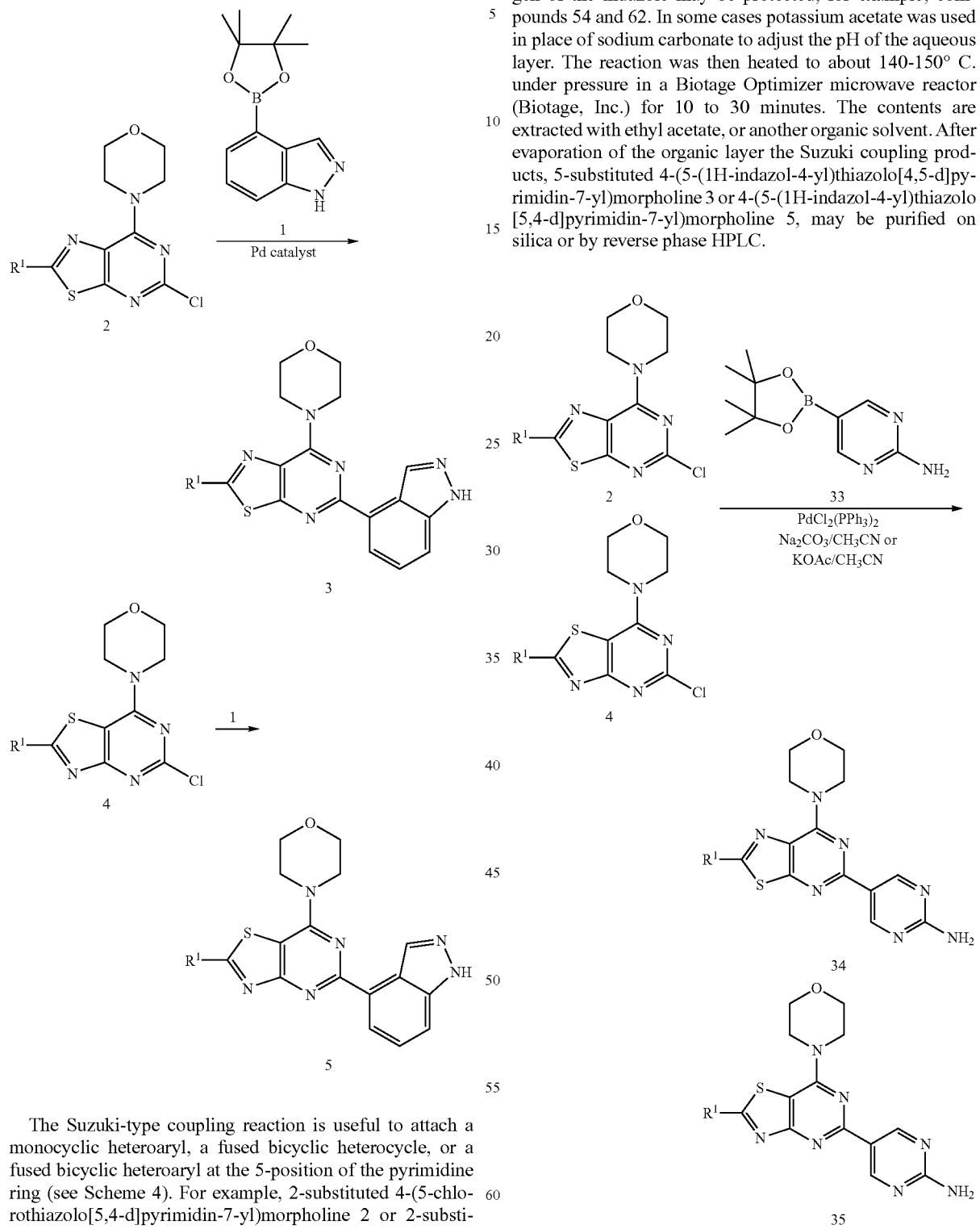

The Suzuki-type coupling reaction is useful to attach a monocyclic heteroaryl, a fused bicyclic heterocycle, or a fused bicyclic heteroaryl at the 5-position of the pyrimidine ring (see Scheme 4). For example, 2-substituted 4-(5-chlorothiazolo[5,4-d]pyrimidin-7-yl)morpholine 2 or 2-substituted 4-(5-chlorothiazolo[4,5-d]pyrimidin-7-yl)morpholine 4 may be combined with 1.5 equivalents of 4-(4,4,5,5-tetramethyl-1,3,2-dioxaborolan-2-yl)1H-indazole 1, and dissolved in 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the indazole boronic ester indicated. Also alternatively, the nitrogen of the indazole may be protected, for example; compounds 54 and 62. In some cases potassium acetate was used in place of sodium carbonate to adjust the pH of the aqueous layer. The reaction was then heated to about 140-150° C. under pressure in a Biotage Optimizer microwave reactor (Biotage, Inc.) for 10 to 30 minutes. The contents are extracted with ethyl acetate, or another organic solvent. After evaporation of the organic layer the Suzuki coupling products, 5-substituted 4-(5-(1H-indazol-4-yl)thiazolo[4,5-d]pyrimidin-7-yl)morpholine 3 or 4-(5-(1H-indazol-4-yl)thiazolo[5,4-d]pyrimidin-7-yl)morpholine 5, may be purified on silica or by reverse phase HPLC.

Procedures to attach a monocyclic heteroaryl at the 5-position of the pyrimidine ring include where substituted 5-chloro-7-morpholin-4-yl-thiazolo[5,4-d]pyrimidine 2 or 5-chloro-7-morpholin-4-yl-thiazolo[4,5-d]pyrimidine 4 was combined with 1.5 equivalents of 5-(4,4,5,5-tetramethyl-1,3, 2-dioxaborolan-2-yl)pyrimidin-2-amine 33 (alternatively, a variety of boronic acids or boronic esters can be used in place of 33), and dissolved in 3.0 equivalents of sodium carbonate as a 1 molar solution in water and an equal volume of acetonitrile. In some cases potassium acetate was used in place of sodium carbonate to adjust the pH of the aqueous layer. The reaction was then heated to between 140-150° C. under pressure in a Biotage optimizer microwave reactor for 10 to 30 minutes. The contents were extracted with ethyl acetate. After evaporation of the organic layer the product, 34 or 35, was purified on silica or by reverse phase HPLC.

General Procedure B Amide Coupling:

with 1.5 eq HATU, 3 eq of primary or secondary amine ($R_2NH$ where $R=H$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl) and 3 eq of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified via reverse phase HPLC to yield amide products 7 or 9.

General Procedure C Sulfonamide Formation:

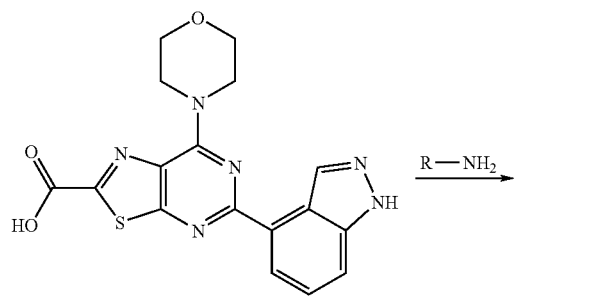

6

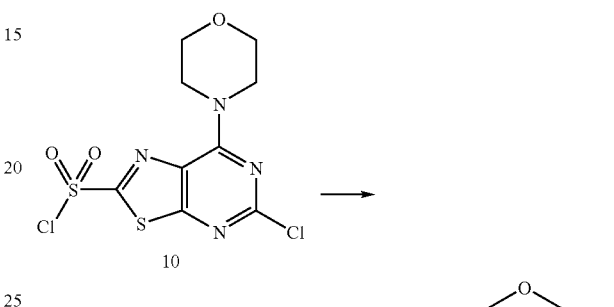

10

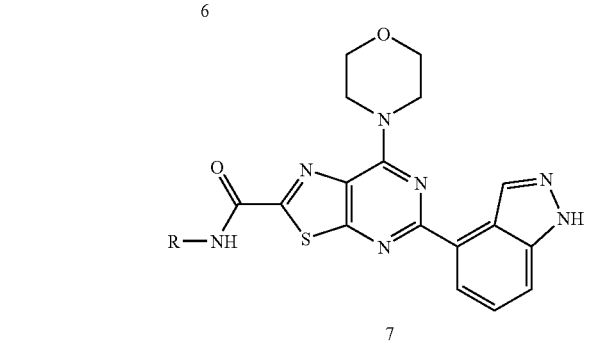

7

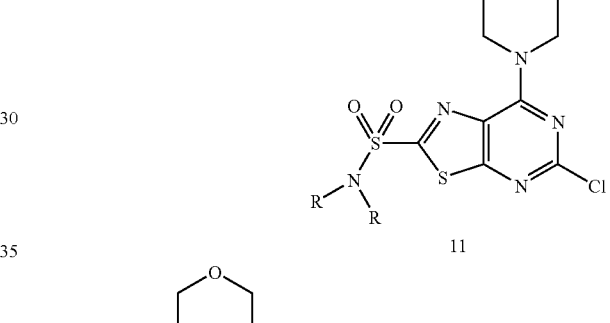

11

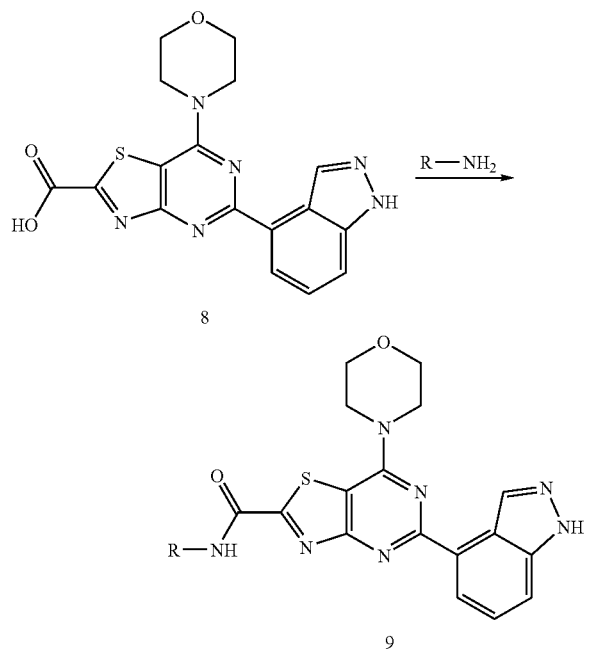

8

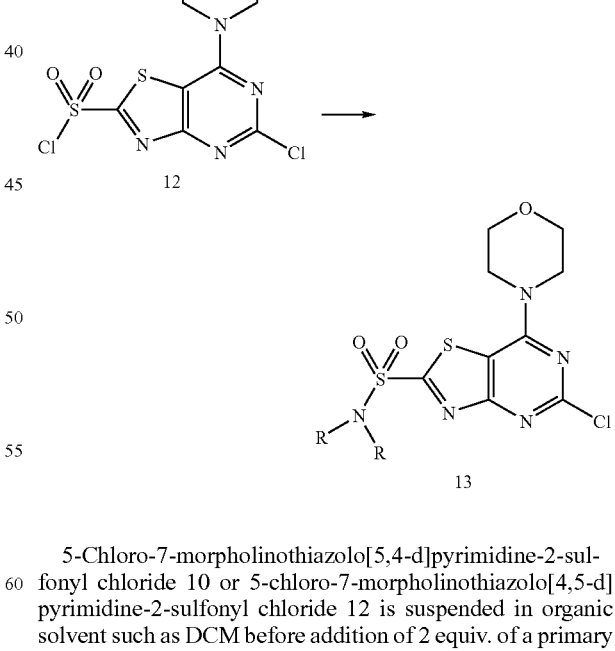

12

13

9

5-(1H-indazol-4-yl)-7-morpholinothiazolo[5,4-d]pyrimidine-2-carboxylic acid 6 or 5-(1H-indazol-4-yl)-7-morpholinothiazolo[4,5-d]pyrimidine-2-carboxylic acid 8 is treated 5-Chloro-7-morpholinothiazolo[5,4-d]pyrimidine-2-sulfonyl chloride 10 or 5-chloro-7-morpholinothiazolo[4,5-d]pyrimidine-2-sulfonyl chloride 12 is suspended in organic solvent such as DCM before addition of 2 equiv. of a primary or secondary amine ($R_2NH$ where $R=H$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl), and 3 eq of a tertiary amine base such as diisopropylethylamine (DIPEA). The reactions may be monitored by LCMS until complete.

The crude reaction mixtures are diluted with ethyl acetate, extracted with saturated ammonium chloride and back-extracted with ethyl acetate. The crude sulfonamide intermediates 11 and 13 are used directly in the subsequent Suzuki couplings.

General Procedure D Alcohol Synthesis

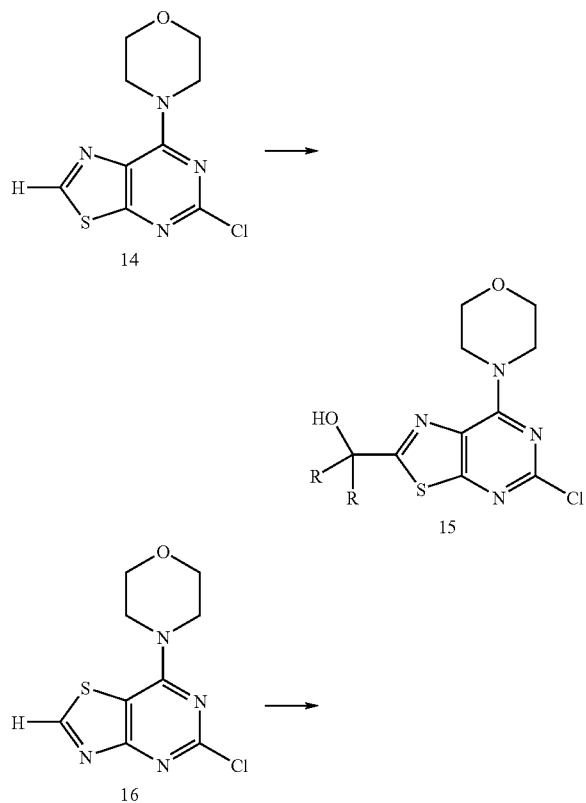

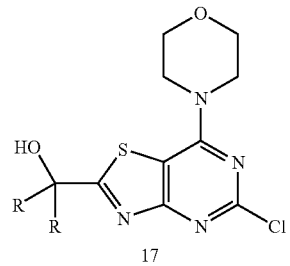

4-(5-Chlorothiazolo[5,4-d]pyrimidin-7-yl)morpholine 14 (U.S. Pat. No. 3,850,917) or 4-(5-chlorothiazolo[4,5-d]pyrimidin-7-yl)morpholine 16 is dissolved or suspended at a 0.2 molar concentration in THF and cooled to about −50° C. in a dry ice/acetonitrile bath before adding 2 equivalents of 2.5 M nBuLi in hexanes. After 15 minutes, about 3.0 molar equivalents of an aldehyde or ketone ($R_2CO$ where R=H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl) was added to the solution. The reaction continued to stir at −50° C. for 1 h and then in most cases was allowed to come to 0° C. When the reaction was complete by TLC or mass spec. it was quenched into a saturated ammonium chloride solution and extracted two times with EtOAc. The organic layer was concentrated and either used as a crude mixture, or purified on silica, to give the product 15 or 17.

General Procedure E Sequential Nucleophilic Amine Substitution/Suzuki Coupling Reaction

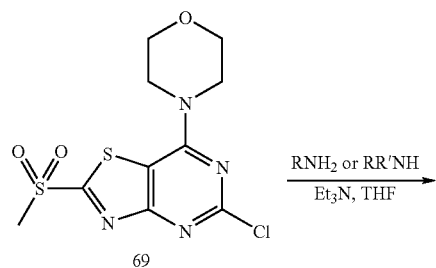

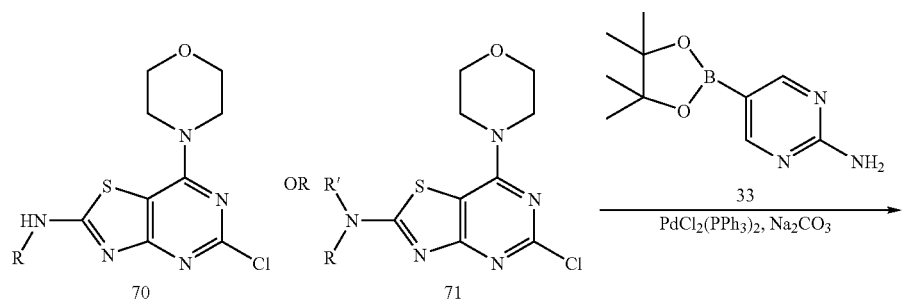

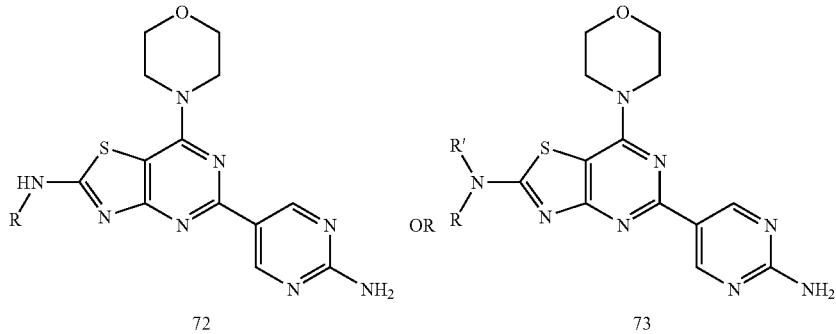

4-(5-Chloro-2-(methylsulfonyl)thiazolo[4,5-d]pyrimidin-7-yl)morpholine 69 (1.0 eq) was dissolved in tetrahydrofuran (0.1 M). Primary (or secondary) amine (1.4 eq) and triethylamine (1.4 eq) were slowly added to give 70 or 71. The solution was stirred for 5 minutes at 40° C. and the solvent was removed in vacuo. To the residue was added 1.5 eq of 5-(4,4,5,5-tetramethyl-1,3,2-dioxaborolan-2-yl)pyrimidin-2-amine 33 (or 5-(4,4,5,5-tetramethyl-1,3,2-dioxaborolan-2-yl)pyridin-2-amine, or other like boronate reagent), trans-dichlorobis(triphenylphosphine)palladium(II) (0.07 eq) and equal parts of 1M Na$_2$CO$_3$ (3.0 eq) and acetonitrile. The solution was microwaved at 130° C. for 10 minutes. Upon completion, water was added to the reaction mixture and solid was filtered to yield crude 72 or 73.

General Procedure F Suzuki Coupling Reactions in One Pot 4-(5-Chloro-2-iodothiazolo[5,4-d]pyrimidin-7-yl)morpholine 18 (1 eq), boronic acid (R$^1$—B(OH)$_2$, 1.1 eq) and bis(triphenylphosphine)palladium(II) dichloride (0.1 eq) in 1M Na$_2$CO$_3$ aqueous solution (3 eq) and acetonitrile (3 eq) was heated to 100° C. in a sealed microwave reactor for 10 to 40 min to give 2-substituted 19. Upon completion, 4-(4,4,5,5-tetramethyl-1,3,2-dioxaborolan-2-yl)-1H-indazole 1 (1.3 eq) and bis(triphenylphosphine)palladium(II) dichloride (0.1 eq) were added in the same pot. The reaction mixture was heated to 150° C. in a sealed microwave reactor for 10 to 15 min. The mixture was extracted with ethyl acetate (3×5 mL). The combined organic layers were concentrated to yield crude 20.

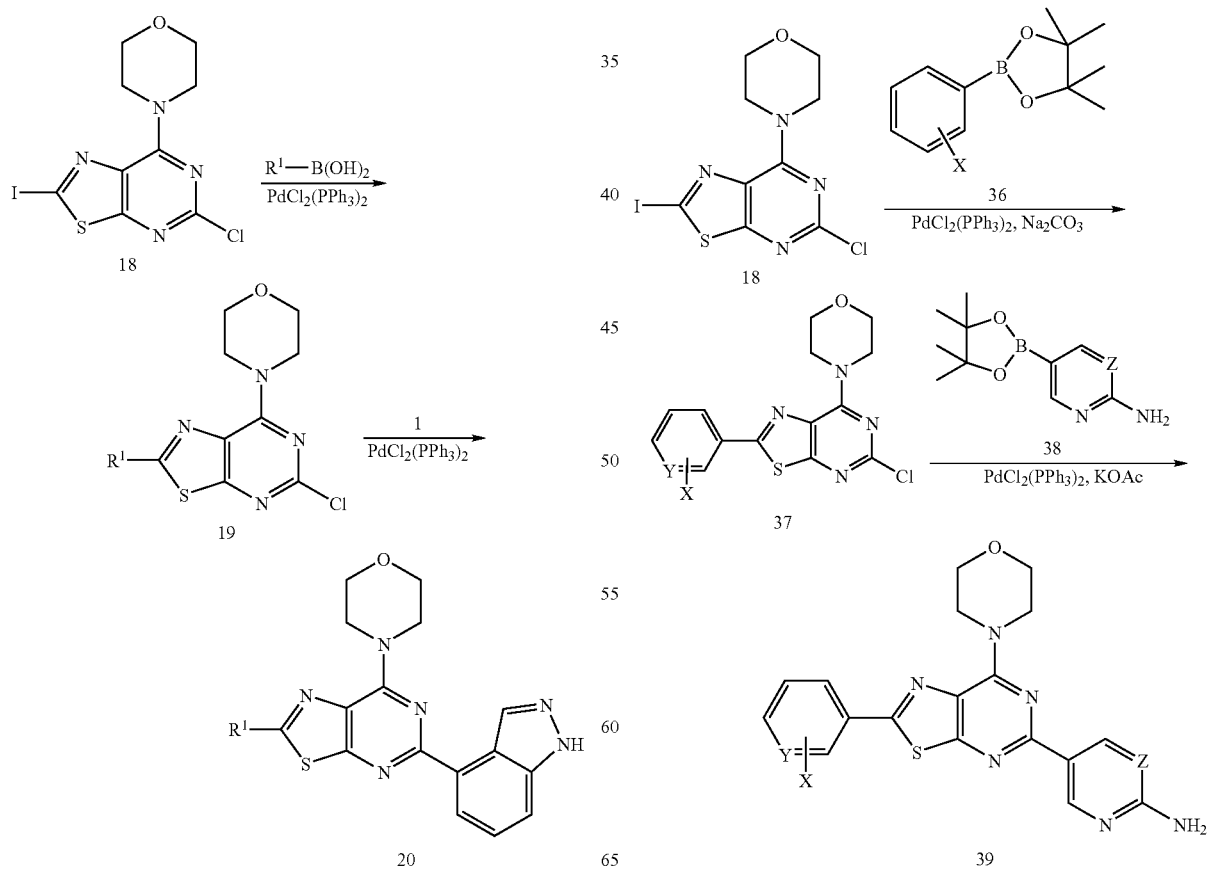

Alternatively, intermediate 4-(5-chloro-2-iodothiazolo[5,4-d]pyrimidin-7-yl)morpholine 18 (1.0 eq), optionally substituted phenylboronic acid 36 or heterocycloboronic acid (1.05 eq) and bis(triphenylphosphine)palladium(II) dichloride (0.1 eq) in 1M $Na_2CO_3$ aqueous solution (3.0 eq) and an equal volume of acetonitrile were heated to 100° C. in a sealed microwave reactor for 10-30 min. Upon completion, water was added and solid was filtered to give the 5-substituted intermediate 37 which was reacted with a monocyclic heteroaryl boronate reagent 38 (1.5 eq), such as 5-(4,4,5,5-tetramethyl-1,3,2-dioxaborolan-2-yl)pyrimidin-2-amine 33, and bis(triphenylphosphine)palladium(II) dichloride (0.07 eq) in 1M $Na_2CO_3$ (or 1M KOAc) aqueous solution (3.0 eq) and an equal volume of acetonitrile at 140° C. in a sealed microwave reactor for 10-15 min. Upon completion, water was added to the reaction mixture and solid was filtered to yield the crude 2-substituted intermediate 39, where X=$SO_2Me$, OMe, $NH_2$, $CH_2NHSO_2Me$, $NHSO_2Me$, morpholino, $NHCOCH_3$; Y=CR, N; and Z=CR, N.

General Procedure G Amide Coupling Reaction

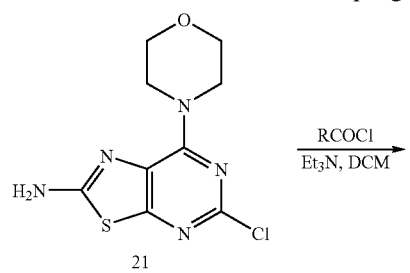

5-Chloro-7-morpholinothiazolo[5,4-d]pyrimidin-2-amine 21 (1 eq), an acid chloride (1.5~2 eq) in dichloromethane is stirred where R=H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl. The reaction is monitored by LC/MS until complete. The mixture is evaporated to give the crude amide 22, which may be directly used for the next step reaction without purification.

General Procedure H Preparation of Acetamide, Benzamidines, and Sulfonamides

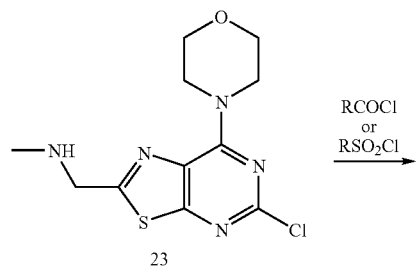

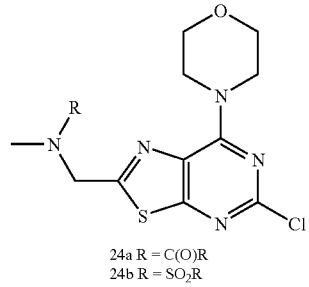

24a R = C(O)R
24b R = $SO_2R$

To a 0.25 to 0.40 M solution of 1-(5-chloro-7-morpholinothiazolo[5,4-d]pyrimidin-2-yl)-N-methylmethanamine 23 in DCM cooled to 0° C. is added 1.5 eq. of TEA, followed by the dropwise addition of 1.0 to 1.5 eq. of an acid chloride or sulfonylchloride, diluted in DCM, where R=H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl. The reaction is stirred at ambient temperature and monitored for completeness by LCMS. After completion, the reaction volume is increased with DCM, and dilute aqueous sodium bicarbonate is added to the solution. The organic and aqueous layers are separated. Finally, the organic layer is washed with brine and dried ($MgSO_4$). The dried organic solution is concentrated in vacuo and purified by silica chromatography if desired to the amide 24a or sulfonamide 24b product.

General Procedure I Amide Coupling Reaction for Benzenamine

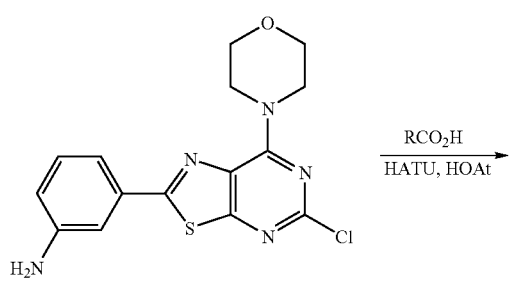

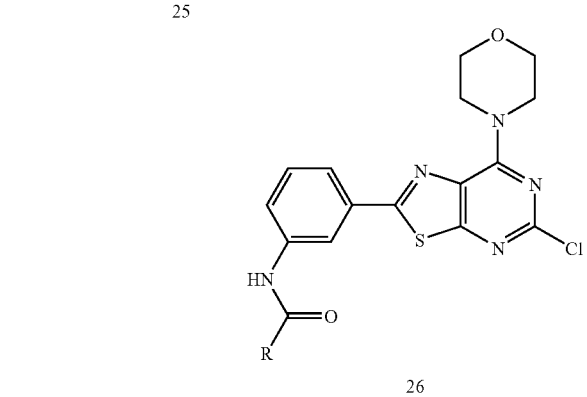

3-(5-Chloro-7-morpholinothiazolo[5,4-d]pyrimidin-2-yl)aniline 25 (1 eq), carboxylic acid ($RCO_2H$, 1.5 eq) where R=H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, 1-hydroxy-7-azabenzotriazole (HOAt, 0.2 eq), O-(7-azabenzotriazol-1-yl)-(N,N,N',N'-tetramethyluronium hexafluorophosphate (HATU, 1.5 eq), and N,N-diisopropylethylamine (2.5 eq) in DMF is stirred at room temperature. The reaction is monitored by LC/MS until complete. The reaction mixture is diluted with ethyl acetate, washed with saturated sodium bicarbonate and brine. The organic layer is dried over MgSO$_4$, filtered and evaporated to yield amide product 26.

General Procedure J Buchwald Reaction, 2-Iodo Displacement and 5-Suzuki Coupling

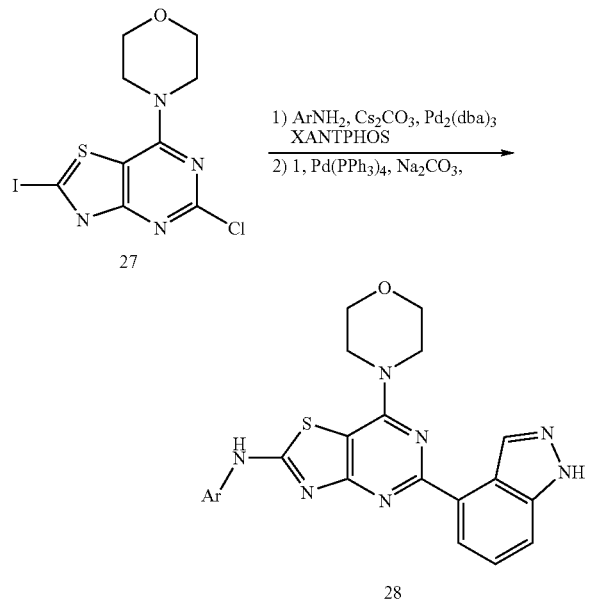

To a solution of 4-(5-chloro-2-iodothiazolo[4,5-d]pyrimidin-7-yl)morpholine 27 (0.05 g, 0.13 mmol) in DMF (1.00 ml) was added the appropriate aniline (200 mol %), Cs$_2$CO$_3$ (50 mol %), Pd$_2$(dba)$_3$ (5 mol %), and XANTPHOS (10 mol %). The reaction was heated to 110° C. under pressure in a Biotage optimizer microwave reactor for 30 min. The resulting solution was concentrated in vacuo to give 28, after coupling with boronic acid reagent 1, following General Procedure A.

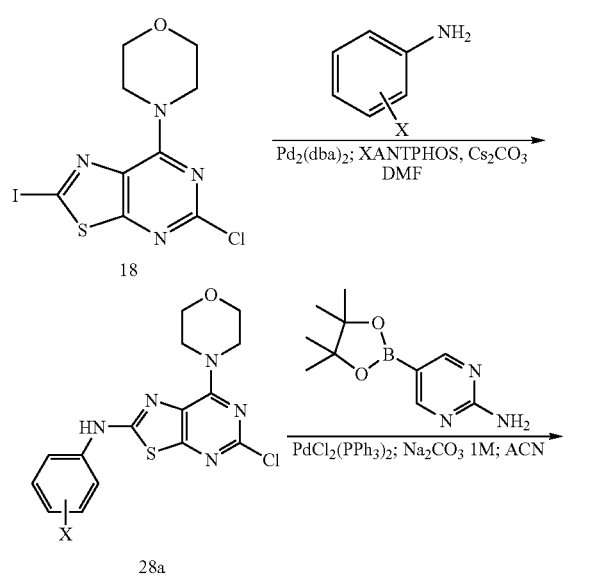

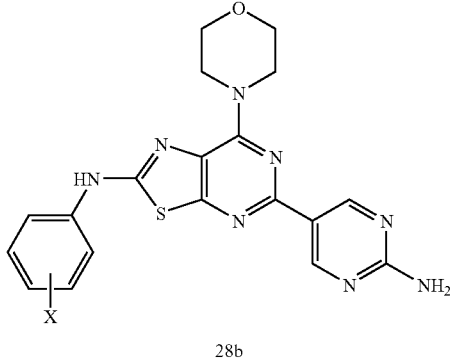

Alternatively, 18 (1.0 eq), optionally substituted aniline (2.0 eq), tris-(dibenzylideneacetone)dipalladium(0) (0.05 eq), 9,9-dimethyl-4,5-bis(diphenylphosphino)xanthene (0.10 eq), and cesium carbonate (0.50 eq) in DMF (0.15 M) were heated to 100-115° C. in a sealed microwave reactor for 15-30 min. Upon completion, the reaction mixture was concentrated in vacuo and crude mixture was purified by silica gel chromatography to give intermediate 28a which was reacted with 5-(4,4,5,5-tetramethyl-1,3,2-dioxaborolan-2-yl)pyrimidin-2-amine (1.5 eq) and bis(triphenylphosphine)palladium(II) dichloride (0.07 eq) in 1M Na$_2$CO$_3$ aqueous solution (3.0 eq) and an equal volume of acetonitrile and heated to 140° C. in a sealed microwave reactor for 10 min. Upon completion, water was added to the reaction mixture and solid was filtered to yield crude 28b where X is H, SO$_2$Me, or morpholino.

General Procedure K 2-Aminoalkyl Acylation and 5-Suzuki Coupling

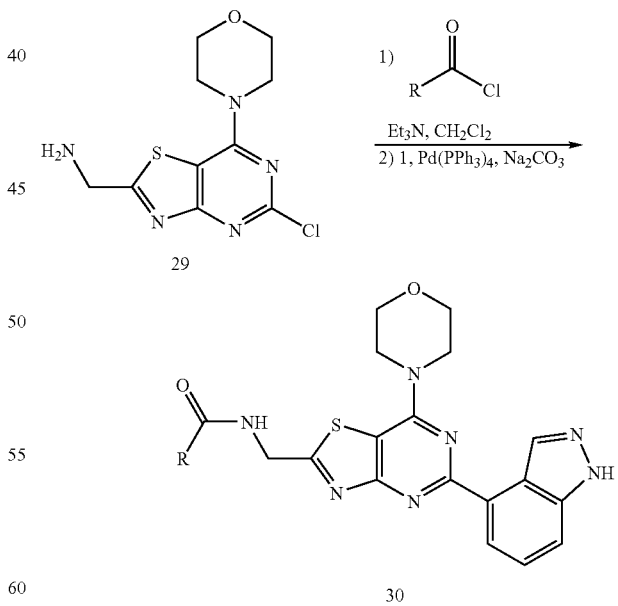

To a solution of (5-chloro-7-morpholinothiazolo[4,5-d]pyrimidin-2-yl)methanamine 29 (50 mg, 0.2 mmol) in CH$_2$Cl$_2$ (4 mL) is added Et$_3$N (84 µL, 0.6 mmol) and the appropriate acid chloride or HCl salt thereof (0.3 mmol) where R=H, C$_1$-C$_{12}$ alkyl, C$_2$-C$_8$ alkenyl, C$_2$-C$_8$ alkynyl, C$_3$-C$_{12}$ carbocyclyl, $C_2$-$C_{20}$ heterocyclyl, $C_6$-$C_{20}$ aryl, or $C_1$-$C_{20}$ heteroaryl. The reaction is stirred 18-48 hr at room temperature before being quenched with water. The aqueous layer is extracted with EtOAc. The combined organics are dried over $Na_2SO_4$ and concentrated in vacuo. The 5-chloro crude product was coupled with boronate reagent 1 and palladium catalyst according to General Procedure A to give amide 30 which was purified by reversed phase HPLC purification.

Alternatively, to a solution of (5-chloro-7-morpholinothiazolo[4,5-d]pyrimidin-2-yl)methanamine 29 (111 mg, 0.39 mmol) in DMF (5 mL) is added 2,6-lutidine (48.2 μL, 0.41 mmol) and the appropriate acid chloride or HCl salt thereof (0.39 mmol). The reaction is stirred 18-72 hr at room temperature before being quenched with water. The aqueous layer is extracted with EtOAc. The combined organics are dried over $MgSO_4$ and concentrated in vacuo. The 5-chloro crude product is coupled with boronate reagent 7 and palladium catalyst according to General Procedure A to give 20 mg of amide 30 which is purified by reversed phase HPLC purification.

General Procedure L Amine Substitution on a 2-fluoropyridine

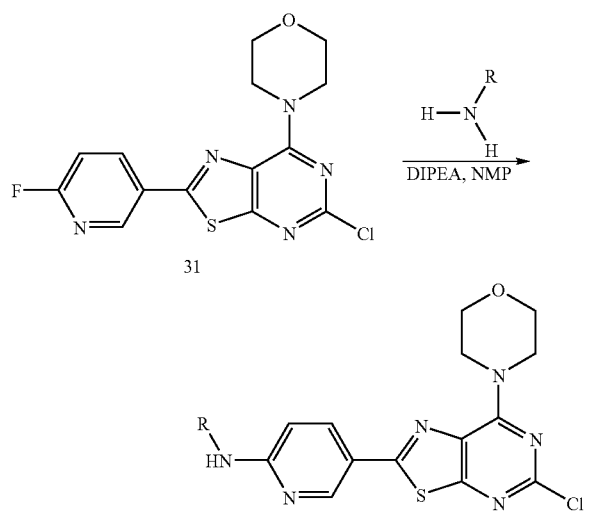

A mixture of 4-(5-chloro-2-(6-fluoropyridin-3-yl)thiazolo[5,4-d]pyrimidin-7-yl)morpholine 31, about four equivalents of a primary or secondary amine (R=H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl), and about two eq. diisopropylethylamine in N-methylpyrrolidine (~0.1M) is heated to about 130-140° C. in a sealed microwave reactor for 10-40 min, followed by removal of volatiles under high vacuum. The crude mixture is purified by flash chromatography to give the 2-pyridyl aminated intermediate product 32, which may be Suzuki coupled with a boronate reagent such as 1, following General Procedure A.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius (° C.). Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted on a Biotage system (Manufacturer: Dyax Corporation) having a silica gel column or on a silica SEP PAK® cartridge (Waters). $^1$H NMR spectra were recorded on a Varian instrument operating at 400 MHz. $^1$H NMR spectra were obtained in deuterated $CDCl_3$, $d_6$-DMSO, $CH_3OD$ or $d_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz). All compounds, final products and intermediates in the following Examples were characterized by LC/MS and the parent ion was detected.

Example 1

5,7-dichlorothiazolo[4,5-d]pyrimidine 42

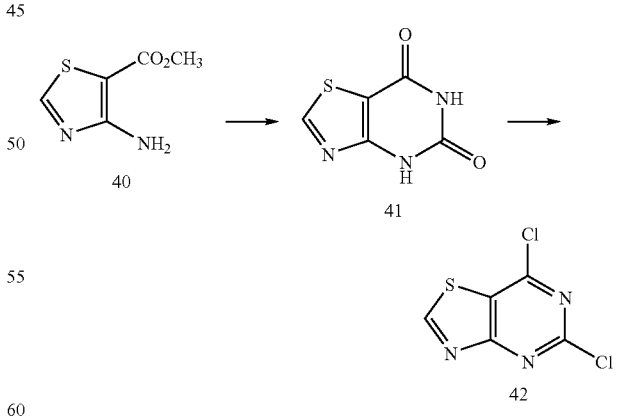

A mixture of methyl 4-aminothiazole-5-carboxylate 40 (WO 2006/096338; WO 2005/049613) and urea is heated at 190° C. for 2 hours. The hot reaction mixture is poured onto sodium hydroxide solution and any insoluble material is removed by filtration. The mixture is acidified (HCl, 2N) to yield thiazolo[4,5-d]pyrimidine-5,7(4H,6H)-dione 41

(Baker et al (1970) Jour. of the Chem. Soc. 18:2478-84; U.S. Pat. No. 3,277,093; Childress and McKee (1951) J. Am. Chem. Soc. 73:3862-64; Erlenmeyer and Furger (1943) Helv. Chem. Acta 26:366-68) as a white precipitate, which was collected by filtration and air dried.

A mixture of thiazolo[4,5-d]pyrimidine-5,7(4H,6H)-dione 41 and phosphorous oxychloride is heated at reflux for 6 h. The reaction mixture is then cooled and poured onto ice/water with vigorous stirring yielding a precipitate. The mixture was then filtered to yield 5,7-dichlorothiazolo[4,5-d]pyrimidine 42 as a white solid.

Example 2

4-(5-chlorothiazolo[4,5-d]pyrimidin-7-yl)morpholine 16

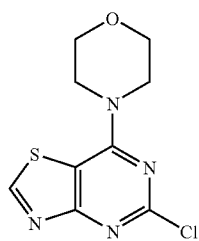

A mixture of 5,7-dichlorothiazolo[4,5-d]pyrimidine 42, morpholine (8.11 mL, 2.2 eq.) and MeOH (150 mL) was stirred at room temperature for 1 h. The reaction mixture was then filtered, washed with water and MeOH, to yield 4-(5-chlorothiazolo[4,5-d]pyrimidin-7-yl)morpholine 16 as a white solid.

Example 3

5-chloro-7-morpholinothiazolo[4,5-d]pyrimidine-2-carbaldehyde 43

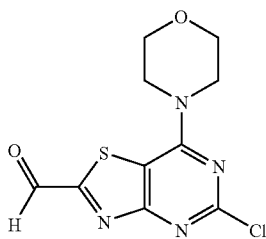

To a suspension of 4-(5-chlorothiazolo[4,5-d]pyrimidin-7-yl)morpholine 16 (1.75 g, 6.85 mmol) in dry THF (40 mL) at −78° C. was added a 2.5M solution of n-butyllithium (nBuLi) in hexane (3.3 mL, 1.2 eq.). After stirring for 1 h, dry DMF (796 µL, 1.5 eq.) was added. The reaction mixture was stirred for 1 h at −78° C. and then warmed slowly to room temperature. After a further 2 h at room temperature the reaction mixture poured onto ice/water yielding a yellow precipitate. This was collected by filtration and air-dried to yield 5-chloro-7-morpholinothiazolo[4,5-d]pyrimidine-2-carbaldehyde 43.

Example 4

5-chloro-7-morpholinothiazolo[5,4-d]pyrimidine-2-carbaldehyde 44

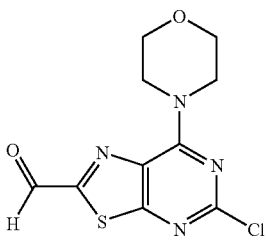

To a suspension of 4-(5-chlorothiazolo[5,4-d]pyrimidin-7-yl)morpholine 14 (1.75 g, 6.85 mmol) in dry THF at −78° C. was added a 2.5M solution of n-butyllithium (nBuLi) in hexane (3.3 mL, 1.2 eq.). After stirring for 1 h, dry DMF (796 uL, 1.5 eq.) was added. The reaction mixture was stirred for 1 h at −78° C. and then warmed slowly to room temperature. After a further 2 h at room temperature the reaction mixture was poured onto ice/water yielding a yellow precipitate. This was collected by filtration and air-dried to yield 5-chloro-7-morpholinothiazolo[5,4-d]pyrimidine-2-carbaldehyde 44.

Example 5

4-(4,4,5,5-Tetramethyl-[1,3,2]dioxaborolan-2-yl)-1H-indazole 1-route 1

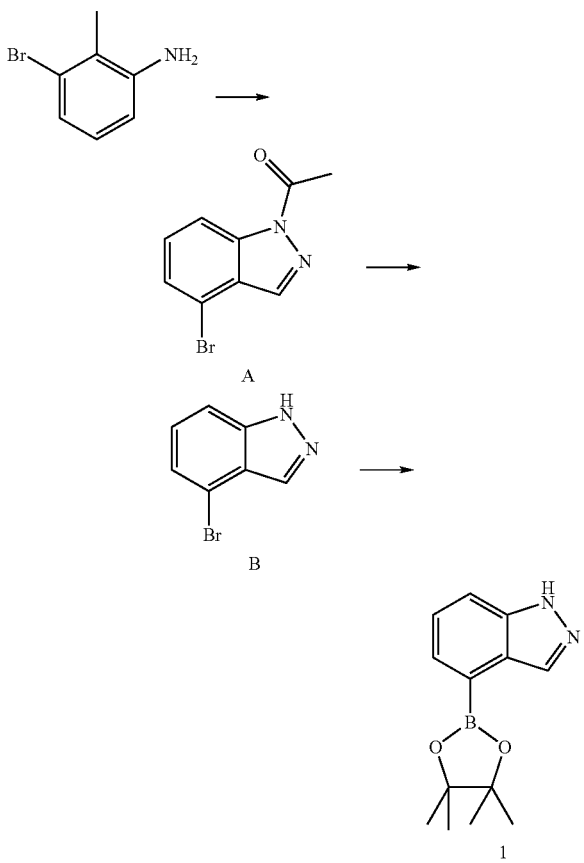

Following the procedures of WO 2006/046031 and WO 2006/046040, to a solution of 3-bromo-2-methyl aniline (5.0 g, 26.9 mmol) in chloroform (50 mL) was added potassium acetate (1.05 eq., 28.2 mmol, 2.77 g). Acetic anhydride (2.0 eq., 53.7 mmol, 5.07 mL) was added to the mixture cooling in ice-water. The mixture was then stirred at room temperature for 10 minutes after which time a white gelatinous solid formed. 18-Crown-6 (0.2 eq., 5.37 mmol, 1.42 g) was then added followed by iso-amyl nitrite (2.2 eq., 59.1 mmol, 7.94 mL) and the mixture was heated under reflux for 18 h. The reaction mixture was allowed to cool, and was partitioned between chloroform (3×100 mL) and saturated aqueous sodium hydrogen carbonate (100 mL). The combined organic extracts were washed with brine (100 mL), separated and dried ($MgSO_4$).

The crude product was evaporated onto silica and purified by chromatography eluting with 20%→40% EtOAc-petrol to give 1-(4-bromo-indazol-1-yl)-ethanone A (3.14 g, 49%) as an orange solid, and 4-bromo-1H-indazole B (2.13 g, 40%) as a pale orange solid. A $^1$H NMR (400 MHz, $CDCl_3$) 2.80 (3H, s), 7.41 (1H, t, J=7.8 Hz), 7.50 (1H, d, J=7.8 Hz), 8.15 (1H, s), 8.40 (1H, d, J=7.8 Hz). B: $^1$H NMR (400 MHz, $CDCl_3$) 7.25 (1H, t, J=7.3 Hz), 7.33 (1H, d, J=7.3 Hz), 7.46 (1H, d, J=7.3 Hz), 8.11 (1H, s), 10.20 (1H, br s).

To a solution of the 1-(4-bromo-indazol-1-yl)-ethanone A (3.09 g, 12.9 mmol) in MeOH (50 mL) was added 6N aqueous HCl (30 mL) and the mixture was stirred at room temperature for 7 h. The MeOH was evaporated and the mixture partitioned between EtOAc (2×50 mL) and water (50 mL). The combined organic layers were washed with brine (50 mL), separated and dried ($MgSO_4$). The solvent was removed by evaporation under reduced pressure to give 4-bromo-1H-indazole B (2.36 g, 93%).

To a solution of the 4-bromo-1H-indazole B (500 mg, 2.54 mmol) and bis(pinacolato)diboron (1.5 eq., 3.81 mmol) in DMSO (20 mL) was added potassium acetate (3.0 eq., 7.61 mmol, 747 mg; dried in drying pistol) and $PdCl_2(dppf)_2$ (3 mol %, 0.076 mmol, 62 mg). The mixture was degassed with argon and heated at 80° C. for 40 h. The reaction mixture was allowed to cool and partitioned between water (50 mL) and ether (3×50 mL). The combined organic layers were washed with brine (50 mL), separated and dried ($MgSO_4$). The crude material was purified by chromatography eluting with 30%→40% EtOAc-petrol to give an inseparable 3:1 mixture of the 4-(4,4,5,5-tetramethyl-[1,3,2]dioxaborolan-2-yl)-1H-indazole 1 (369 mg, 60%) and indazole (60 mg, 20%), isolated as a yellow gum which solidified upon standing to furnish as an off-white solid. $^1$H NMR (400 MHz, $d_6$-DMSO) 1.41 (12H, s), 7.40 (1H, dd, J=8.4 Hz, 6.9 Hz), 7.59 (1H, d, J=8.4 Hz), 7.67 (1H, d, J=6.9 Hz), 10.00 (1H, br s), 8.45 (1H, s), and indazole: 7.40 (1H, t), 7.18 (1H, t, J=7.9 Hz), 7.50 (1H, d, J=9.1 Hz), 7.77 (1H, d, J=7.9 Hz), 8.09 (1H, s). Impurity at 1.25.

Example 6

4-(4,4,5,5-Tetramethyl-[1,3,2]dioxaborolan-2-yl)-1H-indazole 1-route 2

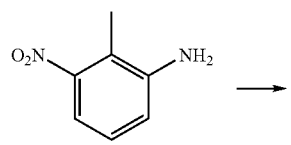

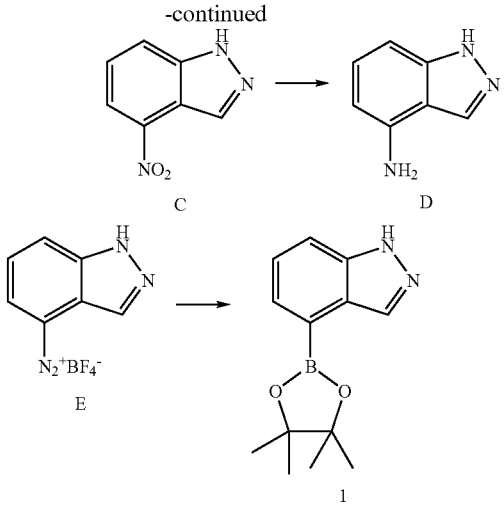

To a solution of 2-methyl-3-nitroaniline (2.27 g, 14.91 mmol) in acetic acid (60 mL) was added a solution of sodium nitrite (1.13 g, 1.1 eq.) in water (5 mL). After 2 h, the deep red solution was poured onto ice/water and the resulting precipitate collected by filtration to yield 4-nitro-1H-indazole C (1.98 g, 81%).

A mixture of 4-nitro-1H-indazole C (760 mg, 4.68 mmol), palladium on charcoal (10%, cat.) and ethanol (30 mL) was stirred under a balloon of hydrogen for 4 h. The reaction mixture was then filtered through celite, and the solvent removed in vacuo to yield 1H-indazol-4-ylamine D (631 mg, 100%).

An aqueous solution of sodium nitrite (337 mg, 4.89 mmol) in water (2 mL) was added dropwise to a suspension of 1H-indazol-4-ylamine D (631 mg, 4.74 mmol) in 6M hydrochloric acid (7.2 mL) at below 0° C. After stirring for 30 minutes, sodium tetrafluoroborate (724 mg) was added to the reaction mixture. A viscous solution resulted, which was filtered and washed briefly with water to yield 1H-indazole-4-diazonium tetrafluoroborate salt E (69) (218 mg, 20%) as a deep red solid.

Dry methanol (4 mL) was purged with argon for 5 minutes. To this was added 1H-indazole-4-diazonium tetrafluoroborate salt (218 mg, 0.94 mmol), bis-pinacolato diboron (239 mg, 1.0 eq.) and [1,1'-bis(diphenylphosphino)ferrocene]palladium (II) chloride (20 mg). The reaction mixture was stirred for 5 h and then filtered through celite. The residue was purified using flash chromatography to yield 4-(4,4,5,5-Tetramethyl-[1,3,2]dioxaborolan-2-yl)-1H-indazole 1, (117 mg).

Example 7

6-Fluoroindazole-4-Boronate Ester 45

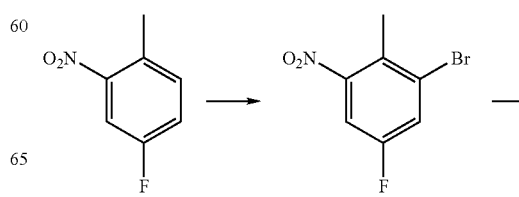

-continued

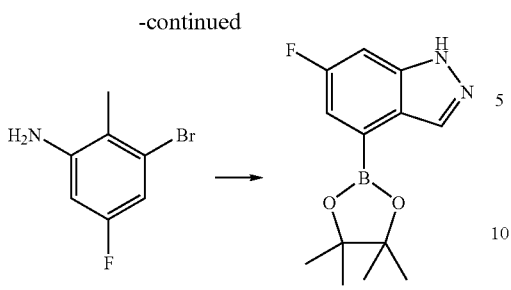

Following the procedures of WO 2006/046031, to a solution of 4-fluoro-2-nitrotoluene (3.44 g) in trifluoroacetic acid (13 mL) was added concentrated sulfuric acid (4 mL) followed by N-bromosuccinimide (5.92 g). The reaction mixture was stirred for 16 h and was then quenched with brine, extracted into ethyl acetate, and dried ($MgSO_4$). The solvent was removed in vacuo to furnish crude 1-bromo-5-fluoro-2-methyl-3-nitro-benzene (5.96 g).

To a solution of crude 1-bromo-5-fluoro-2-methyl-3-nitro-benzene (5.96 g) in MeOH (90 mL) was added concentrated hydrochloric acid (11.7 mL) and iron (6.1 g) and the reaction mixture was heated to reflux. After 16 h, the mixture was cooled, diluted with DCM, washed with sodium carbonate solution, dried ($MgSO_4$) and the solvent removed in vacuo. The residue was purified using flash chromatography to yield 3-bromo-5-fluoro-2-methyl-phenylamine (1.46 g).

To a solution of 3-bromo-5-fluoro-2-methyl-phenylamine (470 mg) in dioxane (6 mL) was added triethylamine (1.28 mL), palladium acetate (25 mg), 2-dicyclohexylphosphino biphenyl (161 mg) and pinacol borane (1.001 ml) and the mixture was heated to 80° C. for 4 h. The reaction mixture was cooled, diluted with chloroform, washed with brine, dried ($MgSO_4$) and the solvent removed in vacuo. The residue was purified using flash chromatography to yield 45 (466 mg).

Example 8

6-(Tributylstannyl)-1-((2-(trimethylsilyl)ethoxy)methyl)-1H-imidazo[4,5-b]pyridine 50

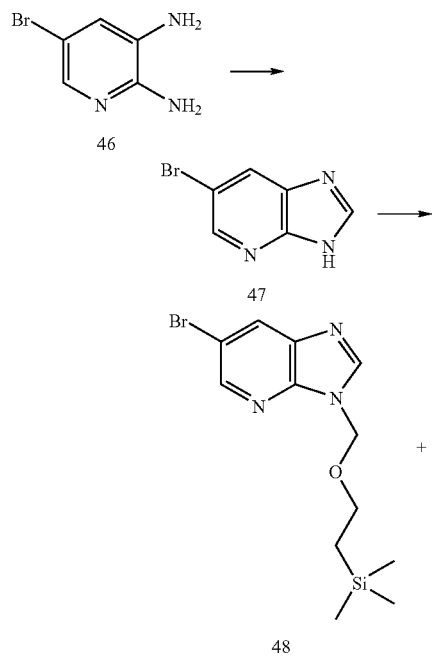

-continued

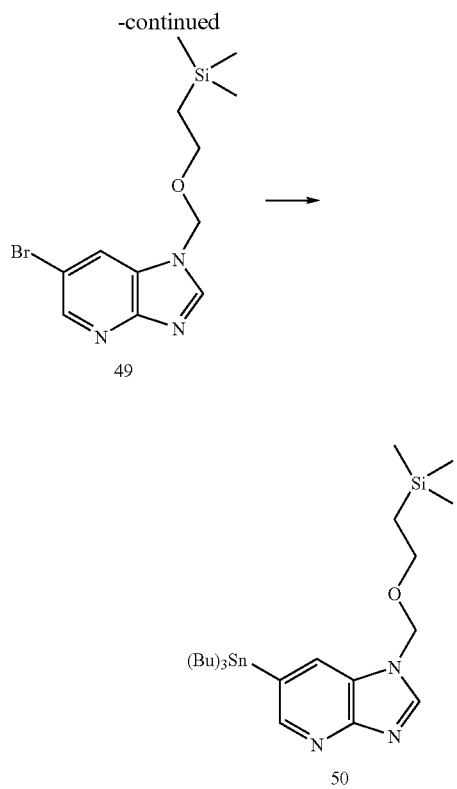

To 3.07 g of 5-bromo-2,3-diaminopyridine 46 was added 20 mL formic acid under $N_2$ and the reaction was heated to reflux for four hours and allowed to cool to room temperature. The reaction was stirred overnight at room temperature and complete reaction was confirmed by LCMS. The solution was concentrated in vacuo and purified by flash chromatography (DCM/MeOH) to give 1.64 g of compound 47 (51% yield). Compound 47 (1.64 g) in 40 mL THF was added to 0.22 g (1.1 eq) NaH in 10 mL THF under $N_2$ at −78° C. The reaction was stirred at −78° C. for 30 minutes followed by the addition of 1.45 g of SEM-Cl (1.05 eq) and allowed to warm up to room temperature. The reaction was stirred at room temperature overnight and complete reaction was confirmed by LCMS. The reaction was quenched with water followed by the addition of NaCl (not saturated) and the two products extracted with EtOAc and concentrated in vacuo. The two regioisomers were separated by flash chromatography (EtOAc/Hexanes) to give 1.68 g 48 and 0.5 g 49 (80% overall yield). Compound 49 (0.5 g) was dissolved in 50 mL dioxane followed by the addition of 1.76 g (2.0 eq) of bis(tributyltin), 88 mg (0.05 eq) of $Pd(PPh_3)_4$, and 0.19 g (3.0 eq) of LiCl. The reaction mixture was heated to reflux under $N_2$ for 1.5 hours and complete reaction confirmed by LCMS. The mixture was cooled to room temperature, filtered through celite (celite washed with EtOAc), rotary evaporated and purified by flash chromatography (EtOAc/Hexanes) to give 501 mg of 6-(tributylstannyl)-1-((2-(trimethylsilyl)ethoxy)methyl)-1H-imidazo[4,5-b]pyridine 50 (61% yield). MS (Q1) 539.2 (M)+

Example 9

2-methyl-6-(4,4,5,5-tetramethyl-1,3,2-dioxaborolan-2-yl)-3-((2-(trimethylsilyl)ethoxy)methyl)-3H-imidazo[4,5-b]pyridine 54

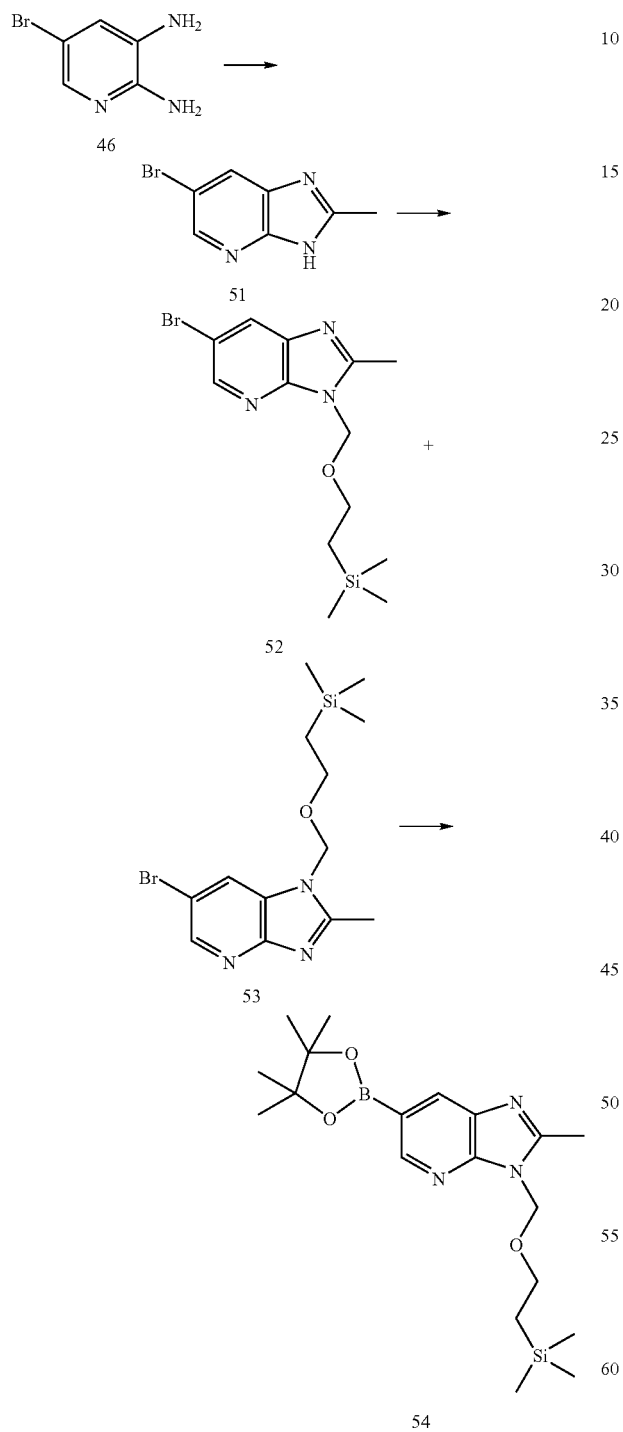

To 5.06 g of 5-bromo-2,3-diaminopyridine 46 (Ryabukhin et al (2006) Synthesis 21:3715-3726; Oguchi et al (2000) J. Med. Chem. 43(16):3052-3066; Seki et al (1995) J. Hetero. Chem. 32(3):1071-73; Fray et al (1995) J. Med. Chem. 38(18):3524-35) was added 50 mL acetic acid under $N_2$ and the reaction was heated to reflux overnight. Complete reaction was confirmed by LCMS. The solution was concentrated in vacuo and purified by flash chromatography (DCM/MeOH) to give 4.68 g of 6-bromo-2-methyl-3H-imidazo[4,5-b]pyridine 51 (82% yield), which may also be prepared by the methods of Cee et al (2007) J. Med. Chem. 50(4):627-40; Itoh et al (1982) J. Hetero. Chem. 19(3):513-17. 6-Bromo-2-methyl-3H-imidazo[4,5-b]pyridine (4.68 g) in 150 mL THF was added to 0.63 g (1.1 eq) NaH in 10 mL THF under $N_2$ at −78° C. The reaction was stirred at −78° C. for 30 minutes followed by the addition of 3.86 g of SEM-Cl (1.05 eq) and allowed to warm up to room temperature. The reaction was stirred at room temperature 4.5 hours and complete reaction was confirmed by LCMS. The reaction was quenched with water followed by the addition of NaCl (not saturated) and the two products extracted with EtOAc and concentrated in vacuo. The two regioisomers were separated by flash chromatography (EtOAc/Hexanes) to give 2.84 g 6-bromo-2-methyl-3-((2-(trimethylsilyl)ethoxy)methyl)-3H-imidazo[4,5-b]pyridine 52 and 1.94 g 6-bromo-2-methyl-1-((2-(trimethylsilyl)ethoxy)methyl)-1H-imidazo[4,5-b]pyridine 53 (63% overall yield). 6-Bromo-2-methyl-3-((2-(trimethylsilyl)ethoxy)methyl)-3H-imidazo[4,5-b]pyridine 52 (2.08 g) was dissolved in 50 mL toluene followed by the addition of 2.32 g (1.5 eq) of bis(pinacolato)diboron, 0.24 g (0.05 eq) of $PdCl_2(dppf)$, and 1.79 g (3.0 eq) of KOAc. The reaction mixture was heated to 95° C. under $N_2$ and let stir overnight. Complete reaction confirmed by LCMS. The mixture was cooled to room temperature, rotovapped and purified by flash chromatography (EtOAc/Hexanes) to give 1.83 g of 2-methyl-6-(4,4,5,5-tetramethyl-1,3,2-dioxaborolan-2-yl)-3-((2-(trimethylsilyl)ethoxy)methyl)-3H-imidazo[4,5-b]pyridine 54 (77% yield). MS (Q1) 390.2 (M)+

Example 10

1-(Tetrahydro-2H-pyran-2-yl)-4-(4,4,5,5-tetramethyl-1,3,2-dioxaborolan-2-yl)-1H-indazole 62 (Route A)

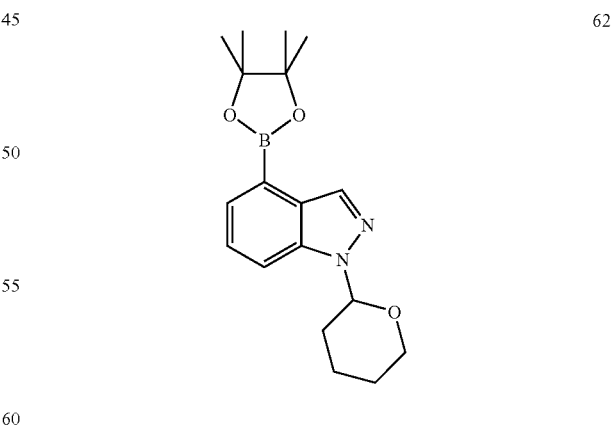

Step A: Preparation of 4-chloro-1H-indazole: To a 250 ml flask with stirbar was added 2-methyl-3-chloroaniline (8.4 ml, 9.95 g, 70.6 mmol), potassium acetate (8.3 g, 84.7 mmol) and chloroform (120 ml). This mixture was cooled to 0° C. with stirring. To the cooled mixture was added acetic anhydride (20.0 ml, 212 mmol) drop wise over 2 minutes. The reaction mixture was warmed to 25° C. and stirred for 1 hour.

At this point, the reaction was heated to 60° C. Isoamyl nitrite (18.9 ml, 141 mmol) was added and the reaction was stirred overnight at 60° C. Once complete, water (75 ml) and THF (150 ml) were added and the reaction was cooled to 0° C. LiOH (20.7 g, 494 mmol) was added and the reaction was stirred at 0° C. for 3 hours. Water (200 ml) was added and the product was extracted with EtOAc (300 ml, 100 ml). The organic layers were combined, dried with MgSO$_4$ and concentrated in vacuo to yield 11.07 g 4-chloro-1H-indazole (100%) as an orange solid. $^1$H NMR (400 MHz, CDCl$_3$) δ 8.18 (d, J=1 Hz, 1H), 7.33 (d, J=8 Hz 1H), 7.31 (t, J=7 Hz, 1H), 7.17 (dd, J=7 Hz, 1 Hz 1H). LCMS (ESI pos) m/e 153 (M+1).

Step B: Preparation of 4-chloro-1-(tetrahydro-2H-pyran-2-yl)-1H-indazole: To a 1 L flask with mechanical stirrer was added 4-chloro-1H-indazole (75.0 g, 0.492 mol), pyridinium p-toluenesulfonate (1.24 g, 4.92 mmol), CH$_2$Cl$_2$ (500 ml) and 3,4-dihydro-2H-pyran (98.6 ml, 1.08 mol). With stirring, this mixture was heated to 45° C. for 16 hours. Analysis of reaction mixture shows production of both isomers of product. Cooled reaction to 25° C. and added CH$_2$Cl$_2$ (200 ml). Washed the solution with water (300 ml) and saturated NaHCO$_3$ (250 ml). Dried the organics with MgSO$_4$ and concentrated to dryness. Purified the crude product by dissolving in EtOAc/Hexanes (4:6, 1 L) and adding SiO$_2$ (1.2 L). The mixture was filtered and the cake was washed with EtOAc/Hexanes (4:6, 2 L). The organics were concentrated in vacuo to yield 110.2 g 4-chloro-1-(tetrahydro-2H-pyran-2-yl)-1H-indazole (95%) as an orange solid. Isomer 1: $^1$H NMR (400 MHz, CDCl$_3$) δ 8.10 (d, J=1 Hz, 1H), 7.50 (dd, J=9 Hz, 1 Hz 1H), 7.29 (dd, J=9 Hz, 8 Hz 1H), 7.15 (dd, J=8 Hz, 1 Hz 1H) 5.71 (dd, J=9 Hz, 3 Hz 1H) 4.02 (m, 1H) 3.55 (m, 1H) 2.51 (m, 1H) 2.02 (m, 2H) 1.55 (m, 3H). LCMS (ESI pos) m/e 237 (M+1); Isomer 2: $^1$H NMR (400 MHz, CDCl$_3$) δ 8.25 (d, J=1 Hz, 1H), 7.62 (dd, J=9 Hz, 1 Hz 1H), 7.20 (dd, J=9 Hz, 8 Hz 1H), 7.06 (dd, J=8 Hz, 1 Hz 1H) 5.69 (dd, J=9 Hz, 3 Hz 1H) 4.15 (m, 1H) 3.80 (m, 1H) 2.22 (m, 2H) 2.05 (m, 1H) 1.75 (m, 3H). LCMS (ESI pos) m/e 237 (M+1).

Step C: Preparation of 1-(tetrahydro-2H-pyran-2-yl)-4-(4,4,5,5-tetramethyl-1,3,2-dioxaborolan-2-yl)-1H-indazole: To a 500 ml flask with stirbar was added 4-chloro-1-(tetrahydro-2H-pyran-2-yl)-1H-indazole (10.0 g, 42.2 mmol), DMSO (176 ml), PdCl$_2$(PPh$_3$)$_2$ (6.2 g, 8.86 mmol), tricyclohexylphosphine (0.47 g, 1.69 mmol), bis(pinacolato)diboron (16.1 g, 63.4 mmol) and potassium acetate (12.4 g, 0.127 mol). With stirring, the mixture was heated to 130° C. for 16 hours. The reaction was cooled to 25° C. and EtOAc (600 ml) was added and washed with water (2×250 ml). The organics were dried with MgSO$_4$ and concentrated in vacuo to dryness. The crude product was purified by SiO$_2$ plug (120 g), eluting with 10% EtOAc/Hexanes (IL) and 30% EtOAc/Hexanes (1 L). The filtrate was concentrated in vacuo to give 13.9 g 1-(tetrahydro-2H-pyran-2-yl)-4-(4,4,5,5-tetramethyl-1,3,2-dioxaborolan-2-yl)-1H-indazole (100%) of product 62 as a 20% (wt/wt) solution in ethyl acetate. $^1$H NMR shows the presence of ~20% (wt/wt) bis(pinacolato)diboron. $^1$H NMR (400 MHz, CDCl$_3$) δ 8.37 (s, 1H), 7.62 (dd, J=14 Hz, 2 Hz 1H), 7.60 (dd, J=7 Hz, 1 Hz 1H), 7.31 (dd, J=8 Hz, 7 Hz 1H) 5.65 (dd, J=9 Hz, 3 Hz 1H) 4.05 (m, 1H) 3.75 (m, 1H) 2.59 (m, 1H) 2.15 (m, 1H) 2.05 (m, 1H) 1.75 (m, 3H) 1.34 (s, 12H). LCMS (ESI pos) m/e 245 (M+1).

Example 11

1-(Tetrahydro-2H-pyran-2-yl)-4-(4,4,5,5-tetramethyl-1,3,2 dioxaborolan-2-yl)-1H-indazole 62 (Route B)

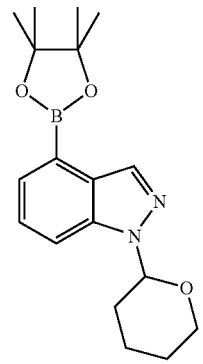

62

Step A: Preparation of 4-nitro-1H-indazole: A mixture of 2-methyl-3-nitro aniline (200 g, 1.315 moles), acetic acid (8000 ml) was cooled to 15-20° C. and a solution of sodium nitrite (90.6 g, 1.315 moles) in water (200 ml) was slowly added over 30 min. After the addition, the reaction temp. was increased to 25-30° C. and the reaction was stirred at this temp for 2-3 h. Reaction progress was monitored by TLC and after completion of reaction product was filtered and residue was washed with acetic acid (1000 ml). Acetic acid was distilled under vacuum (550 mm of Hg) below 80° C. and water (8000 ml) was added, cooled to 25-30° C. and stirred for 30 min. The slurry was filtered and washed with water (1000 ml). Crude product was dried under heating at 70-80° C. for 2 hours, then was taken in 5% ethyl acetate/n-hexane (100:2000 ml) solution and stirred for 1-1.5 h at ambient temperature. The suspension was filtered and washed with 5% ethyl acetate/n-hexane mixture (25:475 ml). The product obtained was dried under vacuum at below 80° C. for 10-12 h to give 4-nitro-1H-indazole as a brown solid (150 g, 70%): mp: 200-203° C.; $^1$H NMR (200 MHz, CDCl$_3$) δ 13.4 (br, 1H), 8.6 (s, 1H), 8.2-7.95 (dd, 2H), 7.4 (m, 1H). ESMS m/z 164 (M+1). Purity; 95% (HPLC)

Step B: Preparation of 4-amino-1H-indazole: A mixture of 4-nitro-1H-indazole (200 g, 1.22 moles) and 10% palladium on carbon (20.0 g,) in EtOH (3000 ml) was hydrogenated at ambient temperature (reaction was exothermic and temperature increased to 50° C.). After completion of reaction, the catalyst was removed by filtration. The solvent was evaporated under vacuum at below 80° C. and cooled to room temperature and n-hexane (1000 ml) was added to the residue and stirred for 30 min. Isolated solid was filtered and washed with n-hexane (200 ml). Product was dried under vacuum at 70-80° C. for 10-12 h to give 4-amino-1H-indazole as a brown solid (114 g, 70%), m. p.: 136-143° C. $^1$H NMR (200 MHz, CDCl$_3$) δ 12 (br, 1H), 8.0 (s, 1H), 7.1-7.0 (dd, 2H), 6.5 (d, 1H), 3.9 (m, 2H). ESMS m/z 134 (M+1). Purity: 90-95% (HPLC)

Step C: Preparation of 4-iodo-1H-indazole: A mixture of 4-amino-1H-indazole (50.0 g, 0.375 moles) in water (100 ml) and con. hydrochloric acid (182 ml) was cooled to −10° C. To this a solution of sodium nitrite (51.7 g, 0.75 moles) in water (75 ml) was added drop wise at −10° C. in about 30-60 min. (during addition frothing was observed). In another flask a mixture of potassium iodide (311 g, 1.87 moles) in water (3000 ml) was prepared at room temperature and to this above cooled diazonium salt at 30-40° C. was added in about 30-40 min. The reaction was maintained at 30° C. for 1 h and after completion of reaction, ethyl acetate (500 ml) was added and the reaction mixture was filtered through Celite. The layers were separated and the aq. layer was extracted with ethyl acetate (2×500 ml). The combined organic layers were washed with 5% hypo solution (2×500 ml), brine (500 ml), dried ($Na_2SO_4$) and concentrated. Crude product was purified by chromatography (silica gel, hexane, 15-20% ethyl acetate/hexane) to furnish 4-iodo-1H-indazole as an orange solid (23.0 g, 25%). m.p: 151-177 C: $^1H$ NMR (200 MHz, $CDCl_3$) δ 12.4 (br, 1H), 8.0 (s, 1H), 7.6 (dd, 2H), 7.1 (d, 1H). ESMS m/z 245 (M+1). Purity: 95-98% (HPLC).

Step D: Preparation of 4-iodo-1-(2-tetrahydropyranyl) indazole: A mixture of 4-amino-1H-indazole (250.0 g, 1.024 moles), 3,4-dihydro-2H-pyran (126.0 g, 1.5 moles) and PPTS (2.57 g, 0.01 moles) in $CH_2Cl_2$ (1250 ml) was heated to 50° C. for 2 h. The reaction was cooled to room temperature and poured into water (625 ml), the layers were separated, and aqueous layer was extracted with $CH_2Cl_2$ (250 ml). The combined organic layers were washed with water (625 ml), dried ($Na_2SO_4$) and concentrated. Crude residue was purified by chromatography (silica gel, hexane, 5-10% ethyl acetate/hexane) to furnish 4-iodo-1-(2-tetrahydropyranyl) indazole as an oil (807.0 g, 60%). $^1H$ NMR (200 MHz, $CDCl_3$) δ 8.5 (s, 1H), 7.8 (m, 1H), 7.6 (d, 1H), 7.25 (m, 1H), 5.7 (dd, 1H), 4.2-3.8 (dd, 1H), 2.2-2.0 (m, 4H) 2.0-1.8 (m, 4H). ESMS m/z 329 (M+1).

Step E: Preparation of 1-(tetrahydro-2H-pyran-2-yl)-4-(4, 4,5,5-tetramethyl-1,3,2-dioxaborolan-2-yl)-1H-indazole: A mixture of 4-iodo-1-(2-tetrahydropyranyl) indazole (100 g, 0.304 moles), bispinacalotodiborane (96.4 g, 0.381 moles), $PdCl_2$ (dppf) (8.91 g, 0.012 moles) and potassium acetate (85.97 g, 0.905 moles) in DMSO (500 ml) were heated to 80° C. for 2-3 h. After completion, reaction was cooled to room temperature and water (1500 ml) was added. Reaction mass was extracted into ethyl acetate (3×200 ml) and combined organic layers were evaporated, dried ($Na_2SO_4$) and concentrated. Crude product was purified by column chromatography (silica gel, hexane, 5-10% ethyl acetate/hexane) to obtain 1-(tetrahydro-2H-pyran-2-yl)-4-(4,4,5,5-tetramethyl-1,3,2-dioxaborolan-2-yl)-1H-indazole 62 as viscous brown oil (70.0 g, 70%). 5: $^1H$ NMR ($CDCl_3$) δ 8.5 (s, 1H), 7.8 (m, 1H), 7.6 (d, 1H), 7.25 (m, 1H), 5.7 (dd, 1H), 4.2-3.8 (dd, 1H), 2.2-2.0 (m, 4H) 2.0-1.8 (m, 4H) 1.4-1.2 (s, 12H). ESMS m/z 329 (M+1).

Example 12

(5-Chloro-7-morpholinothiazolo[4,5-d]pyrimidin-2-yl)methanol 56

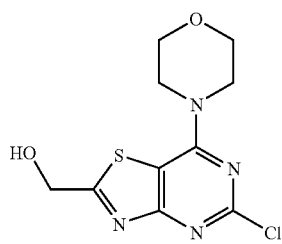

56

A solution of 5-chloro-7-morpholinothiazolo[4,5-d]pyrimidine-2-carbaldehyde 43 (1.0 g, 3.5 mmol) in MeOH (30 mL) at 0° C. was treated with $NaBH_4$ (0.1 g, 3.5 mmol). The solution was allowed to warm to room temperature and stirred 15 min. The reaction mixture was quenched with a mixture of a saturated solution of sodium bicarbonate and water (1:1, v/v). The aqueous solution was extracted with EtOAc. The combined organic layers were dried over $Na_2SO_4$ and concentrated in vacuo. The crude (5-chloro-7-morpholinothiazolo[4,5-d]pyrimidin-2-yl)methanol 56 required no further purification.

Example 13

4-(2-(Bromomethyl)-5-chlorothiazolo[4,5-d]pyrimidin-7-yl)morpholine 57

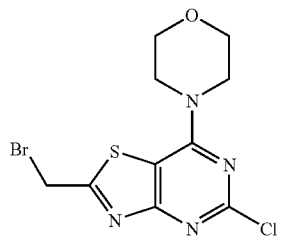

57

To a solution of (5-chloro-7-morpholinothiazolo[4,5-d]pyrimidin-2-yl)methanol 56 (100 mg, 0.4 mmol) in benzene (3.0 mL) at 0° C. was added $PBr_3$ (30 ΔL, 0.4 mmol). The reaction was heated at reflux for 1 hour. After cooling to room temperature the reaction was quenched by the addition of water. The aqueous layer was extracted with EtOAc. The combined organics were dried over $Na_2SO_4$ and concentrated in vacuo. The crude 4-(2-(bromomethyl)-5-chlorothiazolo[4, 5-d]pyrimidin-7-yl)morpholine 57 did not require further purification (x mg, x %). MS (Q1)×(M)+

Example 14

2-((5-Chloro-7-morpholinothiazolo[4,5-d]pyrimidin-2-yl)methyl)isoindoline-1,3-dione 58

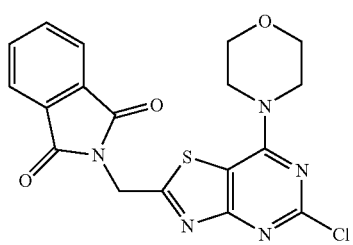

58

To a solution of 4-(2-(bromomethyl)-5-chlorothiazolo[4, 5-d]pyrimidin-7-yl)morpholine 57 in DMF was added $K_2CO_3$, and phthalimide. The resulting solution stirred 20 h at room temperature. The reaction was concentrated in vacuo and diluted with water (10 mL). The heterogeneous mixture was filtered to afford 2-((5-chloro-7-morpholinothiazolo[4, 5-d]pyrimidin-2-yl)methyl)isoindoline-1,3-dione 58.

Example 15

(5-Chloro-7-morpholinothiazolo[4,5-d]pyrimidin-2-yl)methanamine 59

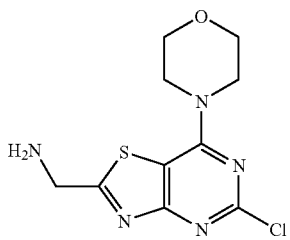

To a solution of 2-((5-chloro-7-morpholinothiazolo[4,5-d]pyrimidin-2-yl)methyl)isoindoline-1,3-dione 58 (100 mg, 0.24 mmol) in MeOH (7 mL) was added $H_2N-NH_2\cdot H_2O$. The reaction was heated at reflux for 1 h. After cooling to room temperature the reaction was quenched with water (10 mL) and extracted with EtOAc. The combined organics were dried over $Na_2SO_4$ and concentrated in vacuo to afford (5-chloro-7-morpholinothiazolo[4,5-d]pyrimidin-2-yl)methanamine 59.

Example 16

1-(5-Chloro-7-morpholinothiazolo[4,5-d]pyrimidin-2-yl)-N-methylmethanamine 60

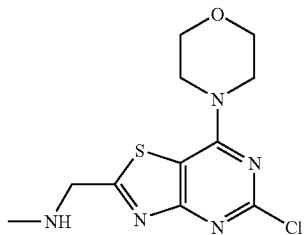

To 5-chloro-7-morpholinothiazolo[4,5-d]pyrimidine-2-carbaldehyde 43 in 50 mL Toluene and 50 mL THF was added 30 mL of $NH_2Me$ (40% in water) and the mixture stirred under $N_2$ for two days. The mixture was concentrated in vacuo and redissolved in 50 mL THF and 50 mL MeOH followed by the portionwise addition of 1.6 g (4.0 eq) $NaBH_4$ and the reaction mixture stirred overnight at room temperature. Complete reaction was confirmed by LCMS and the mixture was concentrated in vacuo and purified by flash chromatography (95/5% EtOAc/EtOH 20 min followed by a gradient up to 100% EtOH over 30 min more) to give 1-(5-chloro-7-morpholinothiazolo[4,5-d]pyrimidin-2-yl)-N-methylmethanamine 60.

Example 17

1-(5-Chloro-7-morpholinothiazolo[5,4-d]pyrimidin-2-yl)-N-methylmethanamine 61

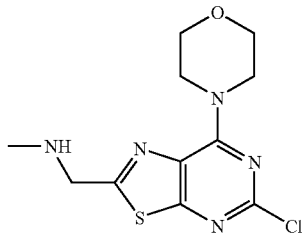

Also, to a solution of 5-chloro-7-morpholinothiazolo[5,4-d]pyrimidine-2-carbaldehyde 44 in 50 mL THF was added 20 mL of 40% methylamine in water. The reaction mixture was stirred at room temperature under $N_2$ for 24 hours. The solvents were removed in vacuo and the residue was dissolved in 50 mL MeOH and 50 mL THF and the $NaBH_4$ added portionwise. This reaction mixture was stirred at room temperature under $N_2$ for 24 hours and complete reaction was confirmed by LCMS. The solvents were removed in vacuo and the crude product purified by flash chromatography (EtOAc/EtOH) to give of 1-(5-chloro-7-morpholinothiazolo[5,4-d]pyrimidin-2-yl)-N-methylmethanamine 61.

Example 18

4-(5-Chloro-2-iodothiazolo[4,5-d]pyrimidin-7-yl)morpholine 27

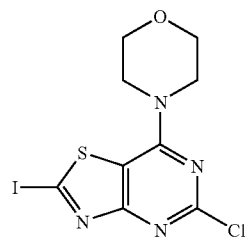

Following the procedures in U.S. Pat. No. 6,492,383, 2.5 M of n-butyllithium (9.4 mL, 22.48 mmol) in hexane solution was added to a mixture of 4-(5-chlorothiazolo[4,5-d]pyrimidin-7-yl)morpholine 16 (3.0 g, 11.74 mmol) in 60 mL of THF at −78° C. The reaction mixture was allowed to warm to −40° C. and stirred for 30 min. A solution of iodine (6.0 g, 23.48 mmol) in 10 mL of THF was added dropwise. After the addition was completed. The reaction mixture was brought to room temperature and stirred for 2 h. The mixture was quenched by diluting with dichloromethane and extracting with $H_2O$ (2×100 mL). The organic layer was washed with $Na_2S_2O_3$ (2×100 mL), $H_2O$ (2×100 mL), dried over $MgSO_4$, filtered and evaporated to afford 4-(5-chloro-2-iodothiazolo[4,5-d]pyrimidin-7-yl)morpholine 27.

Example 19 ethyl 2-phenyl-5-ureidothiazole-4-carboxylate 63

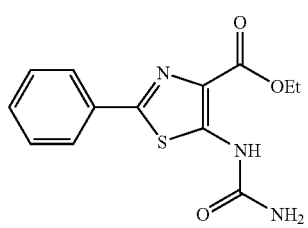

To a solution of ethyl 2-phenyl-5-aminothiazole-4-carboxylate (116 mg, 1.0 eq) in dichloromethane (3 ml) at −78° C. was added chlorosulfonyl isocyanate (0.06 ml, 1.3 eq) dropwise (Redman et al J. (2000) Org. Lett. 2:2061-2063). The reaction was slowly warmed to room temperature and stirred for 40 minutes. The reaction was concentrated. To the residue was added 6N HCl (2.5 ml) and mixture was heated to 100° C. for 20 minutes. Reaction mixture was allowed to cool down to room temperature, and was neutralized with saturated aq. $NaHCO_3$. Solid was collected by filtration to yield ethyl 2-phenyl-5-ureidothiazole-4-carboxylate 63 as a beige solid which was used in the next reaction without further purification.

Example 20

2-phenylthiazolo[5,4-d]pyrimidine-5,7-diol 64

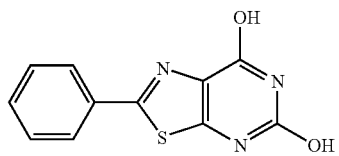

64

Ethyl 2-phenyl-5-ureidothiazole-4-carboxylate 63 (x mg, x eq) was suspended in methanol (5 ml) and treated with 1.5 M NaOH (1 ml). Reaction mixture was heated to reflux for 90 minutes. Reaction mixture was allowed to cool down to room temperature, and was acidified with 6N HCl up to pH 3. Solid was filtered and dried at 95° C. under high vacuum for 24 h to yield 2-phenylthiazolo[5,4-d]pyrimidine-5,7-diol 64 as a beige solid which was used in the next reaction without further purification.

Example 21

5,7-dichloro-2-phenylthiazolo[5,4-d]pyrimidine 65

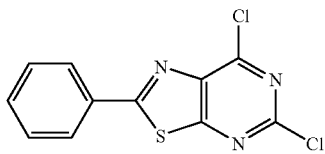

65

2-Phenylthiazolo[5,4-d]pyrimidine-5,7-diol 64 was dissolved in POCl$_3$ (xml). Mixture was cooled to −40° C. and N,N-diisopropylethylamine is slowly added. Reaction mixture was then heated to reflux for 48 h, then cooled to room temperature. The reaction mixture was poured into ice/water. Mixture was extracted with ethyl acetate. The combined organic layers were washed with saturated aq. NaHCO$_3$, dried (Na$_2$SO$_4$) and concentrated to yield 5,7-dichloro-2-phenylthiazolo[5,4-d]pyrimidine 65 which was used in the next reaction without further purification.

Example 22

4-(5-chloro-2-phenylthiazolo[5,4-d]pyrimidin-7-yl)morpholine 66

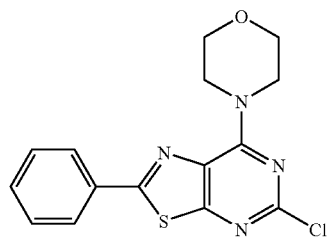

66

5,7-Dichloro-2-phenylthiazolo[5,4-d]pyrimidine 65 was suspended in methanol and treated with morpholine. The reaction mixture was stirred at room temperature for 4 h. Solid was filtered to yield pure 4-(5-chloro-2-phenylthiazolo[5,4-d]pyrimidin-7-yl)morpholine 66 as a beige solid.

Example 23

4-(5-chloro-2-iodothiazolo[5,4-d]pyrimidin-7-yl)morpholine 18

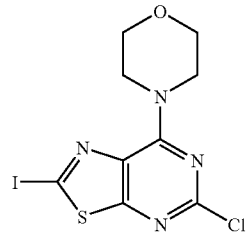

18

To a solution of 4-(5-chlorothiazolo[5,4-d]pyrimidin-7-yl)morpholine 14 dissolved in THF at −78° C. was added 1.6M solution of n-butyllithium in hexanes). The reaction mixture was stirred at −78° C. for 30 minutes. A solution of iodine in THF was added and reaction mixture was allowed to slowly warm up to room temperature and stirred for 45 minutes. The reaction mixture was quenched with saturated aq. Na$_2$S$_2$O$_3$, and extracted with dichloromethane. The combined organic layers were dried (Na$_2$SO$_4$) and concentrated. The crude reaction mixture was purified by flash chromatography to yield 4-(5-chloro-2-iodothiazolo[5,4-d]pyrimidin-7-yl)morpholine 18.

Example 24

2-(5-chloro-7-morpholinothiazolo[5,4-d]pyrimidin-2-yl)propan-2-ol 68

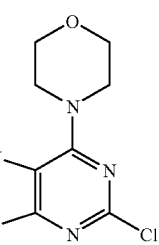

68

4-(5-Chlorothiazolo[5,4-d]pyrimidin-7-yl)morpholine 14 was slurried in tetrahydrofuran and cooled to −78° C. under nitrogen. Two equivalents of 2M lithium diisopropylamide in heptane/tetrahydrofuran/ethylbenzene was added slowly and the solution was stirred for 30 minutes. Acetone (6 eq) was added and the solution was stirred at −78° C. for an additional one hour. Ice was added and the solution was warmed to room temperature before extraction with methylene chloride. The organic layer was dried with sodium sulfate and concentrated. The resulting residue was purified on silica gel to give the light yellow solid of 2-(5-chloro-7-morpholinothiazolo[5,4-d]pyrimidin-2-yl)propan-2-ol 68.

Example 25

5-(1H-indazol-4-yl)-7-morpholinothiazolo[4,5-d]pyrimidine-2-carbaldehyde 55

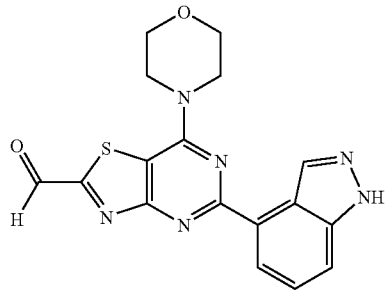

A mixture of 5-chloro-7-morpholinothiazolo[4,5-d]pyrimidine-2-carbaldehyde 43, 4-(4,4,5,5-tetramethyl-[1,3,2]dioxaborolan-2-yl)-1H-indazole 1 and sodium carbonate were suspended in toluene, ethanol and water. To this was added bis(triphenylphosphine)palladium(II) chloride and the reaction vessel was flushed with argon. The reaction mixture was microwaved at 120° C. for 1 h and then partitioned between DCM and water. The organic layer was washed with brine, dried over magnesium sulfate, filtered and evaporated in vacuo. The resulting residue was purified using flash chromatography to yield 5-(1H-indazol-4-yl)-7-morpholinothiazolo[4,5-d]pyrimidine-2-carbaldehyde 55.

Example 26

N-methyl-5-(2-((4-(methylsulfonyl)piperazin-1-yl)methyl)-7-morpholinothiazolo[5,4-d]pyrimidin-5-yl)pyridin-2-amine 101

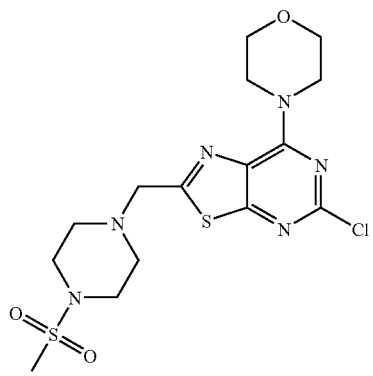

5-Chloro-2-(4-methanesulfonyl-piperazin-1-ylmethyl)-7-morpholin-4-yl-thiazolo[5,4-d]pyrimidine 74 (90 mg) was reacted with 100 mg of N-Boc-aminomethylpyridine boronate ester via General Procedure A to yield crude {5-[2-(4-methanesulfonyl-piperazin-1-ylmethyl)-7-morpholin-4-yl-thiazolo[5,4-d]pyrimidin-5-yl]-pyridin-2-yl}-methyl-carbamic acid tert-butyl ester 75 (100 mg).

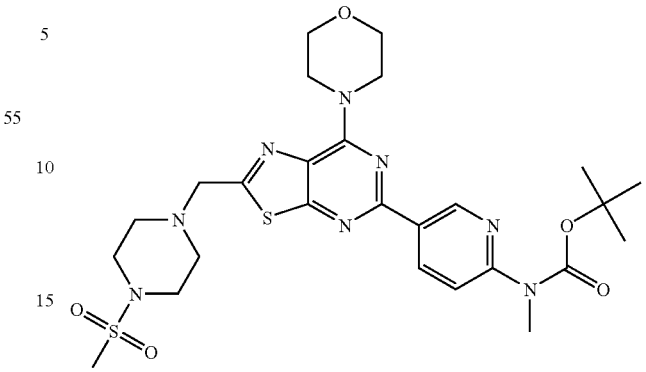

Crude {5-[2-(4-methanesulfonyl-piperazin-1-ylmethyl)-7-morpholin-4-yl-thiazolo[5,4-d]pyrimidin-5-yl]-pyridin-2-yl}-methyl-carbamic acid tert-butyl ester 75 (100 mg) was dissolved in a solution of 1 mL of trifluoroacetic acid and 1 mL of dichloromethane. The reaction mixture was stirred for 1 h. The mixture was concentrated. The product was purified by reverse phase HPLC to yield 53.8 mg of 101. MS (Q1) 505.2 (M)$^+$.

Example 27

5-(2-(2-methoxypropan-2-yl)-7-morpholinothiazolo[5,4-d]pyrimidin-5-yl)-N-methylpyridin-2-amine 102

Tert-butyl 5-bromopyridin-2-ylcarbamate (10 g) and cesium carbonate (20 g) were added to 50 mL of DMF. Methyl iodide (4 mL) was subsequently slowly added to the stirring reaction mixture. After 30 minutes tlc indicates that the reaction is complete. The majority of the DMF was removed under hi-vacuum and the reaction mixture was extracted with ethyl acetate and water. The organic layer was dried, filtered and concentrated. The crude product was purified by Isco 0-30% gradient (H/E) over 25 mins. The tubes were pooled and concentrated to get 9.85 g of tert-butyl 5-bromopyridin-2-yl(methyl)carbamate as a clear oil.

To a solution of 9.5 g tert-butyl 5-bromopyridin-2-yl(methyl)carbamate in 60 mL DMSO was added 13 g bi-pinacolatodiboron, 9.7 g KOAc and 1.4 g [1,1'-bis(diphenylphosphino)ferrocene]dichloropalladium(II), complex with dichloromethane (1:1) and the reaction was heated at 80° C. overnight. Next day the LC-MS shows starting material is consumed and reaction is complete. The reaction was cooled to room temperature and then added to water and extracted with ethyl acetate. The organic layer was dried, filtered and concentrated to give a black oil. The crude material was purified in 2 batches via 120 g chromatography (ISCO) columns. The fractions were pooled and concentrated to give crystalline white solid. NMR shows 30% residual bispinnacolatodiboron and the rest is desired tert-butyl 5-bromopyridin-2-yl(methyl)carbamate. This mixture is used in subsequent Suzuki couplings.

Crude 4-(5-chloro-2-(2-methoxypropan-2-yl)thiazolo[5,4-d]pyrimidin-7-yl)morpholine (60 mg) was reacted with tert-butyl methyl(5-(4,4,5,5-tetramethyl-1,3,2-dioxaborolan-2-yl)pyridin-2-yl)carbamate via general procedure A. This crude product was then treated with TFA to remove residual protecting group and purified via reverse phase HPLC to get 58.4 mg 102. MS (Q1) 401.2 (M)+.

Example 28

5-(2-(2-methoxypropan-2-yl)-7-morpholinothiazolo[5,4-d]pyrimidin-5-yl)-N-methylpyrimidin-2-amine 103

Crude 4-(5-chloro-2-(2-methoxypropan-2-yl)thiazolo[5,4-d]pyrimidin-7-yl)morpholine (60 mg) was reacted with 2-(tert-butoxycarbonylamino)methylpyrimidine-5-boronic acid via general procedure A. This crude product was then treated with TFA to remove residual protecting group and purified via reverse phase HPLC to get 43.8 mg 103. MS (Q1) 402.2 (M)+.

Example 29

5-(2-(2-methoxypropan-2-yl)-7-morpholinothiazolo[5,4-d]pyrimidin-5-yl)pyrimidin-2-amine 104

2-(5-Chloro-7-morpholinothiazolo[5,4-d]pyrimidin-2-yl)propan-2-ol 68 (175 mg) was cooled in DMF to 0° C. and then NaH was added at once. The reaction was allowed to warm to room temperature and stirred several minutes before addition of methyl iodide. Reaction was stirred several hours and monitored by LC-MS until complete. Ethyl acetate was added and the solution was extracted with saturated bicarbonate solution. Organic was collected and dried, filtered and concentrated to get crude 4-(5-chloro-2-(2-methoxypropan-2-yl)thiazolo[5,4-d]pyrimidin-7-yl)morpholine.

Crude 4-(5-chloro-2-(2-methoxypropan-2-yl)thiazolo[5,4-d]pyrimidin-7-yl)morpholine (60 mg) was reacted with 2-aminopyrimidine-5-boronic acid pinacol ester via general procedure A with to get 55 mg 104 following reverse phase HPLC purification. MS (Q1) 388.2 (M)+.

Example 30

N-methyl-5-(2-(3-(methylsulfonyl)phenyl)-7-morpholinothiazolo[5,4-d]pyrimidin-5-yl)pyridin-2-amine 105

A mixture of 4-(5-chloro-2-iodothiazolo[5,4-d]pyrimidin-7-yl)morpholine 18 (400 mg, 1 mmol), 3-methylsulfonylphenylboronic acid (230 mg, 1.1 mmol), bis (triphenylphosphine)palladium(II) dichloride (37 mg, 0.052 mmol) in 4 ml of acetonitrile and 4 mL of 1.0 M of sodium carbonate aqueous solution was heated to 100° C. in the microwave for 10 min. Water (5 mL) was added and the resulting solid was filtered and washed with water and ethyl acetate to yield crude 5-chloro-2-(3-methanesulfonyl-phenyl)-7-morpholin-4-yl-thiazolo[5,4-d]pyrimidine (400 mg).

5-Chloro-2-(3-methanesulfonyl-phenyl)-7-morpholin-4-yl-thiazolo[5,4-d]pyrimidine (100 mg) was reacted with 98 mg of N-Boc-aminomethylpyridine boronate ester via General Procedure A. The product was purified by reverse phase HPLC to yield 33 mg of 105. MS (Q1) 483.2 (M)+.

Example 31

(S)-2-hydroxy-1-(4-((7-morpholino-5-(quinolin-3-yl)thiazolo[5,4-d]pyrimidin-2-yl)methyl)piperazin-1-yl)propan-1-one 106

A mixture of 5-chloro-7-morpholin-4-yl-2-piperazin-1-ylmethyl-thiazolo[5,4-d]pyrimidine with HCl salt (1 g, 2.6 mmol), L-(+)-lactic acid (460 mg, 5.1 mmol), HATU (1.9 g, 5.1 mmol) and N,N-diisopropylethylamine (1.4 mL, 7.8 mmol) in 8 mL of DMF was stirred overnight. The mixture was diluted with ethyl acetate, and washed with saturated sodium bicarbonate aqueous solution and brine. The organic layer was dried over magnesium sulfate, filtered and evaporated to yield the crude 1-[4-(5-Chloro-7-morpholin-4-yl-thiazolo[5,4-d]pyrimidin-2-ylmethyl)-piperazin-1-yl]-2-hydroxy-propan-1-one (900 mg).

1-[4-(5-Chloro-7-morpholin-4-yl-thiazolo[5,4-d]pyrimidin-2-ylmethyl)-piperazin-1-yl]-2-hydroxy-propan-1-one (100 mg) was reacted with 72 mg of 3-(4,4,5,5-tetramethyl-1,3,2,-dioxaborolan-2-yl)quinoline via General Procedure A. The product was purified by reverse phase HPLC to yield 43.5 mg of 106. MS (Q1) 520.3 (M)+.

Example 32

(S)-2-hydroxy-1-(4-((5-(2-(methylamino)pyrimidin-5-yl)-7-morpholinothiazolo[5,4-d]pyrimidin-2-yl)methyl)piperazin-1-yl)propan-1-one 107

Methyl iodide (390 µL, 6.2 mmol) was added to a mixture of 2-(tert-butoxycarbonylamino)pyrimidine-5-boronic acid, pinacol ester (1 g, 3 mmol) and cesium carbonate (2.0 mg, 6.2 mmol) in N,N-dimethylformamide (15 mL, 190 mmol). The reaction mixture was stirred at room temperature for 1 h. Water (20 mL) was added. The mixture was neutralized to pH 7 using 1N HCl, then extracted with ethyl acetate (3×60 mL). The combined organic layers were dried over magnesium sulfate, filtered and evaporated to yield crude 2-(tert-butoxycarbonylamino)methylpyrimidine-5-boronic acid (560 mg).

1-[4-(5-Chloro-7-morpholin-4-yl-thiazolo[5,4-d]pyrimidin-2-ylmethyl)-piperazin-1-yl]-2-hydroxy-propan-1-one (80 mg) was reacted with 56 mg of 2-(tert-butoxycarbonylamino)methylpyrimidine-5-boronic acid via General Procedure A. The product was purified by reverse phase HPLC to yield 24.1 mg of 107. MS (Q1) 500.3 (M)+.

Example 33

(S)-1-(4-((5-(2-aminopyrimidin-5-yl)-7-morpholinothiazolo[5,4-d]pyrimidin-2-yl)methyl)piperazin-1-yl)-2-hydroxypropan-1-one 108

1-[4-(5-Chloro-7-morpholin-4-yl-thiazolo[5,4-d]pyrimidin-2-ylmethyl)-piperazin-1-yl]-2-hydroxy-propan-1-one (100 mg) was reacted with 62 mg of 2-aminopyrimidine-5-boronic acid, pinacol ester via General Procedure A. The product was purified by reverse phase HPLC to yield 28 mg of 108. MS (Q1) 486.2 (M)+.

Example 34

4-(2-(3-(methylsulfonyl)phenyl)-5-(1H-pyrrolo[2,3-b]pyridin-5-yl)thiazolo[5,4-d]pyrimidin-7-yl)morpholine 109

5-Chloro-2-(3-methanesulfonyl-phenyl)-7-morpholin-4-yl-thiazolo[5,4-d]pyrimidine (80 mg) was reacted with 54 mg of 5-(4,4,5,5-tetramethyl-[1,3,2]dioxaborolan-2-yl)-1H-pyrrolo[2,3-b]pyridine via General Procedure A. The product was purified by reverse phase HPLC to yield 41.8 mg of 109. MS (Q1) 493.2 (M)+.

Example 35

N,N-dimethyl-5-(2-((4-(methylsulfonyl)piperazin-1-yl)methyl)-7-morpholinothiazolo[5,4-d]pyrimidin-5-yl)pyrimidin-2-amine 110

5-Chloro-2-(4-methanesulfonyl-piperazin-1-ylmethyl)-7-morpholin-4-yl-thiazolo[5,4-d]pyrimidine (80 mg) was reacted with 55 mg of dimethyl-[5-(4,4,5,5-tetramethyl-[1,3, 2]dioxaborolan-2-yl)-pyrimidin-2-yl]-amine via General Procedure A. The product was purified by reverse phase HPLC to yield 10.3 mg of 110. MS (Q1) 520.2 (M)$^+$.

Example 36

5-(2-((4-(methylsulfonyl)piperazin-1-yl)methyl)-7-morpholinothiazolo[5,4-d]pyrimidin-5-yl)pyridin-2-amine 111

5-Chloro-2-(4-methanesulfonyl-piperazin-1-ylmethyl)-7-morpholin-4-yl-thiazolo[5,4-d]pyrimidine (80 mg) was reacted with 49 mg of 5-(4,4,5,5-tetramethyl-[1,3,2]dioxaborolan-2-yl)-pyridin-2-ylamine via General Procedure A. The product was purified by reverse phase HPLC to yield 24.3 mg of 111. MS (Q1) 491.0 (M)$^+$.

Example 37

4-(2-((4-(methylsulfonyl)piperazin-1-yl)methyl)-5-(quinolin-3-yl)thiazolo[5,4-d]pyrimidin-7-yl)morpholine 112

5-Chloro-2-(4-methanesulfonyl-piperazin-1-ylmethyl)-7-morpholin-4-yl-thiazolo[5,4-d]pyrimidine (130 mg) was reacted with 92 mg of 3-(4,4,5,5-tetramethyl-1,3,2,-dioxaborolan-2-yl)quinoline via General Procedure A. The product was purified by reverse phase HPLC to yield 72.6 mg of 112. MS (Q1) 526.2 (M)$^+$.

Example 38

N-methyl-5-(2-((4-(methylsulfonyl)piperazin-1-yl)methyl)-7-morpholinothiazolo[5,4-d]pyrimidin-5-yl)pyrimidin-2-amine 113

5-Chloro-2-(4-methanesulfonyl-piperazin-1-ylmethyl)-7-morpholin-4-yl-thiazolo[5,4-d]pyrimidine (80 mg) was reacted with 56 mg of 2-(tert-butoxycarbonylamino)methylpyrimidine-5-boronic acid via General Procedure A. The product was purified by reverse phase HPLC to yield 17.3 mg of 113. MS (Q1) 506.2 (M)$^+$.

Example 39

N-(3-(5-(2-(methylamino)pyrimidin-5-yl)-7-morpholinothiazolo[5,4-d]pyrimidin-2-yl)benzyl)methanesulfonamide 114

A mixture of 4-(5-chloro-2-iodothiazolo[5,4-d]pyrimidin-7-yl)morpholine 18 (400 mg, 1 mmol), 3-methanesulphonylaminomethyl benzeneboronic acid (260 mg, 1.1 mmol), bis(triphenylphosphine)palladium(II) dichloride (37 mg, 0.052 mmol) in 4 ml of acetonitrile and 4 mL of 1.0 M of sodium carbonate aqueous solution was heated to 100° C. in a microwave for 10 min. Water (5 mL) was added and the resulting solid was filtered and washed with water and ethyl acetate to yield crude N-[3-(5-Chloro-7-morpholin-4-yl-thiazolo[5,4-d]pyrimidin-2-yl)-benzyl]-methanesulfonamide (400 mg).

N-[3-(5-Chloro-7-morpholin-4-yl-thiazolo[5,4-d]pyrimidin-2-yl)-benzyl]-methanesulfonamide (100 mg) was reacted with 100 mg of 2-(tert-butoxycarbonylamino)methylpyrimidine-5-boronic acid via General Procedure A. The product was purified by reverse phase HPLC to yield 114. MS (Q1) 513.2 (M)$^+$.

Example 40

N-(3-(7-morpholino-5-(1H-pyrrolo[2,3-b]pyridin-5-yl)thiazolo[5,4-d]pyrimidin-2-yl)benzyl)methanesulfonamide 115

N-[3-(5-Chloro-7-morpholin-4-yl-thiazolo[5,4-d]pyrimidin-2-yl)-benzyl]-methanesulfonamide (120 mg) was reacted with 80 mg of 5-(4,4,5,5-tetramethyl-[1,3,2]dioxaborolan-2-yl)-1H-pyrrolo[2,3-b]pyridine via General Procedure A. The product was purified by reverse phase HPLC to yield 45 mg of 115. MS (Q1) 522.2 (M)$^+$.

Example 41

4-(2-((4-(methylsulfonyl)piperazin-1-yl)methyl)-5-(1H-pyrrolo[2,3-b]pyridin-5-yl)thiazolo[5,4-d]pyrimidin-7-yl)morpholine 116

5-Chloro-2-((4-methylsulfonylpiperazin-1-yl)methyl)-7-morpholinothiazolo[5,4-d]pyrimidine, 1H-pyrrolo[2,3-b]pyridin-5-yl boronic acid (1.2 eq), and trans-dichlorobis(triphenylphosphine)palladium(II) (0.1 eq) were slurried with equal parts 1M sodium carbonate (3 eq) and acetonitrile. The solution was microwaved at 130° C. for 15 minutes. Acetonitrile was added and the solution was filtered. The resulting organic layer was purified by reverse phase silica gel chromatography to give the product 116.

Example 42

5-(2-aminopyrimidin-5-yl)-7-morpholino-N-(4-morpholinophenyl)thiazolo[5,4-d]pyrimidin-2-amine 117

4-(5-Chloro-2-iodothiazolo[5,4-d]pyrimidin-7-yl)morpholine 18 was reacted with 4-morpholinoaniline via General Procedure B to give, after purification, 5-chloro-7-morpholino-N-(4-morpholinophenyl)thiazolo[5,4-d]pyrimidin-2-amine, which was then reacted with 5-(4,4,5,5-tetramethyl-1,3,2-dioxaborolan-2-yl)pyrimidin-2-amine via General Procedure B again to give 117 after purification by reverse HPLC. MS (Q1) 492 (M$^+$)

Example 43

5-(2-aminopyrimidin-5-yl)-N-(4-(methylsulfonyl)phenyl)-7-morpholinothiazolo[5,4-d]pyrimidin-2-amine 118

4-(5-Chloro-2-iodothiazolo[5,4-d]pyrimidin-7-yl)morpholine 18 was reacted with 4-methylsulfonylaniline via General Procedure B to give, after purification, 5-chloro-N-(4-(methylsulfonyl)phenyl)-7-morpholinothiazolo[5,4-d]pyrimidin-2-amine, which was then reacted with 5-(4,4,5,5-tetramethyl-1,3,2-dioxaborolan-2-yl)pyrimidin-2-amine via General Procedure B again to give 118 after purification by reverse HPLC. MS (Q1) 485 (M$^+$)

Example 44

5-(2-aminopyrimidin-5-yl)-7-morpholino-N-phenylthiazolo[5,4-d]pyrimidin-2-amine 119

4-(5-Chloro-2-iodothiazolo[5,4-d]pyrimidin-7-yl)morpholine 18 was reacted with aniline via General Procedure B to give, after purification, 5-chloro-7-morpholino-N-phenylthiazolo[5,4-d]pyrimidin-2-amine, which was then reacted with 5-(4,4,5,5-tetramethyl-1,3,2-dioxaborolan-2-yl)pyrimidin-2-amine via General Procedure B again to give 119 after purification by reverse HPLC. MS (Q1) 407 (M+)

Example 45

5-(2-(5-(methylsulfonyl)pyridin-3-yl)-7-morpholinothiazolo[5,4-d]pyrimidin-5-yl)pyrimidin-2-amine 120

4-(5-Chloro-2-iodothiazolo[5,4-d]pyrimidin-7-yl)morpholine 18 was reacted with 5-(methylsulfonyl)pyridin-3-yl-3-boronic acid via General Procedure A to give crude 5-chloro-2-(5-(methylsulfonyl)pyridin-3-yl)-7-morpholinothiazolo[5, 4-4]pyrimidine, which was then reacted with 5-(4,4,5,5-tetramethyl-1,3,2-dioxaborolan-2-yl)pyrimidin-2-amine via General Procedure A again to give 120 after purification by reverse HPLC. MS (Q1) 471 (M+)

Example 46

N-(3-(5-(2-aminopyrimidin-5-yl)-7-morpholinothiazolo[5,4-d]pyrimidin-2-yl)phenyl)methanesulfonamide 121

4-(5-Chloro-2-iodothiazolo[5,4-d]pyrimidin-7-yl)morpholine 18 was reacted with 3-(methylsulfonylamino)phenylboronic acid via General Procedure A to give crude 3-(5-chloro-7-morpholinothiazolo[5,4-d]pyrimidin-2-yl)-N-methylsulfonylbenzenamine, which was then reacted with 5-(4,4,5,5-tetramethyl-1,3,2-dioxaborolan-2-yl)pyrimidin-2-amine via General Procedure A again to give 121 after purification by reverse HPLC. MS (Q1) 485 (M+)

Example 47

5-(2-((4-(methylsulfonyl)piperazin-1-yl)methyl)-7-morpholinothiazolo[5,4-d]pyrimidin-5-yl)pyrimidin-2-amine 122

5-Chloro-2-((4-methylsulfonylpiperazin-1-yl)methyl)-7-morpholinothiazolo[5,4-d]pyrimidine,5-pyrimidine-2-amine boronic acid (1.2 eq), and trans-dichlorobis(triphenylphosphine)palladium(II) (0.1 eq) were slurried with equal parts 1M sodium carbonate (3 eq) and acetonitrile. The solution was microwaved at 130° C. for 8 minutes. The solvents were removed and the resulting residue was purified by reverse phase silica gel chromatography to give 122.

Example 48

5-(7-morpholino-2-(6-morpholinopyridin-3-yl)thiazolo[5,4-d]pyrimidin-5-yl)pyrimidin-2-amine 123

4-(5-Chloro-2-iodothiazolo[5,4-d]pyrimidin-7-yl)morpholine 18 was reacted with 4-(5-(4,4,5,5-tetramethyl-1,3,2-dioxaborolan-2-yl)pyridin-2-yl)morpholine via General Procedure A to give crude 5-chloro-7-morpholino-2-(6-morpholinopyridin-3-yl)thiazolo[5,4-d]pyrimidine, which was then reacted with 5-(4,4,5,5-tetramethyl-1,3,2-dioxaborolan-2-yl)pyrimidin-2-amine via General Procedure A again to give 123 after purification by reverse HPLC. MS (Q1) 478 (M+)

Example 49

N-(3-(5-(2-aminopyrimidin-5-yl)-7-morpholinothiazolo[5,4-d]pyrimidin-2-yl)phenyl)acetamide 124

4-(5-Chloro-2-iodothiazolo[5,4-d]pyrimidin-7-yl)morpholine 18 was reacted with (3-acetylaminophenyl)boronic acid via General Procedure A to give crude N-(3-(5-chloro-7-morpholinothiazolo[5,4-d]pyrimidin-2-yl)phenyl)acetamide, which was then reacted with 5-(4,4,5,5-tetramethyl-1,3,2-dioxaborolan-2-yl)pyrimidin-2-amine via General Procedure A again to give 124. MS (Q1) 449 (M+)

Example 50

N-(4-(5-(2-aminopyrimidin-5-yl)-7-morpholinothiazolo[5,4-d]pyrimidin-2-yl)phenyl)methanesulfonamide 125

4-(5-Chloro-2-iodothiazolo[5,4-d]pyrimidin-7-yl)morpholine 18 was reacted with N-methylsulfonyl-4-(4,4,5,5-tetramethyl-1,3,2-dioxaborolan-2-yl)benzenamine via General Procedure A to give crude 4-(5-chloro-7-morpholinothiazolo[5,4-d]pyrimidin-2-yl)-N-methylsulfonylbenzenamine, which was then reacted with 5-(4,4,5,5-tetramethyl-1,3,2-dioxaborolan-2-yl)pyrimidin-2-amine via General Procedure A again to give 125 after purification by reverse HPLC. MS (Q1) 485 (M+)

Example 51

N-(3-(5-(2-aminopyrimidin-5-yl)-7-morpholinothiazolo[5,4-d]pyrimidin-2-yl)benzyl)methanesulfonamide 126

4-(5-Chloro-2-iodothiazolo[5,4-d]pyrimidin-7-yl)morpholine 18 was reacted with 3-((methylsulfonylamino)methyl)phenylboronic acid via General Procedure A to give crude (3-(5-chloro-7-morpholinothiazolo[5,4-d]pyrimidin-2-yl)phenyl)-N-methylsulfonylmethanamine, which was then reacted with 5-(4,4,5,5-tetramethyl-1,3,2-dioxaborolan-2-yl)pyrimidin-2-amine via General Procedure A again to give 126 after purification by reverse HPLC. MS (Q1) 499 (M+)

Example 52

5-(2-(6-aminopyridin-3-yl)-7-morpholinothiazolo[5,4-d]pyrimidin-5-yl)pyrimidin-2-amine 127

4-(5-Chloro-2-iodothiazolo[5,4-d]pyrimidin-7-yl)morpholine 18 was reacted with 5-(4,4,5,5-tetramethyl-1,3,2-dioxaborolan-2-yl)pyridin-2-amine via General Procedure A to give crude 5-(5-chloro-7-morpholinothiazolo[5,4-d]pyrimidin-2-yl)pyridin-2-amine, which was then reacted with 5-(4,4,5,5-tetramethyl-1,3,2-dioxaborolan-2-yl)pyrimidin-2-amine via General Procedure A again to give 127 after purification by reverse HPLC. MS (Q1) 408 (M+)

Example 53

5-(2-(4-methoxypyridin-3-yl)-7-morpholinothiazolo[5,4-d]pyrimidin-5-yl)pyrimidin-2-amine 128

4-(5-Chloro-2-iodothiazolo[5,4-d]pyrimidin-7-yl)morpholine 18 was reacted with 4-methoxypyridin-3-yl-3-boronic acid via General Procedure A to give crude 5-chloro-2-(4-methoxypyridin-3-yl)-7-morpholinothiazolo[5,4-d]pyrimidine, which was then reacted with 5-(4,4,5,5-tetramethyl-1,3,2-dioxaborolan-2-yl)pyrimidin-2-amine via General Procedure A again to give 128 after purification by reverse HPLC. MS (Q1) 423 (M+)

Example 54

4-(5-(1H-indazol-4-yl)-2-((4-(methylsulfonyl)piperazin-1-yl)methyl)thiazolo[5,4-d]pyrimidin-7-yl)morpholine 129

5-Chloro-7-morpholinothiazolo[5,4-d]pyrimidine was slurried in tetrahydrofuran and cooled to −78° C. under nitrogen. Two equivalents of 2M lithium diisopropylamide in heptane/tetrahydrofuran/ethylbenzene was added slowly and the solution was stirred for 30 minutes. dimethylformamide (6 eq) was added and the solution was stirred at −78° C. for an additional one hour. The solution was warmed to 0° C. and ice cold 0.1N hydrochloric acid was added and the solution was warmed to room temperature before extraction with methylene chloride. The organic layer was dried with sodium sulfate and concentrated to give 5-chloro-7-morpholinothiazolo[5,4-d]pyrimidine-2-carbaldehyde.

5-Chloro-7-morpholinothiazolo[5,4-d]pyrimidine-2-carbaldehyde was dissolved in dichloroethane with 1-methylsulfonylpiperazine hydrochloride (1.45 eq), sodium acetate (1.45 eq), and trimethylorthoformate (1.45 eq). The solution was stirred overnight. Sodium triacetoxyborohydride (1.35 eq) was added and after three hours at room temperature the reaction was quenched with saturated sodium bicarbonate solution. The aqueous was extracted with methylene chloride, dried with sodium sulfate and purified by silica gel chromatography to give 5-chloro-2-((4-methylsulfonylpiperazin-1-yl)methyl)-7-morpholinothiazolo[5,4-d]pyrimidine.

5-Chloro-2-((4-methylsulfonylpiperazin-1-yl)methyl)-7-morpholinothiazolo[5,4-d]pyrimidine, 1H-indazol-4-yl-4-boronic acid (1.2 eq), and trans-dichlorobis(triphenylphosphine)palladium(II) (0.1 eq) were combined in a solution of equal parts sodium carbonate aqueous solution (1M, 3 eq) and acetonitrile. The solution was microwaved at 130° C. for eighteen minutes. An additional 0.1 equivalents of trans-dichlorobis(triphenylphosphine)palladium(II) was added and the solution was microwaved at 130° C. for an additional twenty minutes. Acetonitrile was added and the solution was filtered. The organic layer was purified by reverse phase chromatography to give the off white solid of 129.

Example 55

2-(5-(2-aminopyrimidin-5-yl)-7-morpholinothiazolo[5,4-d]pyrimidin-2-yl)propan-2-ol 130

2-(5-Chloro-7-morpholinothiazolo[5,4-d]pyrimidin-2-yl)propan-2-ol, 5-pyrimidine-2-amine boronic acid 68 (1.2 eq), and trans-dichlorobis(triphenylphosphine)palladium(II) (0.1 eq) were slurried with equal parts 1M sodium carbonate aqueous solution (3 eq) and acetonitrile. The solution was microwaved at 130° C. for 15 minutes. The solution was evaporated to dryness and purified by reverse phase silica gel chromatography to give the product 130.

Example 56

5-(7-morpholinothiazolo[5,4-d]pyrimidin-5-yl)pyrimidin-2-amine 131

4-(5-Chlorothiazolo[5,4-d]pyrimidin-7-yl)morpholine 14 was reacted with 5-(4,4,5,5-tetramethyl-1,3,2-dioxaborolan-2-yl)pyrimidin-2-amine via General Procedure A to give 131 after purification by reverse HPLC.

Example 57

5-(2-(3-(methylsulfonyl)phenyl)-7-morpholinothiazolo[5,4-d]pyrimidin-5-yl)pyrimidin-2-amine 132

5-Chloro-2-iodo-7-morpholinothiazolo[5,4-d]pyrimidine was reacted with 3-(methylsulfonyl)phenylboronic acid via General Procedure A to give crude 5-chloro-2-(3-(methylsulfonyl)phenyl)-7-morpholinothiazolo[5,4-d]pyrimidine, which was then reacted with 5-(4,4,5,5-tetramethyl-1,3,2-dioxaborolan-2-yl)pyrimidin-2-amine via General Procedure A again to give 132 after purification by reverse HPLC. MS (Q1) 470 (M+)

Example 58

5-(2-aminopyrimidin-5-yl)-N-(2-(methylsulfonyl)ethyl)-7-morpholinothiazolo[4,5-d]pyrimidin-2-amine 133

5-Chloro-2-(methylsulfonyl)-7-morpholinothiazolo[4,5-d]pyrimidine was reacted with 2-(methylsulfonyl)ethanamine (HCl salt), using 2.8 equiv of triethylamine, via General Procedure C, to give crude 5-chloro-N-(2-(methylsulfonyl)ethyl)-7-morpholinothiazolo[4,5-d]pyrimidin-2-amine, which was then reacted with 5-(4,4,5,5-tetramethyl-1,3,2-dioxaborolan-2-yl)pyrimidin-2-amine via General Procedure C again to give 133 after purification by reverse HPLC. MS (Q1) 437 (M+)

Example 59

2-(4-(5-(2-aminopyrimidin-5-yl)-7-morpholinothiazolo[4,5-d]pyrimidin-2-yl)piperazin-1-yl)ethanol 134

5-Chloro-2-(methylsulfonyl)-7-morpholinothiazolo[4,5-d]pyrimidine was reacted with 2-(piperazin-1-yl)ethanol, via General Procedure C, to give crude 2-(4-(5-chloro-7-morpholinothiazolo[4,5-d]pyrimidin-2-yl)piperazin-1-yl)ethanol, which was then reacted with 5-(4,4,5,5-tetramethyl-1,3,2-dioxaborolan-2-yl)pyrimidin-2-amine via General Procedure C again to give 134 after purification by reverse HPLC. MS (Q1) 444 (M+)

Example 60

5-(2-(4-(methylsulfonyl)piperazin-1-yl)-7-morpholinothiazolo[4,5-d]pyrimidin-5-yl)pyrimidin-2-amine 135

5-Chloro-2-(methylsulfonyl)-7-morpholinothiazolo[4,5-d]pyrimidine was reacted with 1-methylsulfonylpiperazine (HCl salt), using 2.8 equiv of triethylamine, via General Procedure C to give crude 5-chloro-2-(4-methylsulfonylpiperazin-1-yl)-7-morpholinothiazolo[4,5-d]pyrimidine, which was then reacted with 5-(4,4,5,5-tetramethyl-1,3,2-dioxaborolan-2-yl)pyrimidin-2-amine via General Procedure C again to give 135 after purification by reverse HPLC. MS (Q1) 478 (M+)

Example 61

5-(2-aminopyrimidin-5-yl)-7-morpholino-N-(2-morpholinoethyl)thiazolo[4,5-d]pyrimidin-2-amine 136

5-Chloro-2-(methylsulfonyl)-7-morpholinothiazolo[4,5-d]pyrimidine was reacted with 2-morpholinoethanamine via General Procedure C to give crude 5-chloro-7-morpholino-N-(2-morpholinoethyl)thiazolo[4,5-d]pyrimidin-2-amine, which was then reacted with 5-(4,4,5,5-tetramethyl-1,3,2-

Example 62

2-(5-(2-Aminopyrimidin-5-yl)-7-morpholinothiazolo[4,5-d]pyrimidin-2-yl)propan-2-ol 137

5-Chloro-2-(methylsulfonyl)-7-morpholinothiazolo[4,5-d]pyrimidine was slurried in dry methanol/tetrahydrofuran (1:10). The solution was cooled to 0° C. under nitrogen and sodium borohydride (1.1 eq) was added in four portions. The solution was stirred at 0° C. for 30 min. An additional 0.1 eq sodium borohydride was added if necessary. The solvent was removed under vacuum and the resulting residue was purified by silica gel chromatography isocratic 1:1 methylene chloride:ethylacetate. The resulting white solid of 4-(5-chlorothiazolo[4,5-d]pyrimidin-7-yl)morpholine 16 was isolated.

4-(5-Chlorothiazolo[4,5-d]pyrimidin-7-yl)morpholine 16 was slurried in tetrahydrofuran and cooled to −78° C. under nitrogen. Two equivalents of 2M lithium diisopropylamide in heptane/tetrahydrofuran/ethylbenzene were added slowly and the solution was stirred for 30 minutes. Acetone (6 eq) was added and the solution was stirred at −78° C. for an additional one hour. Ice was added and the solution was warmed to room temperature before extraction with methylene chloride. The organic layer was dried with sodium sulfate and concentrated. The resulting residue was purified on silica gel to give the light yellow solid of 2-(5-chloro-7-morpholinothiazolo[4,5-d]pyrimidin-2-yl)propan-2-ol.

2-(5-Chloro-7-morpholinothiazolo[4,5-d]pyrimidin-2-yl)propan-2-ol, 5-pyrimidine-2-amine boronic acid (1.2 eq), and trans-dichlorobis(triphenylphosphine)palladium(II) (0.1 eq) were slurried with equal parts 1M sodium carbonate aqueous solution (3 eq) and acetonitrile. The solution was microwaved at 130° C. for 15 minutes. The solution was evaporated to dryness and purified by reverse phase silica gel chromatography to give the product 137.

Example 63

5-(7-Morpholino-2-(thiazol-4-yl)thiazolo[4,5-d]pyrimidin-5-yl)pyrimidin-2-amine 138

5-Chloro-2-(methylthio)-7-morpholinothiazolo[4,5-d]pyrimidine was combined with 4-(tributylstannyl)thiazole (1.1 eq), cesium fluoride (2 eq), copper iodide (2 eq), tetrakis(triphenylphosphine)palladium (0.1 eq) in dimethylformamide and microwaved 110° C. for 15 minutes. Methylene chloride was added the solution was filtered through silica washing with methanol. The organic layer was evaporated to dryness and the resulting residue was purified by silica gel chromatography to yield 5-chloro-7-morpholino-2-(thiazol-4-yl)thiazolo[4,5-d]pyrimidine as a pale yellow solid.

5-Chloro-7-morpholino-2-(thiazol-4-yl)thiazolo[4,5-d]pyrimidine, 5-pyrimidine-2-amine boronic acid (1.2 eq), and trans-dichlorobis(triphenylphosphine)palladium(II) (0.1 eq) were slurried with equal parts 1M sodium carbonate (3 eq) and acetonitrile. The solution was microwaved at 130° C. for 15 minutes. Acetonitrile was added and the solution was filtered. The resulting organic layer was purified by reverse phase silica gel chromatography to give the product 138. MS data: (ESI+): MH+ 399.

Example 64

5-(2,7-Dimorpholinothiazolo[4,5-d]pyrimidin-5-yl)pyrimidin-2-amine 139

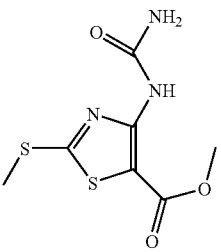

76

In 150 mL methylene chloride, 4-amino-2-methylthio-5-thiazolcarboxylic acid methyl ester (0.05 mol) was dissolved and cooled to −78° C. under nitrogen gas. Stirring, 0.07 mol (1.4 eq) of chlorosulfonyl isocyanate was added slowly to give a brown solution. The reaction was warmed slowly to 0° C. and a white precipitate forms. After 30 minutes, the solution was evaporated under vacuum, resuspended in 40 mL of 6N hydrochloric acid (4 eq) and heated to 100° C. After 30 minutes, the solution was cooled to room temp, neutralized with saturated sodium carbonate followed by saturated sodium bicarbonate. The white solid was isolated by filtration to give methyl 2-(methylthio)-4-ureidothiazole-5-carboxylate 76.

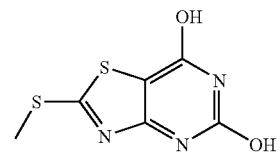

77

Methyl 2-(methylthio)-4-ureidothiazole-5-carboxylate was suspended in 2 M ammonia in methanol (100 eq). The solution was refluxed overnight, cooled to room temperature and filtered (on larger scale, this reaction has been run in a sealed tube). The resulting white solid, 2-(methylthio)thiazolo[4,5-d]pyrimidine-5,7-diol 77, was triturated with benzene and dried on high vacuum overnight.

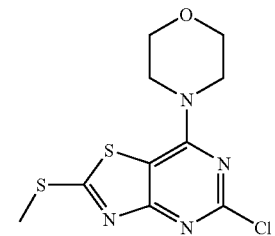

78

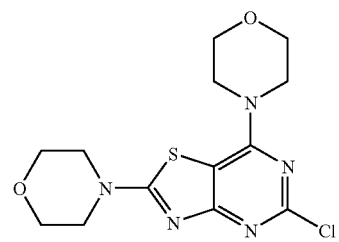

79

To 2-(methylthio)thiazolo[4,5-d]pyrimidine-5,7-diol 77, phosphoroxidchloride (25 eq) was added and the resulting solution was cooled to −40° C. Diisopropylethylamine (6 eq) was added slowly. The solution was then heated to 120° C.

overnight to give a brown solution. The solution was cooled to room temperature, and poured into ice water. Ammonium hydroxide (28% solution) was added to achieve a neutral pH. The solution was extracted with ethyl acetate, dried with sodium sulfate anhydrous and concentrated. The crude brown solid was slurried in methanol and morpholine (6 eq) was added. The solution was stirred at room temperature for 30 min, solvent was removed under vacuum and ethyl acetate was added. The organic was washed with saturated sodium bicarbonate solution. Both the precipitate and the organic layers contained product and were subjected to silica gel chromatography to yield 5-chloro-2-(methylthio)-7-morpholinothiazolo[4,5-d]pyrimidine 78 and 5-chloro-2,7-dimorpholinothiazolo[4,5-d]pyrimidine 79.

5-Chloro-2,7-dimorpholinothiazolo[4,5-d]pyrimidine 79, 5-pyrimidine-2-amine boronic acid (1.2 eq), and trans-dichlorobis(triphenylphosphine)palladium(II) (0.1 eq) were slurried with equal parts 1M sodium carbonate (3 eq) and acetonitrile. The solution was microwaved at 150° C. for 10 minutes. An additionally 0.1 equivalents of trans-dichrobis (triphenylphosphine)palladium(II) was added and the solution was microwaved an additional 10 minutes at 150° C. Water was added and the solution was filtered. The resulting precipitate was purified by reverse phase silica gel chromatography to give 139.

Example 65

N-(3-(5-(2-aminopyrimidin-5-yl)-7-morpholinothiazolo[4,5-d]pyrimidin-2-yl)phenyl)acetamide 140

4-(5-Chloro-2-iodothiazolo[4,5-d]pyrimidin-7-yl)morpholine 27, 3-acetamido-phenyl boronic acid (1.2 eq), and trans-dichlorobis(triphenylphosphine)palladium(II) (0.1 eq) were slurried with equal parts 1M sodium carbonate aqueous solution (3 eq) and acetonitrile. The solution was microwaved at 90° C. for 10 minutes. Water was added and the solution was filtered. The aqueous layer was dried and combined with 5-pyrimidine-2-amine boronic acid (1.2 eq) and trans-dichlorobis(triphenylphosphine)palladium(II) (0.1 eq) and slurried with equal parts 1M sodium carbonate aqueous solution (3 eq) and acetonitrile. The solution was microwaved at 150° C. for 10 minutes. Water was added and the solution was filtered. The resulting precipitate was purified by reverse phase silica gel chromatography to yield 140.

Example 66

(5-(1H-indazol-4-yl)-7-morpholinothiazolo[4,5-d] pyrimidin-2-yl)(4-(methylsulfonyl)piperazin-1-yl) methanone 141

4-(5-Chlorothiazolo[4,5-d]pyrimidin-7-yl)morpholine 16 was dissolved in tetrahydrofuran and iodine (3 eq) was added. The solution was cooled to −50° C. and potassium bis(trimethylsilyl)amide (1.2 eq of 0.5M solution in toluene) was added over a period of 10 minutes. The solution was warmed to room temperature and stirred overnight. Water was added to quench the reaction and the tetrahydrofuran was removed in vacuo. The residue was brought up in methylene chloride, washed with saturated sodium bicarbonate solution and dried with magnesium sulfate. The solution was concentrated a purified by silica gel chromatography to yield 4-(5-chloro-2-iodothiazolo[4,5-d]pyrimidin-7-yl)morpholine 27.

4-(5-Chloro-2-iodothiazolo[4,5-d]pyrimidin-7-yl)morpholine 27 was dissolved in tetrahydrofuran and combined with triethylamine, 1-methylsulfonylpiperazine hydrochloride (2 eq), and trans-dichlorobis(triphenylphosphine)palladium(II) (0.1 eq). The solution was flushed with carbon monoxide stirred under a carbon monoxide balloon at 55° C. overnight. The solution was cooled to room temperature. Water was added and the solution was filtered to yield the tan product of (5-chloro-7-morpholinothiazolo[4,5-d]pyrimidin-2-yl)(4-methylsulfonylpiperazin-1-yl)methanone.

(5-Chloro-7-morpholinothiazolo[4,5-d]pyrimidin-2-yl) (4-methylsulfonylpiperazin-1-yl)methanone, 1H-indazol-4-yl-4-boronic acid (2.5 eq), and trans-dichlorobis(triphenylphosphine)palladium(II) (0.1 eq) were slurried with equal parts 1M sodium carbonate aqueous solution (3 eq) and acetonitrile. The solution was microwaved at 140° C. for 10 minutes. Water was added and the solution was filtered. The resulting precipitate was washed with methylene chloride and the organic layer was purified by silica gel chromatography followed by reverse phase silica gel chromatography to give the product 141.

Example 67

5-(2-(3-(methylsulfonyl)phenyl)-7-morpholinothiazolo[4,5-d]pyrimidin-5-yl)pyrimidin-2-amine 142

5-Chloro-2-iodo-7-morpholinothiazolo[4,5-d]pyrimidine, 3-(methylsulfonyl)phenyl boronic acid and trans-dichlorobis(triphenylphosphine)palladium(II) (0.1 eq) were slurried with equal parts 1M sodium carbonate (3 eq) and acetonitrile. The solution was microwaved at 90° C. for 10 minutes. Water was added and the solution was filtered. The aqueous layer was dried and combined with 5-pyrimidine-2-amine boronic acid (1.2 eq), and trans-dichlorobis(triphenylphosphine)palladium(II) (0.1 eq) were slurried with equal parts 1M sodium carbonate aqueous solution (3 eq) and acetonitrile. The solution was microwaved at 150° C. for 10 minutes. Water was added and the solution was filtered. The resulting precipitate was purified by reverse phase silica gel chromatography to yield 142.

Example 68

5-(2-(4-methoxypyridin-3-yl)-7-morpholinothiazolo [4,5-d]pyrimidin-5-yl)pyridin-2-amine 143

5-Chloro-2-iodo-7-morpholinothiazolo[4,5-d]pyrimidine, 4-methoxypyridine-3-boronic acid hydrate, and trans-dichlorobis(triphenylphosphine)palladium(II) (0.1 eq) were slurried with equal parts 1M sodium carbonate aqueous solution (3 eq) and acetonitrile. The solution was microwaved at 100° C. for 10 minutes. Water was added and the solution was filtered to give the product 5-chloro-2-(4-methoxypyridin-3-yl)-7-morpholinothiazolo[4,5-d]pyrimidine.

5-Chloro-2-(4-methoxypyridin-3-yl)-7-morpholinothiazolo[4,5-d]pyrimidine combined with 5-pyridine-2-amine boronic acid (1.2 eq), and trans-dichlorobis(triphenylphosphine)palladium(II) (0.1 eq) and slurried with equal parts 1M sodium carbonate aqueous solution (3 eq) and acetonitrile. The solution was microwaved at 150° C. for 10 minutes. The solution was dried in vacuo and purified by reverse phase silica gel chromatography to yield 143.

Example 69

5-(6-aminopyridin-3-yl)-N-methyl-N-(1-methylpiperidin-4-yl)-7-morpholinothiazolo[4,5-d]pyrimidin-2-amine 144

5-Chloro-2-(methylthio)-7-morpholinothiazolo[4,5-d]pyrimidine was dissolved in methanol. Oxone (2.2 eq) was added in water (10:1 ratio methanol:water). The solution was heated to 50° C. for 2.5 hours. One additional equivalent of oxone was added (if needed) and solution was stirred at 50° C.

for an additional 1 hour. The solution was cooled to room temperature and methylene chloride was added. The resulting solid was filtered off and rinsed with methylene chloride. The organic solution was washed with saturated sodium bicarbonate solution (pH test neutral), dried with magnesium sulfate and concentrated to yield 5-chloro-2-(methylsulfonyl)-7-morpholinothiazolo[4,5-d]pyrimidine.

5-Chloro-2-(methylsulfonyl)-7-morpholinothiazolo[4,5-d]pyrimidine was dissolved in tetrahydrofuran and 1-methyl-4-(methylamine)piperidine (1.2 eq) was added slowly. The solution was stirred overnight and the solvent was removed in vacuo. The residue was dissolved in methylenechloride, washed with saturated solution of saturated sodium bicarbonate, and the organic layer was dried with magnesium sulfate. The resulting yellow oil was purified by silica gel chromatography to give 5-chloro-N-methyl-N-(1-methylpiperidin-4-yl)-7-morpholinothiazolo[4,5-d]pyrimidin-2-amine as a yellow solid.

5-Chloro-N-methyl-N-(1-methylpiperidin-4-yl)-7-morpholinothiazolo[4,5-d]pyrimidin-2-amine, 2-aminopyridine-5-boronic acid pinacol ester (2 eq), and trans-dichlorobis(triphenylphosphine)palladium(II) (0.1 eq) were slurried with equal parts 1M potassium acetate (3 eq) and acetonitrile. The solution was microwaved at 140° C. for 10 minutes. The solvent was removed in vacuo and the resulting precipitate was purified by reverse phase silica gel chromatography to give the product 144.

Alternatively, 5-chloro-2-(methylsulfonyl)-7-morpholinothiazolo[4,5-d]pyrimidine was reacted with 1-methyl-4-(methylamino)piperidine, without triethylamine, via General Procedure C, to give crude 5-chloro-N-methyl-N-(1-methylpiperidin-4-yl)-7-morpholinothiazolo[4,5-d]pyrimidin-2-amine, which was then reacted with 5-(4,4,5,5-tetramethyl-1,3,2-dioxaborolan-2-yl)pyridin-2-amine via General Procedure C again to give 144 after purification by silica gel chromatography. MS (Q1) 441 (M$^+$)

Example 70

5-(2-(4-(methylsulfonyl)piperazin-1-yl)-7-morpholinothiazolo[4,5-d]pyrimidin-5-yl)pyridin-2-amine 145

5-Chloro-2-(methylsulfonyl)-7-morpholinothiazolo[4,5-d]pyrimidine (1.0 eq) was dissolved in 1,2-dichloroethane (0.1 M). 1-methylsulfonylpiperazine (1.1 eq) and sodium acetate (1.1 eq) were added. The solution was stirred for 2 h at 70° C. and the solvent was removed in vacuo. The residue was purified by silica gel chromatography to give 5-chloro-2-(4-methylsulfonylpiperazin-1-yl)-7-morpholinothiazolo[4,5-d]pyrimidine. This intermediate, 5-(4,4,5,5-tetramethyl-1,3,2-dioxaborolan-2-yl)pyridin-2-amine (2.0 eq), trans-dichlorobis(triphenylphosphine)palladium(II) (0.10 eq), 1M KOAc (3.0 eq) and a 6× volume of acetonitrile were microwaved at 150° C. for 15 minutes. Upon completion, reaction mixture was concentrated in vacuo and crude mixture was purified by silica gel chromatography to give 145. MS (Q1) 477 (M$^+$)

Example 71

5-(6-aminopyridin-3-yl)-7-morpholino-N-phenylthiazolo[4,5-d]pyrimidin-2-amine 146

5-Chloro-2-(methylsulfonyl)-7-morpholinothiazolo[4,5-d]pyrimidine (1.0 eq) and aniline (1.0 eq) were heated in toluene at 60° C. for 15 h. Upon completion, reaction mixture was concentrated in vacuo and crude mixture was purified by silica gel chromatography to give intermediate 5-chloro-7-morpholino-N-phenylthiazolo[4,5-d]pyrimidin-2-amine which was reacted with 5-(4,4,5,5-tetramethyl-1,3,2-dioxaborolan-2-yl)pyridin-2-amine (2.0 eq) and bis(triphenylphosphine)palladium(II) dichloride (0.10 eq) in 1M KOAc aqueous solution (3.0 eq) and a 4× volume of acetonitrile and heated to 150° C. in a sealed microwave reactor for 10 min. Upon completion, reaction mixture was concentrated in vacuo and crude mixture was purified by silica gel chromatography to give 146. MS (Q1) 406 (M)

Example 72

4-(5-(1H-indazol-4-yl)-2-(methylthio)thiazolo[4,5-d]pyrimidin-7-yl)morpholine 147

5-Chloro-7-morpholino-2-(thiazol-4-yl)thiazolo[4,5-d]pyrimidine, 1H-indazol-4-yl-4-boronic acid (2.5 eq), and trans-dichlorobis(triphenylphosphine)palladium(II) (0.1 eq) were slurried with equal parts 1M potassium acetate (3 eq) and acetonitrile. The solution was microwaved at 150° C. for 15 minutes. The solution filtered and the solution was dried in vacuo. The resulting residue was purified by reverse phase silica gel chromatography to give the product 147.

Example 73 p110α (alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110alpha PI3K (Upstate Cell Signaling Solutions, Charlottesville, Va.) starting at a final concentration of 20 ug/mL in polarization buffer (10 mM Tris pH 7.5, 50 mM NaCl, 4 mM MgCl$_2$, 0.05% Chaps, and 1 mM DTT) to 10 mM PIP$_2$ (Echelon-Inc., Salt Lake City, Utah.) final concentration. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore ($\lambda$ex=530 nm; $\lambda$em=590 nm) in 384-well black low volume Proxiplates (PerkinElmer, Wellesley, Mass.) Fluorescence polarization values were plotted as a function of the protein concentration, and the EC$_{50}$ values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor IC$_{50}$ values were determined by addition of the 0.04 mg/mL p110alpha PI3K (final concentration) combined with PIP$_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore ($\lambda$ex=530 nm; $\lambda$em=590 nm) in 384-well black low volume proxi plates (PerkinElmer, Wellesley, Mass.) Fluorescence polarization values were plotted as a function of the antagonist concentration, and the IC$_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 uM. The compound was serially diluted in 100% DMSO. The kinase reaction was incubated for 1 h at room temperature, and the reaction was terminated by the addition of PBS. $IC_{50}$ values were subsequently determined using sigmoidal dose-response curve fit (variable slope).

Example 74 p110 Isoform Selectivity Scintillation Proximity Binding Assay

The ability of Formula Ia and Ib compounds from Table 1 to inhibit the lipid kinase activity of purified preparations of human PI3K isoforms alpha, beta, delta, and gamma is determined by a radiometric scintillation proximity assay (SPA, GE Healthcare, Amersham Biosciences). Concentration dependent inhibition at 50% ($IC_{50}$ µMol) is determined for all four isoforms (alpha) and fold potency over beta, delta, and gamma relative to alpha may be calculated.

Example 75

In Vitro Cell Proliferation Assay

Efficacy of Formula Ia and Ib compounds were measured by a cell proliferation assay employing the following protocol (Promega Corp. Technical Bulletin TB288; Mendoza et al (2002) Cancer Res. 62:5485-5488):

1. An aliquot of 100 pt of cell culture containing about $10^4$ cells (PC3, Detroit562, or MDAMB361.1) in medium was deposited in each well of a 384-well, opaque-walled plate.
2. Control wells were prepared containing medium and without cells.
3. The compound was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Alternatively, cells are seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Example 76

Caco-2 Permeability

Caco-2 cells are seeded onto Millipore Multiscreen plates at $1\times10^5$ cells/cm², and cultured for 20 days. Assessment of compound permeability is subsequently conducted. The compounds are applied to the apical surface (A) of cell monolayers and compound permeation into the basolateral (B) compartment was measured. This is performed in the reverse direction (B-A) to investigate active transport. A permeability coefficient value, $P_{app}$, for each compound, a measure of the rate of permeation of the compound across the membrane, is calculated. Compounds are grouped into low ($P_{app}</=1.0\times10^6$ cm/s) or high ($P_{app}>/=1.0\times10^6$ cm/s) absorption potential based on comparison with control compounds with established human absorption.

Example 77

Hepatocyte Clearance

Suspensions of cryopreserved human hepatocytes are used. Incubations are performed at compound concentration of 1 mM or 3 µM at a cell density of $0.5\times10^6$ viable cells/mL. The final DMSO concentration in the incubation is about 0.25%. Control incubations are also performed in the absence of cells to reveal any non-enzymatic degradation. Duplicate samples (50 µL) are removed from the incubation mixture at 0, 5, 10, 20, 40 and 60 minutes (control sample at 60 minutes only) and added to methanol-containing internal standard (100 µL) to terminate the reaction. Tolbutamide, 7-hydroxycoumarin, and testosterone may be used as control compounds. Samples are centrifuged and the supernatants at each time point pooled for analysis by LC-MSMS. From a plot of ln peak area ratio (parent compound peak area/internal standard peak area) against time, intrinsic clearance ($CL_{int}$) is calculated as follows: $CL_{int}$ (µl/min/million cells)=V×k, where k is the elimination rate constant, obtained from the gradient of ln concentration plotted against time; V is a volume term derived from the incubation volume and is expressed as µL $10^6$ cells$^{-1}$.

Example 78

Cytochrome P450 Inhibition

Compounds of the invention may be screened against CYP450 targets (e.g. 1A2, 2C9, 2C19, 2D6, 3A4) at 10 concentrations in duplicate, with a top concentration of 100 uM being used. Standard inhibitors (furafylline, sulfaphenazole, tranylcypromine, quinidine, ketoconazole) are used as controls. Plates are read using a BMG LabTechnologies PolarStar in fluorescence mode.

Example 79

Cytochrome P450 Induction

Freshly isolated human hepatocytes from a single donor may be cultured for 48 h prior to addition of test compound at three concentrations and incubated for 72 h. Probe substrates for CYP3A4 and CYP1A2 are added for 30 minutes and 1 h before the end of the incubation. At 72 h, cells and media are removed and the extent of metabolism of each probe substrate quantified by LC-MS/MS. The experiment is controlled by using inducers of the individual P450s incubated at one concentration in triplicate to determine the extent of induction of cytochrome P450 enzymes.

Example 80

Plasma Protein Binding

Solutions of test compound (5 um, 0.5% final DMSO concentration) are prepared in buffer and 10% plasma (v/v in buffer). A 96 well HT dialysis plate is assembled so that each well is divided in two by a semi-permeable cellulose membrane. The buffer solution is added to one side of the membrane and the plasma solution to the other side; incubations are then conducted at 37° C. over 2 h in triplicate. The cells are subsequently emptied, and the solutions for each batch of compounds are combined into two groups (plasma-free and plasma-containing) then analyzed by LC-MSMS using two sets of calibration standards for plasma-free (6 points) and plasma-containing solutions (7 points). The fraction unbound value for the compounds of Table 1 is calculated as: highly protein bound compounds (>/=90% bound) had an Fu</=0.1.

Example 81 hERG Channel Blockage

The compounds of Tables 1 may be evaluated for modulation of rubidium efflux from HEK-294 cells stably expressing hERG potassium channels using established flux methodology. Cells are prepared in medium containing RbCl and plated into 96-well plates and grown overnight to form monolayers. The efflux experiment is initiated by aspirating the media and washing each well with 3×100 µL of pre-incubation buffer (containing low [K$^+$]) at room temperature. Following the final aspiration, 50 µL of working stock (2×) compound is added to each well and incubated at room temperature for 10 minutes. 50 µL of stimulation buffer (containing high [K+]) is then added to each well giving the final test compound concentrations. Cell plates are then incubated at room temperature for a further 10 minutes and 80 µL of supernatant from each well is then transferred to equivalent wells of a 96-well plate and analyzed via atomic emission spectroscopy. The compound is screened as 10 pt duplicate $IC_{50}$ curves, n=2, from a top concentration of 100 µM.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound selected from Formula Ia and Formula Ib:

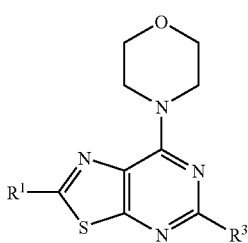

Ia

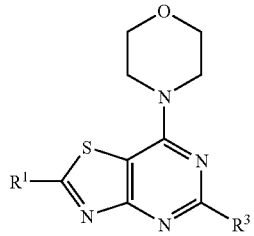

Ib and stereoisomers, geometric isomers, tautomers, or pharmaceutically acceptable salts thereof, wherein:

$R^1$ is selected from H, F, Cl, Br, I, CN, —$(CR^{14}R^{15})_m NR^{10}R^{11}$, —$C(R^{14}R^{15})_n NR^{12}C(=Y)R^{10}$, —$(CR^{14}R^{15})_n NR^{12}S(O)_2R^{10}$, —$(CR^{14}R^{15})_m OR^{10}$, —$(CR^{14}R^{15})_n S(O)_2R^{10}$, —$(CR^{14}R^{15})_n S(O)_2NR^{10}R^{11}$, —$C(OR^{10})R^{11}R^{14}$, —$C(=Y)R^{10}$, —$C(=Y)OR^{10}$, —$C(=Y)NR^{10}R^{11}$, —$C(=Y)NR^{12}OR^{10}$, —$C(=O)NR^{12}S(O)_2R^{10}$, —$C(=O)NR^{12}(CR^{14}R^{15})_m NR^{10}R^{11}$, —$NO_2$, —$NR^{12}C(=Y)R^{11}$, —$NR^{12}C(=Y)OR^{11}$, —$NR^{12}C(=Y)NR^{10}R^{11}$, —$NR^{12}S(O)_2R^{10}$, —$NR^{12}SO_2NR^{10}R^{11}$, —$SR^{10}$, —$S(O)_2R^{10}$, —$S(O)_2NR^{10}R^{11}$, —$SC(=Y)R^{10}$, —$SC(=Y)OR^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is a carbon linked monocyclic heteroaryl, a carbon linked fused bicyclic $C_3$-$C_{20}$ heterocyclyl, or a carbon linked fused bicyclic $C_1$-$C_{20}$ heteroaryl, where the monocyclic heteroaryl, fused bicyclic $C_3$-$C_{20}$ heterocyclyl, and fused bicyclic $C_1$-$C_{20}$ heteroaryl are optionally substituted with one or more groups selected from F, Cl, Br, I, —CN, —$NR^{10}R^{11}$, —$OR^{10}$, —$C(O)R^{10}$, —$NR^{10}C(O)R^{11}$, —$N(C(O)R^{11})_2$, —$NR^{10}C(O)NR^{10}R^{11}$, —$NR^{12}S(O)_2R^{10}$, —$C(=O)OR^{10}$, —$C(=O)NR^{10}R^{11}$, $C_1$-$C_{12}$ alkyl and ($C_1$-$C_{12}$ alkyl)-$OR^{10}$;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached form a $C_2$-$C_{20}$ heterocyclic ring optionally substituted with one or more groups independently selected from oxo, $(CH_2)_m OR^{12}$, $NR^{12}R^{12}$, $CF_3$, F, Cl, Br, I, $SO_2R^{12}$, $C(=O)R^{12}$, $NR^{12}C(=Y)R^{12}$, $NR^{12}S(O)_2R^{12}$, $C(=Y)NR^{12}R^{12}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring;

where said alkyl, alkenyl, alkynyl, carbocyclyl, heterocyclyl, aryl, and heteroaryl, are optionally substituted with one or more groups independently selected from F, Cl, Br, I, CN, $CF_3$, —$NO_2$, oxo, $R^{10}$, —$C(=Y)R^{10}$, —$C(=Y)OR^{10}$, —$C(=Y)NR^{10}R^{11}$, —$(CR^{14}R^{15})_n NR^{10}R^{11}$, —$(CR^{14}R^{15})_n OR^{10}$, —$NR^{10}R^{11}$, —$NR^{12}C(=Y)R^{10}$, —$NR^{12}C(=Y)OR^{11}$, —$NR^{12}C(=Y)NR^{10}R^{11}$, —$(CR^{14}R^{15})_m NR^{12}SO_2R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, —$SR^{10}$, —$S(O)R^{10}$, —$S(O)_2R^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

Y is O, S, or NR$^{12}$;

m is 0, 1, 2, 3, 4, 5 or 6; and n is 1, 2, 3, 4, 5 or 6;

with the proviso that, when R$^1$ is —(CR$^{14}$R$^{15}$)$_m$NR$^{10}$R$^{11}$ in which R$^{14}$ and R$^{15}$ are independently selected from H or C$_1$-C$_6$ alkyl, m is 0, 1 or 2, and R$^{10}$ and R$^{11}$ together with the nitrogen to which they are attached form a nitrogen-containing heterocyclic ring having 3 to 20 ring atoms, the ring being optionally substituted as defined above, then R$^3$ is not an indole group which is unsubstituted or substituted.

2. The compound of claim 1 which is Formula Ia:

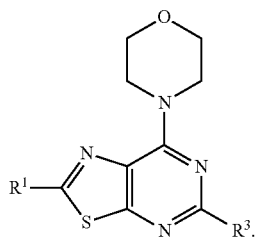

3. The compound of claim 1 which is Formula Ib:

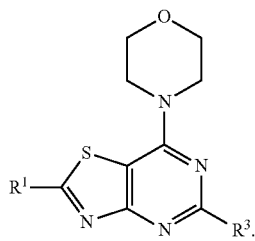

4. The compound of claim 1 wherein R$^3$ is a monocyclic heteroaryl group selected from pyridyl, isoxazolyl, imidazolyl, pyrazolyl, pyrrolyl, thiazolyl, pyridazinyl, pyrimidinyl, pyrazinyl, oxazolyl, furanyl, thienyl, triazolyl, and tetrazolyl.

5. The compound of claim 1 wherein R$^1$ is —(CR$^{14}$R$^{15}$)$_m$NR$^{10}$R$^{11}$ where m is 1, and R$^{10}$ and R$^{11}$ together with the nitrogen to which they are attached form a C$_2$-C$_{20}$ heterocyclic ring selected from morpholinyl, piperidinyl, piperazinyl, and pyrrolidinyl.

6. The compound of claim 5 wherein the C$_2$-C$_{20}$ heterocyclic ring is substituted with one or more groups selected from NR$^{12}$R$^{12}$, CF$_3$, F, Cl, Br, I, SO$_2$R$^{12}$, C(=O)R$^{12}$, NR$^{12}$C(=Y)R$^{12}$, NR$^{12}$S(O)$_2$R$^{12}$, C(=Y)NR$^{12}$R$^{12}$, and C$_1$-C$_{12}$ alkyl.

7. The compound of claim 1 wherein R$^1$ is —(CR$^{14}$R$^{15}$)$_n$NR$^{12}$S(O)$_2$R$^{10}$ where n is 1 or 2; R$^{12}$, R$^{14}$, and R$^{15}$ are independently selected from H and C$_1$-C$_{12}$ alkyl; and R$^{10}$ is C$_1$-C$_{12}$ alkyl or C$_6$-C$_{20}$ aryl.

8. The compound of claim 1 wherein R$^1$ is —(CR$^{14}$R$^{15}$)$_n$OR$^{10}$ where n is 1 or 2, and R$^{10}$, R$^{14}$, and R$^{15}$ are independently selected from H and C$_1$-C$_{12}$ alkyl.

9. The compound of claim 1 wherein R$^1$ is —(CR$^{14}$R$^{15}$)$_n$S(O)$_2$R$^{10}$ where n is 1 or 2, and R$^{14}$ and R$^{15}$ are H.

10. The compound of claim 9 wherein R$^{10}$ is C$_1$-C$_{12}$ alkyl or C$_6$-C$_{20}$ aryl.

11. The compound of claim 1 wherein R$^1$ is —(CR$^{14}$R$^{15}$)$_n$S(O)$_2$NR$^{10}$R$^{11}$ where n is 1 or 2, and R$^{14}$ and R$^{15}$ are H.

12. The compound of claim 1 wherein R$^1$ is —C(=Y)NR$^{10}$R$^{11}$ where Y is O, and R$^{10}$ and R$^{11}$ together with the nitrogen to which they are attached form the C$_2$-C$_{20}$ heterocyclic ring selected from morpholinyl, piperidinyl, piperazinyl, and pyrrolidinyl.

13. The compound of claim 1 wherein R$^1$ is —C(=Y)NR$^{10}$R$^{11}$ where Y is O, and R$^{10}$ and R$^{11}$ are independently selected from H and C$_1$-C$_{12}$ alkyl.

14. The compound of claim 1 wherein R$^1$ is —C(=Y)NR$^{10}$R$^{11}$ where Y is O, and R$^{10}$ and R$^{11}$ are independently selected from H, C$_3$-C$_{12}$ carbocyclyl, C$_2$-C$_{20}$ heterocyclyl, C$_6$-C$_{20}$ aryl, and C$_1$-C$_{20}$ heteroaryl.

15. The compound of claim 1 wherein R$^1$ is —NHR$^{11}$ where R$^{11}$ is C$_3$-C$_{12}$ carbocyclyl, C$_2$-C$_{20}$ heterocyclyl, C$_6$-C$_{20}$ aryl, or C$_1$-C$_{20}$ heteroaryl.

16. The compound of claim 15 wherein R$^{12}$ is phenyl or 4-pyridyl.

17. The compound of claim 1 wherein R$^1$ is —NR$^{12}$C(=Y)R$^{11}$ where Y is O, R$^{12}$ is H or C$_1$-C$_{12}$ alkyl, and R$^{11}$ is C$_1$-C$_{12}$ alkyl, C$_3$-C$_{12}$ carbocyclyl, C$_2$-C$_{20}$ heterocyclyl, C$_6$-C$_{20}$ aryl, or C$_1$-C$_{20}$ heteroaryl.

18. The compound of claim 1 wherein R$^1$ is —NR$^{12}$S(O)$_2$R$^{10}$ where R$^{12}$ is H or C$_1$-C$_{12}$ alkyl, and R$^{10}$ is C$_1$-C$_{12}$ alkyl, C$_3$-C$_{12}$ carbocyclyl, C$_2$-C$_{20}$ heterocyclyl, C$_6$-C$_{20}$ aryl, or C$_1$-C$_{20}$ heteroaryl.

19. The compound of claim 1 wherein R$^1$ is S(O)$_2$NR$^{10}$R$^{11}$ where R$^{10}$ and R$^{11}$ together with the nitrogen to which they are attached form a C$_2$-C$_{20}$ heterocyclic ring selected from morpholinyl, piperidinyl, piperazinyl, and pyrrolidinyl.

20. The compound of claim 1 wherein R$^1$ is S(O)$_2$NR$^{10}$R$^{11}$ where R$^{10}$ and R$^{11}$ are independently selected from H and C$_1$-C$_{12}$ alkyl.

21. The compound of claim 1 wherein R$^1$ is C$_1$-C$_{12}$ alkyl, C$_2$-C$_8$ alkenyl, or C$_2$-C$_8$ alkynyl.

22. The compound of claim 21 wherein R$^1$ is C$_2$-C$_8$ alkynyl is substituted with C$_2$-C$_{20}$ heterocyclyl selected from morpholinyl, piperidinyl, piperazinyl, and pyrrolidinyl.

23. The compound of claim 21 wherein R$^1$ is selected from the groups:

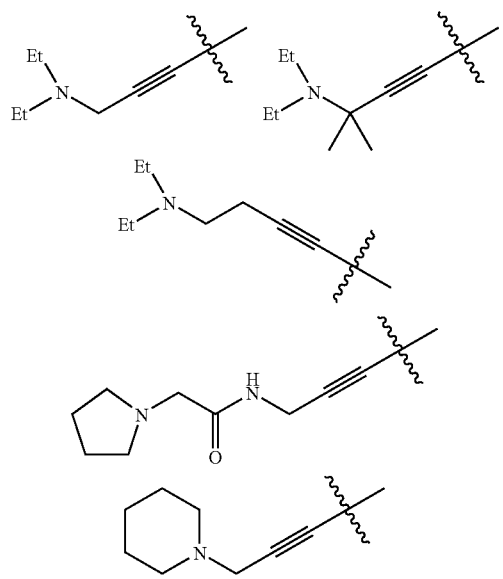

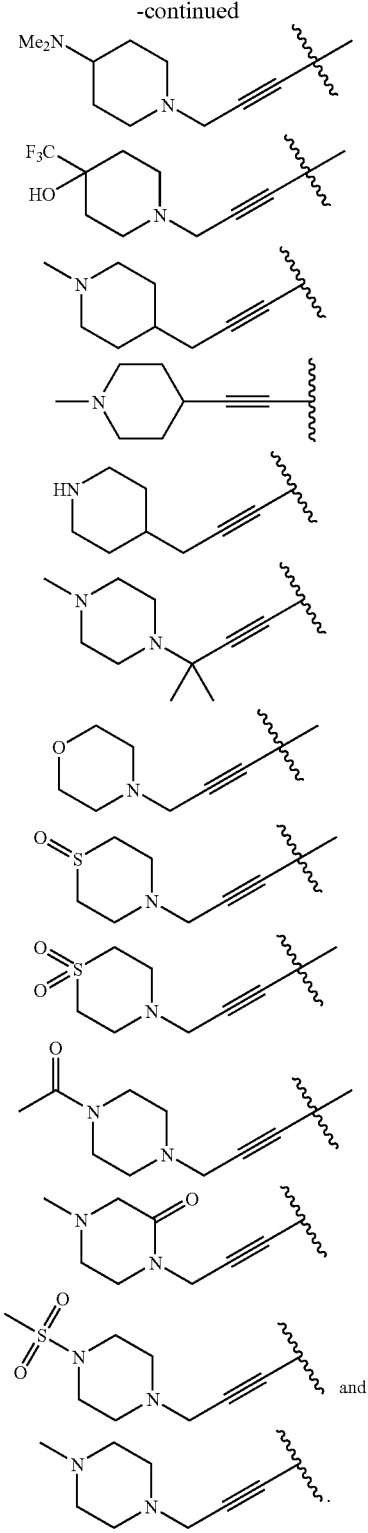

24. The compound of claim 1 wherein $R^1$ is $C_6$-$C_{20}$ aryl.

25. The compound of claim 24 wherein $R^1$ is phenyl substituted with one or more groups selected from N-methylcarboxamide, isopropylsulfonylamino, methylsulfonyl, 2-hydroxy-2-methylpropanamide, 2-hydroxypropanamide, 2-methoxyacetamide, (propan-2-ol)sulfonyl, 2-amino-2-methylpropanamide, 2-aminoacetamide, 2-hydroxyacetamide, methylsulfonylamino, 2-9dimethylamino)acetamide, amino, acetylamino, carboxamide, (4-methylsulfonylpiperazino)-1-methyl, (4-methylpiperazino)-1-methyl, hydroxymethyl, and methoxy.

26. The compound of claim 1 wherein $R^1$ is 2-pyridyl, 3-pyridyl, 4-pyridyl, or 5-pyrimidinyl.

27. The compound of claim 1 wherein $R^3$ is selected from

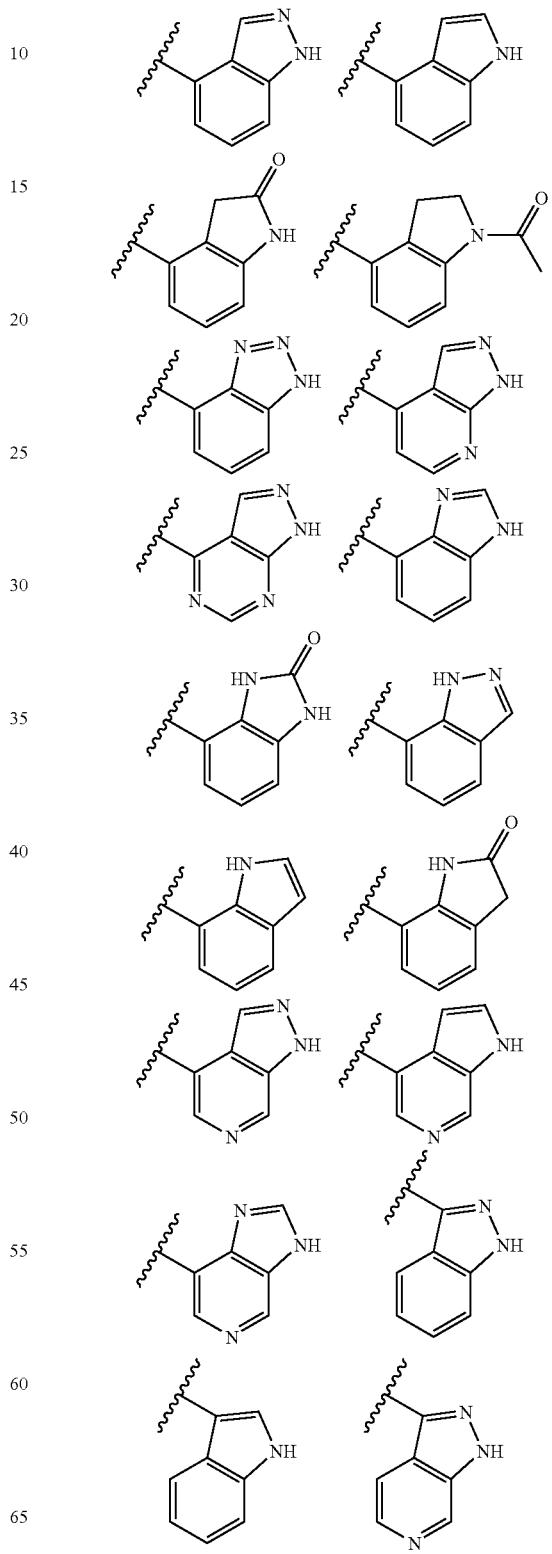

-continued
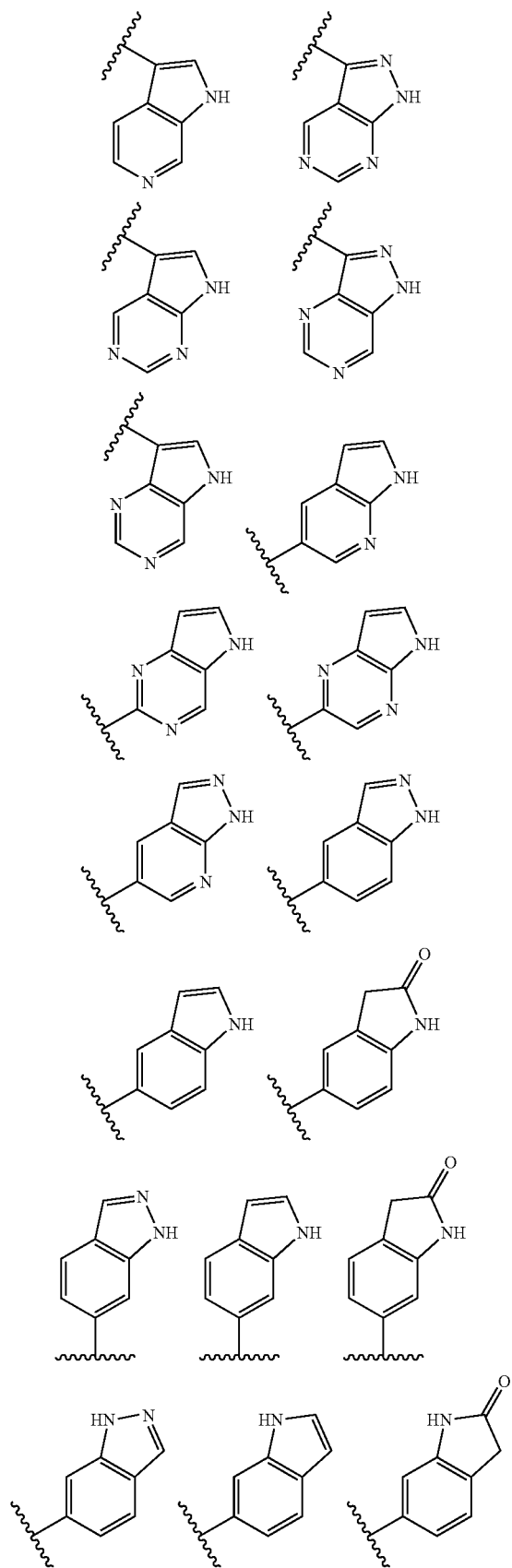
-continued
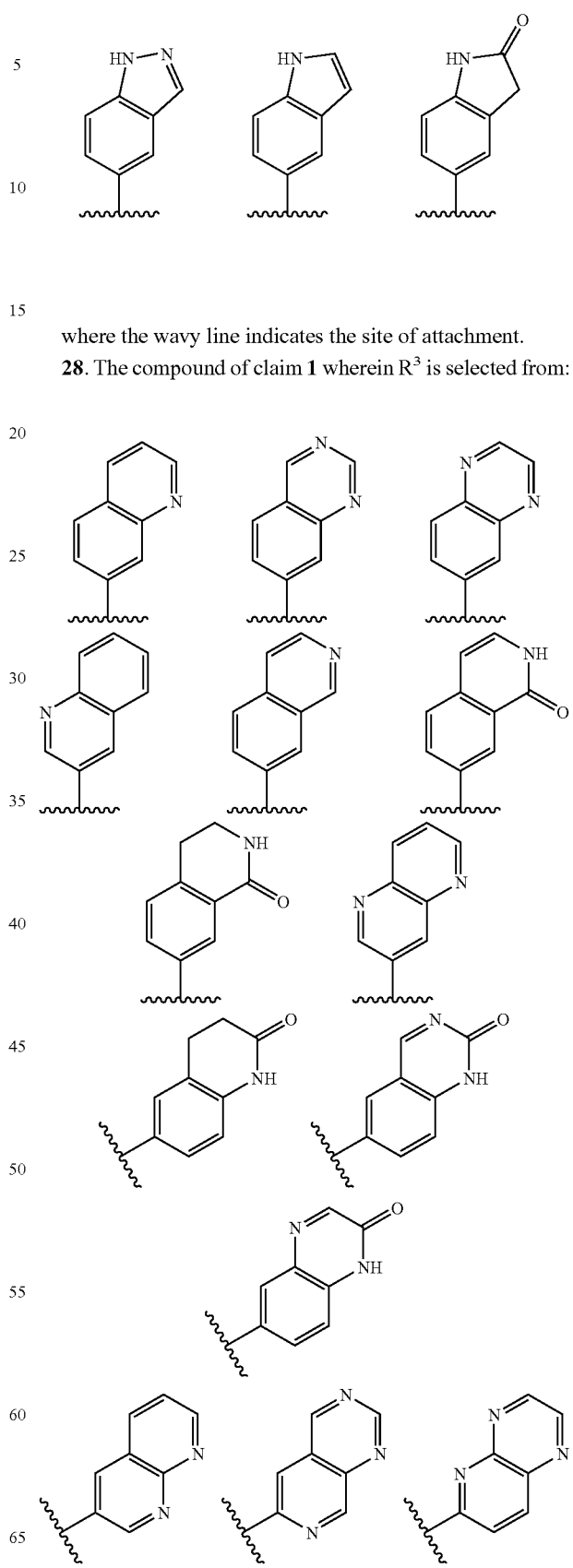
where the wavy line indicates the site of attachment.
28. The compound of claim 1 wherein $R^3$ is selected from:

-continued

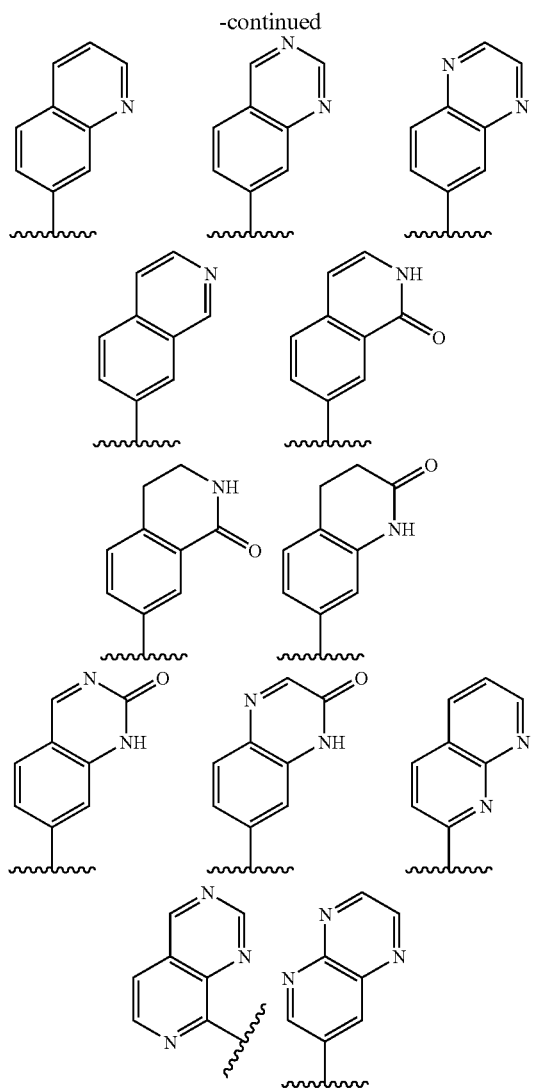

where the wavy line indicates the site of attachment.

29. The compound of claim 28 wherein R³ is 1H-indazol-4-yl.

30. The compound of claim 1 wherein R³ is selected from the structures:

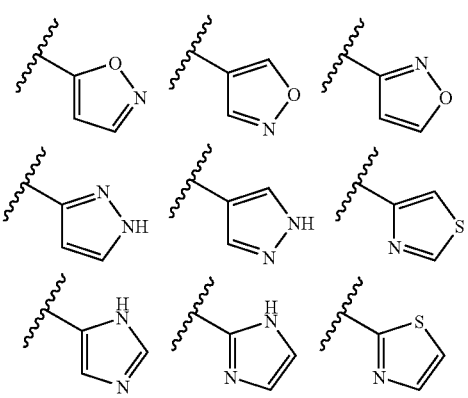

-continued

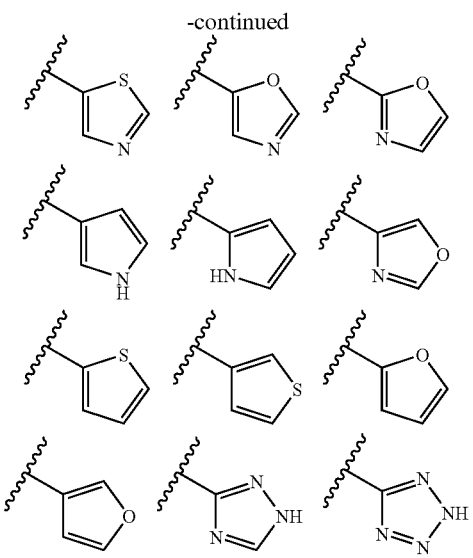

where the wavy line indicates the site of attachment.

31. The compound of claim 1 wherein R³ is selected from the structures:

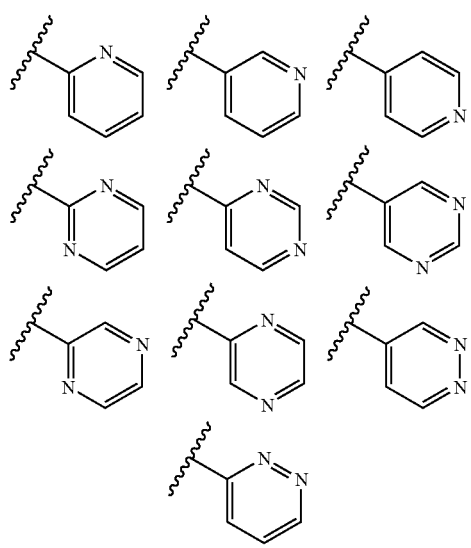

where the wavy line indicates the site of attachment.

32. The compound of claim 1 wherein R³ is selected from the structures:

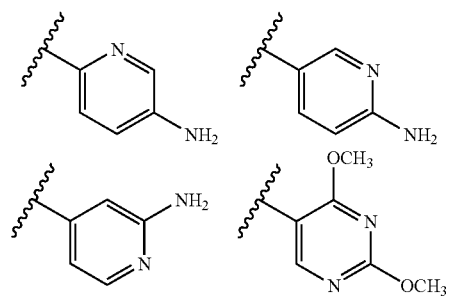

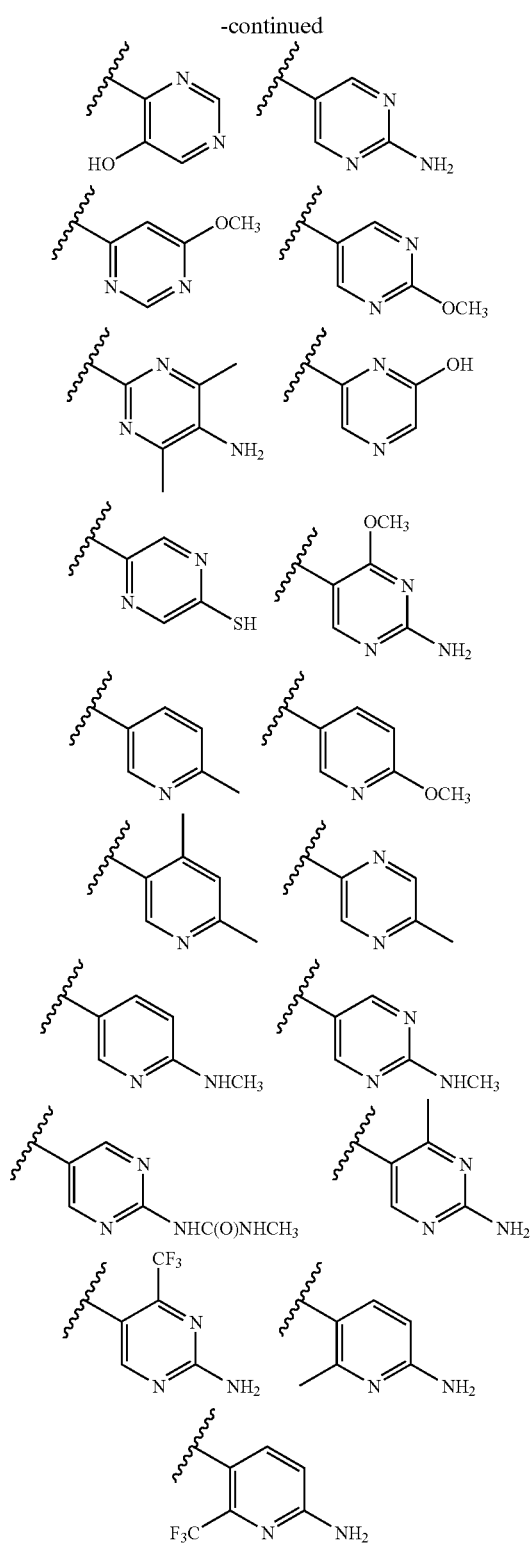

where the wavy line indicates the site of attachment.

33. The compound of claim 1 wherein the monocyclic heteroaryl group, the fused bicyclic $C_3$-$C_{20}$ heterocyclyl, or the fused bicyclic $C_1$-$C_{20}$ heteroaryl is substituted with one or more groups selected from F, —$CF_3$, —$NH_2$, —$NHCH_3$, —OH, —$OCH_3$, —C(O)$CH_3$, —NHC(O)$CH_3$, —N(C(O)$CH_3)_2$, —NHC(O)$NH_2$, —$CO_2$H, —CHO, —$CH_2$OH, —C(=O)$NHCH_3$, —C(=O)$NH_2$, and —$CH_3$.

34. A compound selected from:
N-methyl-5-(2-((4-(methylsulfonyl)piperazin-1-yl)methyl)-7-morpholinothiazolo[5,4-d]pyrimidin-5-yl)pyridin-2-amine;
5-(2-(2-methoxypropan-2-yl)-7-morpholinothiazolo[5,4-d]pyrimidin-5-yl)-N-methylpyridin-2-amine;
5-(2-(2-methoxypropan-2-yl)-7-morpholinothiazolo[5,4-d]pyrimidin-5-yl)-N-methylpyrimidin-2-amine;
5-(2-(2-methoxypropan-2-yl)-7-morpholinothiazolo[5,4-d]pyrimidin-5-yl)pyrimidin-2-amine;
N-methyl-5-(2-(3-(methylsulfonyl)phenyl)-7-morpholinothiazolo[5,4-d]pyrimidin-5-yl)pyridin-2-amine;
(S)-2-hydroxy-1-(4-((7-morpholino-5-(quinolin-3-yl)thiazolo[5,4-d]pyrimidin-2-yl)methyl)piperazin-1-yl)propan-1-one;
(S)-2-hydroxy-1-(4-((5-(2-(methylamino)pyrimidin-5-yl)-7-morpholinothiazolo[5,4-d]pyrimidin-2-yl)methyl)piperazin-1-yl)propan-1-one;
(S)-1-(4-((5-(2-aminopyrimidin-5-yl)-7-morpholinothiazolo[5,4-d]pyrimidin-2-yl)methyl)piperazin-1-yl)-2-hydroxypropan-1-one;
4-(2-(3-(methylsulfonyl)phenyl)-5-(1H-pyrrolo[2,3-b]pyridin-5-yl)thiazolo[5,4-d]pyrimidin-7-yl)morpholine;
N,N-dimethyl-5-(2-((4-(methylsulfonyl)piperazin-1-yl)methyl)-7-morpholinothiazolo[5,4-d]pyrimidin-5-yl)pyrimidin-2-amine;
5-(2-((4-(methylsulfonyl)piperazin-1-yl)methyl)-7-morpholinothiazolo[5,4-d]pyrimidin-5-yl)pyridin-2-amine;
4-(2-((4-(methylsulfonyl)piperazin-1-yl)methyl)-5-(quinolin-3-yl)thiazolo[5,4-d]pyrimidin-7-yl)morpholine;
N-methyl-5-(2-((4-(methylsulfonyl)piperazin-1-yl)methyl)-7-morpholinothiazolo[5,4-d]pyrimidin-5-yl)pyrimidin-2-amine;
N-(3-(5-(2-(methylamino)pyrimidin-5-yl)-7-morpholinothiazolo[5,4-d]pyrimidin-2-yl)benzyl)methanesulfonamide;
N-(3-(7-morpholino-5-(1H-pyrrolo[2,3-b]pyridin-5-yl)thiazolo[5,4-d]pyrimidin-2-yl)benzyl)methanesulfonamide;
4-(2-((4-(methylsulfonyl)piperazin-1-yl)methyl)-5-(1H-pyrrolo[2,3-b]pyridin-5-yl)thiazolo[5,4-d]pyrimidin-7-yl)morpholine;
5-(2-aminopyrimidin-5-yl)-7-morpholino-N-(4-morpholinophenyl)thiazolo[5,4-d]pyrimidin-2-amine;
5-(2-aminopyrimidin-5-yl)-N-(4-(methylsulfonyl)phenyl)-7-morpholinothiazolo[5,4-d]pyrimidin-2-amine;
5-(2-aminopyrimidin-5-yl)-7-morpholino-N-phenylthiazolo[5,4-d]pyrimidin-2-amine;
5-(2-(5-(methylsulfonyl)pyridin-3-yl)-7-morpholinothiazolo[5,4-d]pyrimidin-5-yl)pyrimidin-2-amine;
N-(3-(5-(2-aminopyrimidin-5-yl)-7-morpholinothiazolo[5,4-d]pyrimidin-2-yl)phenyl)methanesulfonamide;
5-(2-((4-(methylsulfonyl)piperazin-1-yl)methyl)-7-morpholinothiazolo[5,4-d]pyrimidin-5-yl)pyrimidin-2-amine;
5-(7-morpholino-2-(6-morpholinopyridin-3-yl)thiazolo[5,4-d]pyrimidin-5-yl)pyrimidin-2-amine;
N-(3-(5-(2-aminopyrimidin-5-yl)-7-morpholinothiazolo[5,4-d]pyrimidin-2-yl)phenyl)acetamide;
N-(4-(5-(2-aminopyrimidin-5-yl)-7-morpholinothiazolo[5,4-d]pyrimidin-2-yl)phenyl)methanesulfonamide;
N-(3-(5-(2-aminopyrimidin-5-yl)-7-morpholinothiazolo[5,4-d]pyrimidin-2-yl)benzyl)methanesulfonamide;
5-(2-(6-aminopyridin-3-yl)-7-morpholinothiazolo[5,4-d]pyrimidin-5-yl)pyrimidin-2-amine;
5-(2-(4-methoxypyridin-3-yl)-7-morpholinothiazolo[5,4-d]pyrimidin-5-yl)pyrimidin-2-amine;

4-(5-(1H-indazol-4-yl)-2-((4(4-methylsulfonyl)piper-azin-1-yl)methyl)thiazolo[5,4-d]pyrimidin-7-yl)morpholine;
2-(5-(2-aminopyrimidin-5-yl)-7-morpholinothiazolo[5,4-d]pyrimidin-2-yl)propan-2-ol;
5-(7-morpholinothiazolo[5,4-d]pyrimidin-5-yl)pyrimidin-2-amine;
5-(2-(3-(methylsulfonyl)phenyl)-7-morpholinothiazolo[5,4-d]pyrimidin-5-yl)pyrimidin-2-amine;
5-(2-aminopyrimidin-5-yl)-N-(2-(methylsulfonypethyl)-7-morpholinothiazolo[4,5-d]pyrimidin-2-amine;
2-(4-(5-(2-aminopyrimidin-5-yl)-7-morpholinothiazolo[4,5-d]pyrimidin-2-yl)piperazin-1-yl)ethanol;
5-(2-(4-(methylsulfonyl)piperazin-1-yl)-7-morpholinothiazolo[4,5-d]pyrimidin-5-yl)pyrimidin-2-amine;
5-(2-aminopyrimidin-5-yl)-7-morpholino-N-(2-morpholinoethyl)thiazolo[4,5-d]pyrimidin-2-amine;
2-(5-(2-aminopyrimidin-5-yl)-7-morpholinothiazolo[4,5-d]pyrimidin-2-yl)propan-2-ol;
5-(7-morpholino-2-(thiazol-4-yl)thiazolo[4,5-d]pyrimidin-5-yl)pyrimidin-2-amine;
5-(2,7-dimorpholinothiazolo[4,5-d]pyrimidin-5-yl)pyrimidin-2-amine;
N-(3-(5-(2-aminopyrimidin-5-yl)-7-morpholinothiazolo[4,5-d]pyrimidin-2-yl)phenyl)acetamide;
(5-(1H-indazol-4-yl)-7-morpholinothiazolo[4,5-d]pyrimidin-2-yl)(4-(methylsulfonyl)piperazin-1-yl)methanone;
5-(2-(3-(methylsulfonyl)phenyl)-7-morpholinothiazolo[4,5-d]pyrimidin-5-yl)pyrimidin-2-amine;
5-(2-(4-methoxypyridin-3-yl)-7-morpholinothiazolo[4,5-d]pyrimidin-5-yl)pyridin-2-amine;
5-(6-aminopyridin-3-yl)-N-methyl-N-(1-methylpiperidin-4-yl)-7-morpholinothiazolo[4,5-d]pyrimidin-2-amine;
5-(2-(4-(methylsulfonyl)piperazin-1-yl)-7-morpholinothiazolo[4,5-d]pyrimidin-5-yl)pyridin-2-amine;
5-(6-aminopyridin-3-yl)-7-morpholino-N-phenylthiazolo[4,5-d]pyrimidin-2-amine; and
4-(5-(1 H-indazol-4-yl)-2-(methylthio)thiazolo[4,5-d]pyrimidin-7-yl)morpholine.

35. A pharmaceutical composition comprised of a compound of claim 1 and a pharmaceutically acceptable carrier, glidant, diluent, or excipient.

36. A process for making a pharmaceutical composition which comprises combining a compound of claim 1 with a pharmaceutically acceptable carrier.

37. A kit comprising:
a) a pharmaceutical composition comprising a compound of claim 1; and
b) instructions for use.

38. A method of making a Formula Ia or Formula Ib compound comprising
reacting a Formula IIa or Formula IIb compound:

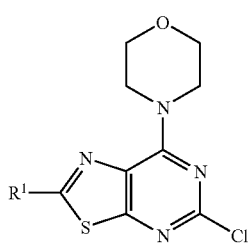

IIa

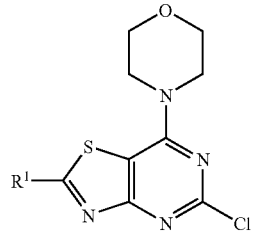

IIb with a boronate compound comprising a monocyclic heteroaryl, a fused bicyclic heterocycle, or a fused bicyclic heteroaryl,
whereby a Formula Ia and Formula Ib compound is formed:

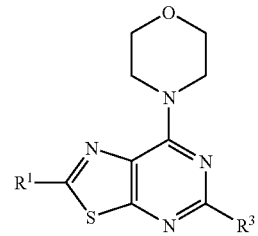

Ia

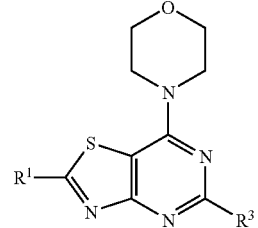

Ib wherein:
$R^1$ is selected from H, F, Cl, Br, I, CN, —$(CR^{14}R^{15})_m$$NR^{10}R^{11}$, —$C(R^{14}R^{15})_n NR^{12}C(=Y)R^{10}$, —$(CR^{14}R^{15})_n NR^{12}S(O)_2 R^{10}$, —$(CR^{14}R^{15})_m OR^{10}$, —$(CR^{14}R^{15})_n S(O)_2 R^{10}$, —$(CR^{14}R^{15})_n S(O)_2 NR^{10}R^{11}$, —$C(OR^{10})R^{11}R^{14}$, —$C(=Y)R^{10}$, —$C(=Y)OR^{10}$, —$C(=Y)NR^{10}R^{11}$, —$C(=Y)NR^{12}OR^{10}$, —$C(=O)NR^{12}S(O)_2 R^{10}$, —$C(=O)NR^{12}(CR^{14}R^{15})_m NR^{10}R^{11}$, —$NO_2$, —$NR^{12}C(=Y)R^{11}$, —$NR^{12}C(=Y)OR^{11}$, —$NR^{12}C(=Y)NR^{10}R^{11}$, —$NR^{12}S(O)_2 R^{10}$, —$NR^{12}SO_2 NR^{10}R^{11}$, —$SR^{10}$, $S(O)_2 R^{10}$, —$S(O)_2 NR^{10}R^{11}$, —$SC(=Y)R^{10}$, —$SC(=Y)OR^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;
$R^3$ is a carbon linked monocyclic heteroaryl, a carbon linked fused bicyclic $C_3$-$C_{20}$ heterocyclyl, or a carbon linked fused bicyclic $C_1$-$C_{20}$ heteroaryl, where the monocyclic heteroaryl, fused bicyclic $C_3$-$C_{20}$ heterocyclyl, and fused bicyclic $C_1$-$C_{20}$ heteroaryl are optionally substituted with one or more groups selected from F, Cl, Br, I, —CN, —$NR^{10}R^{11}$, —$OR^{10}$, —$C(O)R^{10}$, —$NR^{10}C(O)R^{11}$, —$N(C(O)R^{11})_2$, —$NR^{10}C(O)NR^{10}R^{11}$, —$NR^{12}S(O)_2 R^{10}$, —$C(=O)OR^{10}$, —$C(=O)NR^{10}R^{11}$, $C_1$-$C_{12}$ alkyl and ($C_1$-$C_{12}$ alkyl)-$OR^{10}$;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached form a $C_2$-$C_{20}$ heterocyclic ring optionally substituted with one or more groups independently selected from oxo, $(CH_2)_m OR^{12}$, $NR^{12}R^{12}$, $CF_3$, F, Cl, Br, I, $SO_2R^{12}$, $C(=O)R^{12}$, $NR^{12}C(=Y)R^{12}$, $NR^{12}S(O)_2R^{12}$, $C(=Y)NR^{12}R^{12}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring;

where said alkyl, alkenyl, alkynyl, carbocyclyl, heterocyclyl, aryl, and heteroaryl, are optionally substituted with one or more groups independently selected from F, Cl, Br, I, CN, $CF_3$, —$NO_2$, oxo, $R^{10}$, —$C(=Y)R^{10}$, —$C(=Y)OR^{10}$, —$C(=Y)NR^{10}R^{11}$, —$(CR^{14}R^{15})_n NR^{10}R^{11}$, —$(CR^{14}R^{15})_n OR^{10}$, —$NR^{10}R^{11}$, —$NR^{12}C(=Y)R^{10}$, —$NR^{12}C(=Y)OR^{11}$, —$NR^{12}C(=Y)NR^{10}R^{11}$, —$(CR^{14}R^{15})_m NR^{12}SO_2R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, —$SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

Y is O, S, or $NR^{12}$;

m is 0, 1, 2, 3, 4, 5 or 6; and n is 1, 2, 3, 4, 5 or 6;

with the proviso that, when $R^1$ is —$(CR^{14}R^{15})_m NR^{10}R^{11}$ in which $R^{14}$ and $R^{15}$ are independently selected from H or $C_1$-$C_6$ alkyl, m is 0, 1 or 2, and $R^{10}$ and $R^{11}$ together with the nitrogen to which they are attached form a nitrogen-containing heterocyclic ring having 3 to 20 ring atoms, the ring being optionally substituted as defined above, then $R^3$ is not an indole group which is unsubstituted or substituted.

* * * * *

UNITED STATES PATENT AND TRADEMARK OFFICE
CERTIFICATE OF CORRECTION

| | | |
|---|---|---|
| PATENT NO. | : 7,893,059 B2 | Page 1 of 1 |
| APPLICATION NO. | : 12/236317 | |
| DATED | : February 22, 2011 | |
| INVENTOR(S) | : Georgette M. Castanedo et al. | |

It is certified that error appears in the above-identified patent and that said Letters Patent is hereby corrected as shown below:

In the Claims

In Claim 25, Column 120, Line 1:

Replace:
2-9dimethylamino)

With:
2-(dimethylamino)

In Claim 27, Column 121, Line 60 - Column 122, Line 10:

Please delete the last six chemical structures of Claim 27.

In Claim 34, Column 127, Line 1:

Replace:
((4(4-methylsulfonyl)

With:
((4-(methylsulfonyl)

In Claim 34, Column 127, Line 10:

Replace:
(methylsulfonypethyl)

With:
(methylsulfonyl)ethyl)

Signed and Sealed this
Ninth Day of July, 2013

Teresa Stanek Rea
*Acting Director of the United States Patent and Trademark Office*